(12) United States Patent
Perrizo

(10) Patent No.: US 7,958,096 B2
(45) Date of Patent: Jun. 7, 2011

(54) SYSTEM AND METHOD FOR ORGANIZING, COMPRESSING AND STRUCTURING DATA FOR DATA MINING READINESS

(75) Inventor: William K. Perrizo, Fargo, ND (US)

(73) Assignee: NDSU-Research Foundation, Fargo, ND (US)

( * ) Notice: Subject to any disclaimer, the term of this patent is extended or adjusted under 35 U.S.C. 154(b) by 399 days.

(21) Appl. No.: 11/732,501

(22) Filed: Apr. 2, 2007

(65) Prior Publication Data

US 2007/0250522 A1    Oct. 25, 2007

Related U.S. Application Data

(60) Division of application No. 10/367,644, filed on Feb. 14, 2003, now abandoned, which is a continuation-in-part of application No. 09/957,637, filed on Sep. 20, 2001, now Pat. No. 6,941,303.

(60) Provisional application No. 60/234,050, filed on Sep. 20, 2000, provisional application No. 60/237,778, filed on Oct. 4, 2000.

(51) Int. Cl.
*G06F 7/00* (2006.01)
*G06F 17/00* (2006.01)

(52) U.S. Cl. ...................................................... 707/693

(58) Field of Classification Search ............... 707/693
See application file for complete search history.

(56) References Cited

U.S. PATENT DOCUMENTS

| | | | |
|---|---|---|---|
| 4,794,600 A * | 12/1988 | Lin | ............................... 714/760 |
| 5,715,455 A | 2/1998 | Macon, Jr. et al. | |
| 5,724,451 A * | 3/1998 | Shin et al. | ..................... 382/240 |
| 5,960,437 A | 9/1999 | Krawchuk et al. | |
| 5,987,468 A | 11/1999 | Singh et al. | |
| 6,115,716 A * | 9/2000 | Tikkanen et al. | ..................... 1/1 |
| 6,122,628 A * | 9/2000 | Castelli et al. | ....................... 1/1 |
| 6,134,541 A * | 10/2000 | Castelli et al. | ....................... 1/1 |
| 6,185,561 B1 | 2/2001 | Balaban et al. | |
| 6,707,948 B1 * | 3/2004 | Cosman et al. | ............... 382/240 |
| 6,728,728 B2 * | 4/2004 | Spiegler et al. | ............... 707/603 |
| 6,941,303 B2 | 9/2005 | Perrizo | |
| 6,941,318 B1 | 9/2005 | Tamayo et al. | |
| 2001/0042186 A1 * | 11/2001 | Iivonen et al. | ................ 711/207 |
| 2003/0208488 A1 | 11/2003 | Perrizo | |

OTHER PUBLICATIONS

Khan et. al. "K-Nearest Neighbor Classification on Spatial Data Streams". http:wwww.cs.ndsu.nodak.edu/—datasurg/. Final Paper in Word. Jun. 28, 2001. (Annotated pp. 1-23).*

(Continued)

*Primary Examiner* — Cam Y Truong
*Assistant Examiner* — Michael Pham
(74) *Attorney, Agent, or Firm* — Patterson Thuente Christensen Pedersen P.A.

(57) ABSTRACT

Systems and methods for performing data mining in a set of binary data arranged as a plurality of data items in which each data item has a plurality of bits, each bit in a corresponding one of a plurality of bit positions. The set of binary data is arranged in the data storage such that the binary data is in bit position groups. Each bit position group corresponds to a different one of the plurality of bit positions and includes bits of the binary data having that bit position. The binary data of each bit position group is compressed to produce data structures representing the set of binary data. A data mining technique is performed using the plurality of compressed data structures.

21 Claims, 16 Drawing Sheets

OTHER PUBLICATIONS

"Growing Decision Trees on Support-Less Association Rules," K. Wang S. Zhou, Y. He, 6th ACM SIGKDD International Conference on Knowledge Discovery & Data Mining, Boston, Massachusetts, 5 pgs., Aug. 2000.

"An Interval Classifier for Database Mining Applications," R. Agrawal, S. Ghosh, T. Imielinski, B. Iyer, A. Swami, 18th International Conference on Very Large Data Bases, Vancouver, Canada, 14 pgs., Aug. 1992.

"SPRINT: A Scalable Parallel Classifier for Data Mining," J. Shafer, R. Agrawal, M. Mehta, 22nd International Conference on Very Large Data Bases, Bombay, India, pp. 544-555, Sep. 1996.

"Fast Approach for Association Rule Mining for Remotely Sensed Imagery," Q. Zhou, Q. Ding, W. Perrizo, Proceedings of the ISCA International Conference on Computers and Their Applications, New Orleans, Louisiana, 4 pgs., Mar. 2000.

"Efficient and Effective Clustering Method for Spatial Data Mining," R. Ng, J. Han, Proceedings of the 20th International Conference on Very Large Data Bases, Santiago, Chile, 12 pgs., Sep. 1994.

"Data Mining: An Overview from a Database Perspective," M.S. Chen, J Han, P.S. Yu, IEEE Transactions on Knowledge and Data Engineering, vol. 8, No. 6, pp. 1-40, Dec. 1996.

"Mining Association Rules Between Sets of Items in Large Database," R. Agrawal, T. Imielinski, A. Swami, ACM-SIGMOD 93, Washington, D.C., pp. 207-216, May 1993.

"Quad Trees: A Data Structure for Retrieval of Composite Keys," R.A. Finkel, J.L. Bentley, Acta Informatica, vol. 4, pp. 1-9, 1974.

"Mining Frequent Patterns Without Candidate Generation," J. Han, J. Pei, Y. Yin, ACM-SIGMOD 2000, Dallas, Texas, pp. 1-12, May 2000.

"The Application of Association Rule Mining on Remotely Sensed Data," J. Dong, W. Perrizo, Q. Ding, J. Zhou, Proceedings of ACM Symposium on Applied Computers, Italy, 6 pgs., Mar. 2000.

"Finding Interesting Associations Without Support Pruning," E. Cohen, M. Datar, S. Fujiwara, A. Gionis, P. Indyk, R. Motwani, J. Ullman, C. Yang, Proceedings of 26th International Conference on Very Large Data Bases, Cairo, Egypt, 12 pgs., Sep. 2000.

"Integrating Classification and Association Rule Mining," B. Liu, W. Hsu, Y. Ma, The Fourth International Conference on Knowledge Discovery and Data Mining, New York, New York, 7 pgs., Aug. 1998.

"Inferring Decision Trees Using the Minimum Description Length Principle," J.R. Quinlan, R.L. Rivest, Information and Computation, Academic Press, Inc., vol. 80, pp. 227-248, 1989.

"Automatic Subspace Clustering of High Dimensional Data for Data Mining Application," R. Agrawal, J Cehrke, D. Gunopulos, P. Raghavan, Proceedings of ACM SIGMOD International Conference on Management of Data, Seattle, Washington, 12 pgs., Jun. 1998.

"Constraint-Based Clustering in Large Databases," A.K.H. Tung, J. Han, L. V.S. Lakshmanan, R.T. Ng, The 8th International Conference on Database Theory, London, United Kingdom, 15 pgs., Jan. 2001.

"Fast Vertical Mining Using Diffsets," Mohammed J. Zaki, Karam Gouda, Special Interest Group in Knowledge discovery and Data Mining (SIGKDD), Washington DC, 21 pgs, Aug. 2003.

"Request Order Linked List (ROLL): A Concurrency Control Object for Centralized and Distributed Database Systems," William Perrizo, Proceedings of IEEE International Conference on Data Engineering, Kobe, Japan, pp. 278-285, Apr. 11, 1991.

"K-Nearest Neighbor Classification on Spatial Data Streams Using P-Trees", Maleq Khan, Qin Ding, William Perrizo, 6th Pacific-Asia Konwledge Discovery and Data-mining Conference PAKDD, Taipei, Taiwan, pp. 517-528, May, 2002.

"Brute-Force Mining of High-Confidence Classification Rules", Roberto J. Bayardo Jr., Proc. of the Third Int'l Conf. on Knowledge Discovery & Data Mining, pp. 123-126, 1997.

Web site print-out: "Augmenting Data Structures", Note Taker: Srivani Adathakula, Sep. 9, 1998.

File wrapper for U.S. Appl. No. 09/957,637, filed Sep. 20, 2001.

File wrapper for U.S. Appl. No. 10/367,644, filed Feb. 14, 2003.

File wrapper for U.S. Appl. No. 11/791,004, filed Aug. 28, 2007.

International Search Report and Written Opinion for PCT/US05/42101 dated Aug. 30, 2006.

"Fast Algorithms for Mining Association Rules," R. Agrawal, R. Srikant, Proceedings of the International Conference on VLDB, Santiago, Chile, 13 pgs., Sep. 1994.

"Mining Quantitative Association Rules in Large Relational Tables," R. Srikant, R. Agrawal, ACM-SIGMOD 96, Montreal, Canada, pp. 1-12, Jun. 1996.

"An Effective Hash-Based Algorithm for Mining Association Rules," J.S. Park, M.S. Chen, P.S. Yu, ACM-SIGMOD 95, California, pp. 175-186, 1995.

"Multidimensional Access Methods," V. Gaede, O. Gunther, ACM Computing Surveys, vol. 30, No. 2, pp. 171-231, Jun. 1998.

"The Quadtree and Related Hierarchical Data Structure," H. Samet, ACM Computing Survey, vol. 16, No. 2, pp. 188-260, Jun. 1984.

Web site print-out: "What are HH-codes and how can they be used to store hydrographic data?," H. Iverson, Norwegian Hyrdorgraphic Service (NHS), http://www.statkart.no/n1hdb/iveher/hhtext.htm, 7 pgs., Jan. 1998.

"Run-Length Encodings," S.W. Golomb, IEEE Trans. on Information Theory, vol. 12, No. 3, pp. 399-401, Jul. 1966.

"Spatial Data Mining: a Database Approach," M. Ester, H-P. Kriegel, J. Sander, Proceedings of the Fifth International Symposium on Large Spatial Databases (SSD), Berlin, Germany, 20 pgs., 1997.

"Spatial Data Mining: Progress and Challenges Survey Paper," K. Koperski, J. Adhikary, J. Han, Data Mining and Knowledge Discovery, 16 pgs., 1996.

"Spatial Data Mining: Database Primitives, Algorithms and Efficient DBMS Support," M. Ester, A. Frommelt, H-P. Kriegel, J. Sander, Data Mining and Knowledge Discovery, 28 pgs., 1999.

"Discovery of Spatial Association Rules in Geographic Information Databases," K. Koperski, J. Han, SSD, 20 pgs. 1995.

Website print-out: SMILEY (Signature Miner & Interface Language for Earth Yield), Database Systems Users & Research Group at NDSU (DataSURG) http://www.midas.cs.ndsu.nodak.edu/~smiley, 5 pgs., 2002.

"Parameter Optimized, Vertical, Nearest-Neighbor-Vote and Boundary-Based Classification," William Perrizo, Amal Perera, 7 pgs., Dec. 2006.

"Turbo charging Vertical Mining of Large Databases," Pradeeo Shenoy, Gaurav Bhalotia, Jayant R. Haritsa, Mayank Bawa, S. Sudarshan, Devavrat Shah, ACM SIGMOD Record, vol. 29, Issue 2, pp. 22-33, 2000.

"PINE—Podium Incremental Neighbor Evaluator for Classifying Spatial Data", William Perrizo, Qin Ding, Anne Denton, Kirk Scott, Qiang Ding, Maleq Khan, 5 pgs., 2003.

Web site print-out: "Multiplication of Numbers", http://www.cut-the-knot.org/do_you_knot/mul_num.shtml, Apr. 11, 2001.

"Deriving high confidence rules from spatial data using Peano Count Trees", William Perrizo, Qin Ding, Qiang Ding, Amalendu Roy, Advances in Web-Age Information Management, Second International Conference, 12 pgs., 2001.

Web site print-out: "Plane Filling Curves", http://www.cut-the-knot.org/do_you_know/hilbert.shtml, Apr. 11, 2001.

"CHARM: An efficient algorithm for closed association rule mining", M.J. Zaki, C.J. Hsiao, Technical Report 99-10, Computer Science Dept., Rensselaer Polytechnic Institute, Oct. 1999.

"Scalable algorithms for association mining", M.J. Zaki, IEEE Transactions on Knowledge and Data Engineering, 12(3), pp. 372-390, May-Jun. 2000.

"Integrating association rule mining with databases: alternatives and implications", S. Sarawagi, S. Thomas, R. Agrawal, ACM SIGMOD Intl. Conf. Management of Data, Jun. 1998.

"Data organization and access for efficient data mining", B. Dunkel, N. Soparkar, 15th IEEE Intl. Conf. on Data Engineering, Mar. 1999.

"Practical C++ Programming", Steve Oualline, O'Reilly & Associates, Inc., (Aug. 1995).

Web site print-out: SMILEY (Spatial Miner & Interface Language for Earth Yield), Database Systems Users & Research Group at NDSU (DataSURG) http://www.midas.cs.ndsu.nodak.edu/~smiley, 5 pgs., undated.

* cited by examiner

| BAND-1 | |
|---|---|
| 254 | 127 |
| (1111 1110) | (0111 1111) |
| 14 | 193 |
| (0000 1110) | (1100 0001) |

| BAND-2 | |
|---|---|
| 37 | 240 |
| (0010 0101) | (1111 0000) |
| 200 | 19 |
| (1100 1000) | (0001 0011) |

FIG. 1

BSQ format (2 files)

Band 1: 254 127 14 193
Band 2: 37 240 200 19

BIL format (1 file)

254 127 37 240
14 193 200 19

BIP format (1 file)

254 37 127 240
14 200 193 19 bSQ format (16 files)

| B11 | B12 | B13 | B14 | B15 | B16 | B17 | B18 | B21 | B22 | B23 | B24 | B25 | B26 | B27 | B28 |
|---|---|---|---|---|---|---|---|---|---|---|---|---|---|---|---|
| 1 | 1 | 1 | 1 | 1 | 1 | 1 | 0 | 0 | 0 | 1 | 0 | 0 | 1 | 0 | 1 |
| 0 | 1 | 1 | 1 | 1 | 1 | 1 | 1 | 1 | 1 | 1 | 1 | 0 | 0 | 0 | 0 |
| 0 | 0 | 0 | 0 | 1 | 1 | 1 | 0 | 1 | 1 | 0 | 0 | 1 | 0 | 0 | 0 |
| 1 | 1 | 0 | 0 | 0 | 0 | 0 | 1 | 0 | 0 | 0 | 1 | 0 | 0 | 1 | 1 |

```
                55                    depth=0   level=3
              / | \ \
             /   |  \___
            /  __|   \   \
          16  _8_   _15_   16         depth=1   level=2
             / /|\  /|\ \
            3 0 4 1  4 4 3 4          depth=2   level=1
            //|\    //|\   //|\
            1110    0010   1101       depth=3   level=0
```

FIG. 3

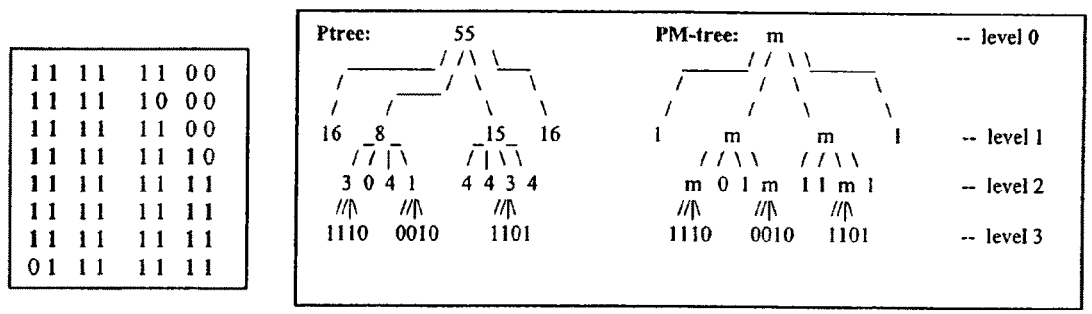
FIG. 6
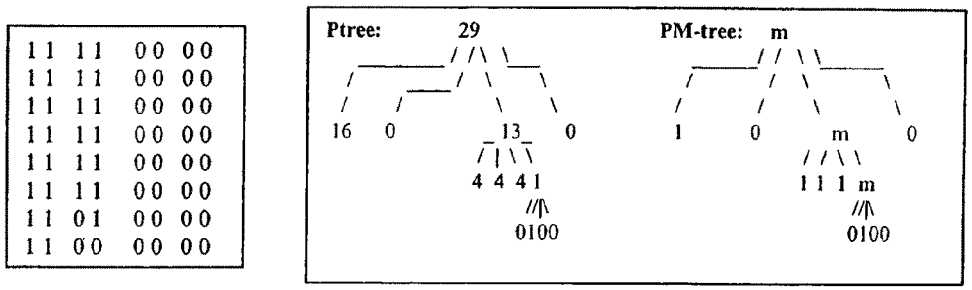
FIG. 7
FIG. 8

| 0 100 101 102 12 132 20 21 220 221 223 23 3 | & | 0 20 21 22 231 | → | RESULT |
| 0 | | 0 | → | 0 |
| 20 | | 20 | → | 20 |
| 21 | | 21 | → | 21 |
| 220 221 223 | | 22 | → | 220 221 223 |
| 23 | | 231 | → | 231 |

```
Ptree_ANDing(P1, P2, Presult)
// pos1, pos2, pos3 records the pure-1 quadrant path position of P1, P2, Presult
   1.  pos1:=0; pos2:=0; pos3:=0;
   2.  DO WHILE (pos1<>ENDofP1 and pos2<>ENDofP2)
          (a) IF P1.pos1=P2.pos2 THEN BEGIN
                  Presult.pos3:=P1.pos1;  pos1:=pos1+1;  pos2:=pos2+1;  pos3:=pos3+1;  END
          (b) ELSE IF P1.pos1 is the substring of P2.pos2 THEN BEGIN
                  Presult.pos3:=P2.pos2;  pos2:=pos2+1;  pos3:=pos3+1;  END
          (c) ELSE IF P2.pos2 is the substring of P1.pos1 THEN BEGIN
                  Presult.pos3:=P1.pos1;  pos1:=pos1+1;  pos3:=pos3+1;  END
          (d) ELSE IF P1.pos1<P2.pos2 THEN pos1:=pos1+1;
          (e) ELSE pos2:=pos2+1;
          END IF
      END DO
```

FIG. 11

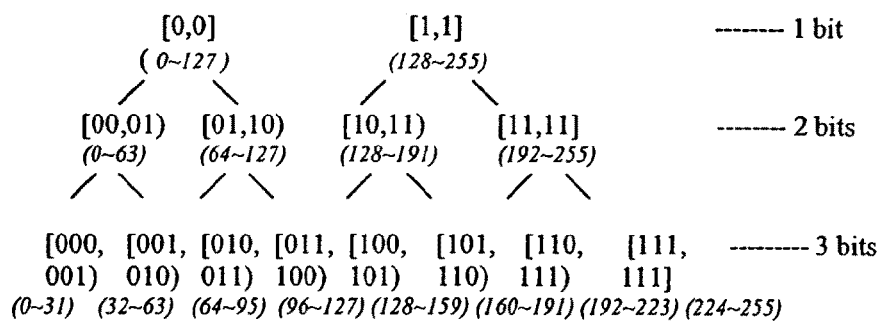

FIG. 12

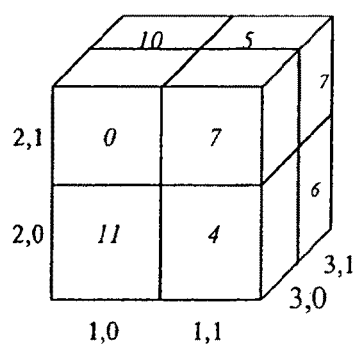

FIG. 13

```
Procedure P-ARM
{
    Data Partition;
    $F_1$ = {frequent 1-Itemsets};
    For (k=2; $F_{k-1} \neq \emptyset$) do begin
        $C_k$ = p-gen($F_{k-1}$);
        Forall candidate Itemsets c ∈ $C_k$ do
            c.count = AND_rootcount(c);
        $F_k$ = {c∈$C_k$ | c.count >= minsup}
        end
    Answer = $\cup k \, F_k$
}
```
FIG. 14
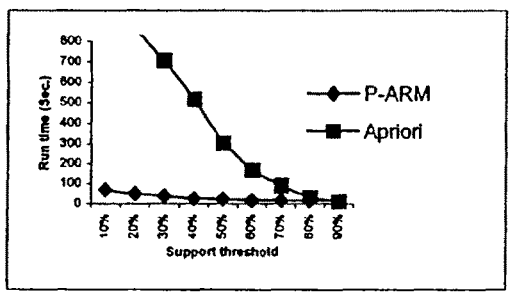
FIG. 15
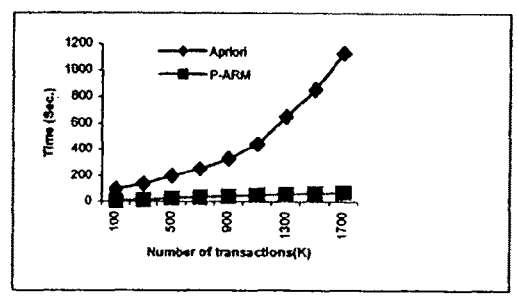
FIG. 16
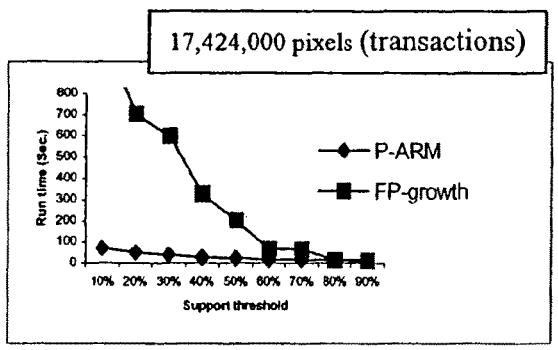
FIG. 17
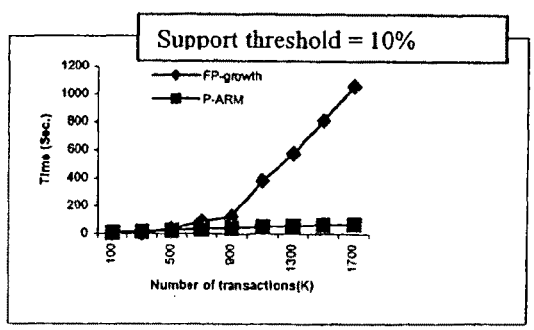
FIG. 18

```
FUNCTION LocalAND (Tree PeanoVectorTree1, Tree PeanoVectorTree2)
BEGIN
        unsigned long Result;
        Vector Mixed1, Mixed2;

Extract the Pure One Vector at the first level of each Tree and perform bit-wise
        AND operation on them.
        Find the total number of 1 bit in the resultant vector (let, n).
        Result = 4096 * n;

Extract the Pure Zero Vector at the first level from each tree and compliment
        them and perform bit-wise OR operation with the compliment of corresponding
        pure one vectors (let, the resultant vectors are Mixed1 and Mixed2)

For i = 1 to 64 do
        Begin
                If ith bit of Mixed1 is 0 then
                        move pointer for Tree2
                else if ith bit of Mixed2 is 0 then
                        Move pointer for Tree2
                else if ith bit of both Mixed1 and Mixed2 is 1
                        Extract the Pure One Vector at the second level of each Tree and
                        perform bit-wise AND operation on them.
                        Find the total number of 1 bit in the resultant vector (let, m).
                        Result = Result + 64 * m;
                        Extract the Pure Zero Vector at the second level from each tree, and take compliment of
                        them and perform bit-wise OR operation with the compliment of corresponding pure
                        one vectors (let, the resultant vectors are SecondMixed1 and SecondMixed2)
                        For j =1 to 64 do
                                If jth bit of Mixed1 is 0 then
                                        move pointer for Tree2
                                else if jth bit of Mixed2 is 0 then
                                        Move pointer for Tree2
                                else if ith bit of both Mixed1 and Mixed2 is 1
                                        Extract the pure one vector at the leaf level of
                                        each tree and perform bit-wise AND operation
                                        on them (let, the resultant vector is Pure)
                                        Find the number of 1 bit in Pure (let, l)
                                        Result = Result + l;
                        Endfor
        Endfor
END LocalAND
```

FIG. 20

SYSTEM AND METHOD FOR ORGANIZING, COMPRESSING AND STRUCTURING DATA FOR DATA MINING READINESS

CLAIM TO PRIORITY

The present application is a divisional of U.S. patent application Ser. No. 10/367,644, filed Feb. 14, 2003, now abandoned and entitled "System And Method For Organizing Compressing And Structuring Data For Data Mining Readiness, which is a Continuation-in-Part of U.S. patent application Ser. No. 09/957,637 (now U.S. Pat. No. 6,941,303), filed Sep. 20, 2001, and entitled "System and Method for Organizing, Compressing and Structuring Data for Data Mining Readiness," which claims priority to U.S. Provisional Patent Application No. 60/234,050, filed Sep. 20, 2000, and entitled "System and Method for Imagery Organization, Compression, and Data Mining" and to U.S. Provisional Patent Application No. 60/237,778, filed Oct. 4, 2000, and entitled "System and Method for Imagery Organization, Compression, and Data Mining," all of which are incorporated by reference herein in their entirety.

FEDERALLY SPONSORED RESEARCH

This invention was made with government support under Grant No. ACT#K96130308 awarded bu U.S. General Services Administration. The government has certain rights in the invention.

FIELD OF THE INVENTION

The present invention is related to the organization of large datasets existing in n-dimensional arrays and, more particularly, to the organization of the datasets into a bit-sequential format that facilitates the establishment of a lossless, data-mining-ready data structure.

BACKGROUND OF THE INVENTION

Data mining is the use of automated data analysis techniques to uncover previously undetected relationships among data items. The best known examples of data mining applications are in database marketing, wherein an analysis of the customer database, using techniques such as interactive querying, segmentation, and predictive modeling to select potential customers in a more precisely targeted way, in financial investment, wherein predictive modeling techniques are used to create trading models, select investments, and optimize portfolios, and in production manufacturing, wherein production processes are controlled and scheduled to maximize profit.

Data mining has been appropriate for these areas because, while significant amounts of data are present for analysis, the datasets are of a small enough nature that analysis can be performed quickly and efficiently using standard data mining techniques such as association rule mining (ARM), classification, and cluster analysis. This has not been the case with other data collection areas. For instance, such areas as bioinformatics, where analysis of microarray expression data for DNA is required, as nanotechnology where data fusion must be performed, as VLSI design, where circuits containing millions of transistors must be tested for accuracy, as spatial data, where data representative of detailed images can comprise millions of bits, and others present such extremely large datasets that mining implicit relationships among the data can be prohibitively time consuming with traditional methods.

The initial problem in establishing data mining techniques for these extremely large datasets is organizing the large amounts of data into an efficiently usable form that facilitates quick computer retrieval, interpretation, and sorting of the entire dataset or subset thereof. The organizational format of the data should take recognition of the fact that different bits of data can have different degrees of contribution to value, i.e., in some applications high-order bits along may provide the necessary information for data mining making the retention of all data unnecessary. The organizational format should also take recognition of the need to facilitate the representation of a precision hierarchy, i.e., a band may be well represented by a single bit or may require eight bits to be appropriately represented. As well, the organizational format need also take recognition of the need to facilitate the creation of an efficient, lossless data structure that is data-mining-ready, i.e., a data structure suited for data mining techniques.

SUMMARY OF THE INVENTION

The needs described above are in large part met by the system and method of the present invention. The data to be organized is preferably in the form of an n-dimensional array of binary data where the binary data is comprised of bits that are identified by a bit position within the n-dimensional array. The present invention, preferably implemented by a computer program executed on a high speed or parallel cluster of high speed computers, operates to create one file for each bit position of each attribute of the data while maintaining the bit position identification and to store the data with the corresponding bit position identification from the binary data within the created filed.

Once this bit-sequential format of the data is achieved, the formatted data can be structured into a tree format that is data-mining-ready. The formatted data is structured by dividing each of the files containing the binary data into quadrants according to the bit position identification and recording the count of 1-bits for each quadrant on a first level. Then, recursively dividing each of the quadrants into further quadrants and recording the count of 1-bits for each quadrant until all quadrants comprise a pure-1 quadrant or a pure-0 quadrant to form a basic tree structure. This structure is similar to other quadrant tree structures but for individual bit positions within values rather than the values themselves.

The basic tree structure may then be operated on with algebraic techniques and masking to produce other tree structures including value trees and tuple trees for use with various data mining techniques. The system and method of the present invention is especially suited to data mining of large datasets such as spatial datasets, bioinformatic datasets, nanotechnology datasets, and datasets representing integrated circuits.

BRIEF DESCRIPTION OF THE DRAWINGS

FIG. 1 is an illustrative example of a scene described by only two data bands having only two rows and two columns (both decimal and binary representations are shown).

FIG. 2 displays the BSQ, BIL, BIP and bSQ formats for the data of FIG. 1.

FIG. 3 depicts an 8-by-8 image and its corresponding PC-tree as developed by the present invention.

FIG. 6 depicts a hierarchical quadrant id scheme.

FIG. 7 presents the first operand to a PC-tree ANDing operation.

FIG. 8 presents the second operation to the PC-tree ANDing operation.

FIG. 11 is a listing of the pseudo code for performing the ANDing operation.

FIG. 12 is an example depiction of the value concept hierarchy of spatial data.

FIG. 13 is an example of a tuple count data cube using 1-bit values.

FIG. 14 is a listing of the pseudo code for an association rule mining technique, P-ARM, utilizing the bSQ and PC-tree technology of the present invention.

FIG. 15 provides a comparison graph of the P-ARM technique using PC-tree and Apriori for different support thresholds.

FIG. 16 provides a comparison of scalability between the P-ARM technique and the Apriori technique.

FIG. 17 provides a comparison graph of the P-ARM technique using PC-tree and FP-Growth for different support thresholds.

FIG. 18 provides a comparison of scalability between the P-ARM technique and the FP-Growth technique.

FIG. 19 is the pseudo-code listing for building a PV-tree.

FIG. 20 is the pseudo-code listing for the ANDing operation with PV-trees.

DETAILED DESCRIPTION OF THE PREFERRED EMBODIMENTS

Figure 4:
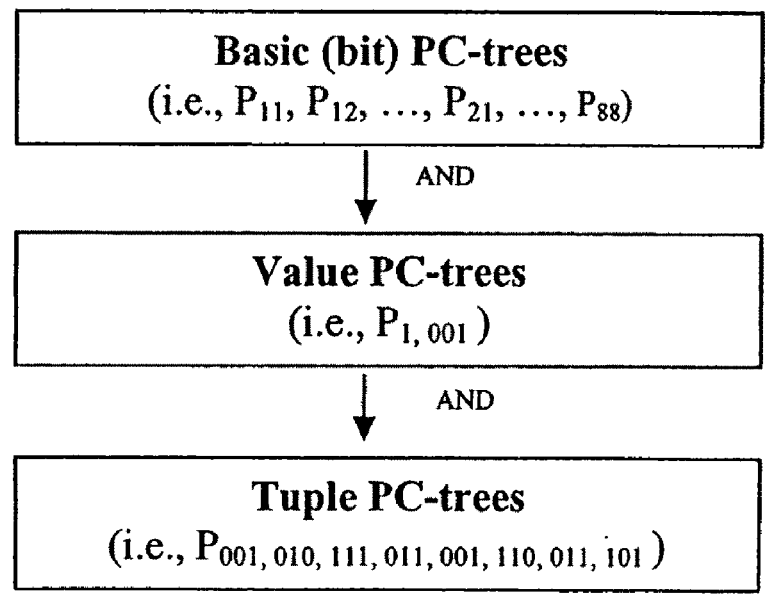
FIG. 4 is a flowchart depicting the transformation of basic PC-trees to value PC-trees (for 3-bit values) to tuple PC-trees.

The present invention is directed to a system and method for organizing large datasets existing in n-dimensional arrays into a data-mining-ready format comprising a bit-Sequential, or bSQ, format wherein a separate file for each bit position of each band is created, and to a system and method for structuring each bSQ file comprising Peano Count trees, or PC-trees, wherein quadrant-wise aggregate information, e.g., counts, for each bSQ file is recorded enabling various types of data mining to be performed very efficiently on an entire dataset or on a specific subset of data. The formatting, structuring, and various other operations of the present invention are preferably performed by clusters of high-speed computers.

Application areas for bSQ and PC-tree technology include but are not limited to precision agriculture, hazard detection and analysis (floods, fires, flora infestation, etc.), natural resource location and management, land management and planning, bioinformatics (genomics, transcripteomics, proteomics, metabileomics), nanotechnology, virtual artifact archiving, and VLSI design testing.

The present invention, including the bSQ format and PC-tree structures, will be described hereinbelow with reference to a particular type of dataset, a spatial dataset. However, it should be noted that the bSQ format and PC-tree structure can be applied to virtually any other type of dataset without departing from the spirit or scope of the invention.

I. Bit-Sequential Format of Spatial Data

With regard to the bit-sequential format of the present invention, a space is presumed to be represented by a 2-dimensional array of pixel locations. With each pixel is associated various attributes or data bands, such as visible reflectance intensities (blue, green, red), infrared reflectance intensities (e.g., near IR or NIR, middle IRs or MIR1 and MIR2, and thermal IR or TIR), and other value bands (e.g., yield quantities, quality measures, soil attributes and radar reflectance intensities). The raster-ordered pixel coordinates constitute the key attribute of the spatial dataset and the other bands are the non-key attributes. These spatial datasets are not usually organized in the relational format; instead, they are organized or can be easily reorganized into Band SeQuential or BSQ format (each attribute or band is stored as a separate file).

There are vast amounts of spatial data on which data mining can be performed to obtain useful information. However, this spatial data is collected in different ways and organized in different formats. The various prior art formats include BSQ, as mentioned above, BIL and BIP. The Band SeQuential (BSQ) format is similar to the Relational format. In BSQ each band is stored as a separate file. Each individual band uses the same raster order so that the primary key attribute values are calculable and need not be included. Landsat satellite Thematic Mapper (TM) scenes are in BSQ format. The Band Interleaved by Line (BIL) format stores the data in line-major order; the image scan line constitutes the organizing base. That is, BIL organizes all the bands in one file and interleaves them by row (the first row of all bands is followed by the second row of all bands, and so on). SPOT data, which comes from French satellite sensors, are in the Band Interleaved by Pixel (BIP) format, based on a pixel-consecutive scheme where the banded data is stored in pixel-major order. That is, BIP organizes all bands in one file and interleaves them by pixel. Standard TIFF images are in BIP format.

However, with the bit-sequential, bSQ, formatting of the present invention, eight separate files are created for each band. The eight separate files are based on the concept that reflectance values typically range from 0 to 255, represented by eight bits, thus there is one file created for each bit position. Comparison of the bSQ format against the prior art formats described above may be made with reference to FIGS. 1 and 2, wherein FIG. 1 provides an illustrative example of a scene described by only two data bands, each having four pixels, two rows, and two columns (both decimal and binary representations are shown), and FIG. 2 displays the BSQ, BIL, BIP and bSQ formats for the data. Within the bSQ format, file B11 includes the first bit position from each of the four pixels (represented in binary) in the first band, file B12 includes the second bit position from each of the four pixels in the first band, and so on.

There are several reasons to use the bSQ format. First, different bits have different degrees of contribution to the value. In some applications, not all bits are needed because high order bits may provide enough information. Second, the bSQ format facilitates the representation of a precision hierarchy. Third, and most importantly, bSQ format facilitates the creation of an efficient, rich data structure, the PC-tree (described in detail below), and accommodates technique pruning based on a one-bit-at-a-time approach.

II. Peano Count Trees (PC-Trees)

The present invention utilizes the established bSQ bit files to create a Peano Count tree, or PC-tree, structure. The PC-tree is a quadrant-based tree. The root of the PC-tree contains the 1-bit count of the entire bit-band. The next level of the tree contains the 1-bit counts of the four quadrants in raster order. At the next level, each quadrant is partitioned into sub-quadrants and their 1-bit counts in raster order constitute the children of the quadrant node. This construction is continued recursively down each tree path until the sub-quadrant is pure, i.e., entirely 1-bits or entirely 0-bits, which may or may not be at the leaf level (1-by-1 sub-quadrant).

To illustrate the PC-tree structure, reference is made to FIG. 3 where an 8-row-by-8-column image and its corresponding PC-tree is depicted. In this example, 55 is the count of 1's in the entire image, the numbers at the next level, 16, 8, 15, and 16, are the 1-bit counts for the four major quadrants. Since the first and last quadrants are made up of entirely 1-bits, sub-trees are not needed for these two quadrants (likewise for any pure 0 quadrants). This pattern is continued recursively using the Peano or Z-ordering of the four sub-quadrants at each new level. The process terminates at the "leaf" level (level-0) where each quadrant is a 1-row-1-column quadrant. If all sub-trees were expanded, including those for quadrants that are pure 1-bits, then the leaf sequence is just the Peano space-filling curve for the original raster image. Note that the fan-out of the PC-tree need not necessarily be 4. It can be any power of 4 (effectively skipping levels in the tree). Also, the fan-out at any one level need not coincide with the fan-out at another level. The fan-out pattern can be chosen to produce maximum compression for each bSQ file.

It should be noted that, for measurements that can be expected to exhibit reasonable spatial continuity, Hilbert ordering will produce even better compression than Peano. However, Hilbert ordering is a much less intuitive and a more complex ordering. By using Hilbert ordering instead of Peano, certain desirable mapping properties are lost. For that reason, Peano ordering is the preferred ordering. It should further be noted that the same general construction can be used for spatial data of more than 2-dimensions without departing from the spirit or scope of the invention. For instance, with 3-dimensional data, each level is partitioned into octants and so on.

Referring once again to 2-dimensional spatial data, it is clear that for each band (assuming 8-bit data values), 8 basic PC-trees may be created, one for each bit position. For band Bi, the basic PC-trees may be labeled as $P_{i,1}, P_{i,2}, \ldots, P_{i,8}$, thus, $P_{i,j}$ is a lossless representation of the $j^{th}$ bits of the values from the $i^{th}$ band. In addition, $P_{i,j}$ provides the 1-bit count for every quadrant of every dimension. These PC-tree's can be generated quite quickly and provide a "data mining ready", lossless format for storing spatial data.

The 8 basic PC-trees defined above can be combined using simple logical operations (AND, NOT, OR, COMPLEMENT) to produce PC-trees for the original values in a band (at any level of precision, 1-bit precision, 2-bit precision, etc., see the "value concept hierarchy" described below with reference to FIG. 12). $P_{b,v}$ is used to denote the Peano Count Tree, or the "value PC-tree", for band b, and value v, where v can be expressed in 1-bit, 2-bit, . . . , or 8-bit precision. For example, using the full 8-bit precision (all 8 bits) for values, $P_{b,11010011}$ can be constructed from the basic PC-trees by ANDing the basic PC-trees (for each 1-bit) and their complements (for each 0 bit):

$$PC_{b,11010011} = PC_{b1} \text{ AND } PC_{b2} \text{ AND } PC'_{b3} \text{ AND } PC_{b4} \text{ AND } \qquad \text{Eq. (1)}$$
$$PC'_{b5} \text{ AND } PC'_{b6} \text{ AND } PC'_{b7} \text{ AND } PC_{b8}$$

where ' indicates the bit-complement (which is simply the count complement in each quadrant). The AND operation is simply the pixel-wise AND of the bits.

From value PC-trees, tuple PC-trees may be constructed. The tuple PC-tree for tuple (v1, v2, . . . , vn), denoted $PC_{(v1, v2, \ldots, vn)}$, is:

$$PC_{(v1,v2,\ldots,vn)} = PC_{1,v1} \text{ AND } PC_{2,v2} \text{ AND } \ldots \text{ AND } PC_{n,vn}. \qquad \text{Eq. (2)}$$

where n is the total number of bands. See FIG. 4 for a flow-chart depicting the transformation of basic PC-trees to value PC-trees to Tuple PC-trees.

To show the advantage of utilizing PC-trees and Equation (1) above, it has been found that the process of converting the BSQ data for a TM satellite image (approximately 60 million pixels) to its basic PC-trees can be done in just a few seconds using a high performance PC computer via a one-time process. In doing so, the basic PC-trees are preferably stored in a "breadth-first" data structure, which specifies the pure-1 quadrants only. Using this data structure, each AND can be completed in a few milliseconds and the result counts can be computed easily once the AND and COMPLEMENT program has completed.

Figure 5:
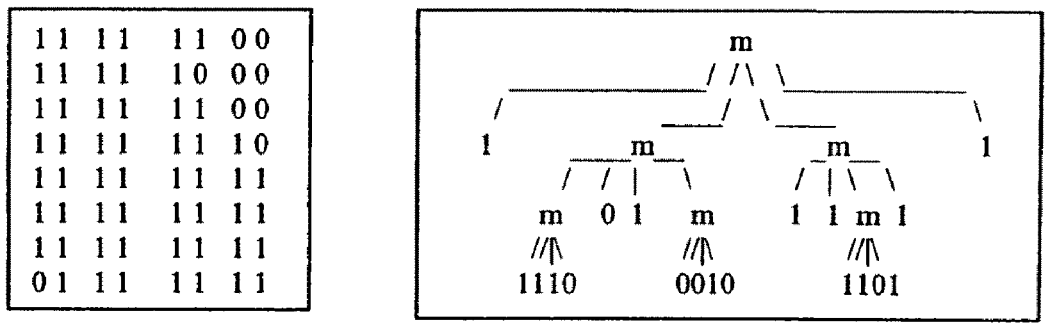
FIG. 5 depicts an 8-by-8 image and its corresponding PM-tree.

For efficient implementation, a variation of each basic PC-tree is constructed, its PM-tree (Pure Mask tree). In the PM-tree, a 3-value logic is used, in which 11 represents a quadrant of pure 1-bits (pure1 quadrant), 00 represents a quadrant of pure 0-bits (pure0 quadrant), and 01 represents a mixed quadrant. To simplify the exposition, 1 is used instead of 11 for pure1, 0 for pure0, and m for mixed. Starting with a bit-band, Bij, the PM-tree is first constructed and then 1-bits are counted from the bottom up to produce the PC-trees when necessary. For many situations, however, the PMT has all the information needed. Experience has shown that the PM-trees can be stored in a very compact form. Therefore, it is preferable to store only the basic PM-trees and then construct any needed data structure from those PM-trees. The PM-tree for the example of FIG. 3 may be found in FIG. 5.

The PM-tree is particularly useful for the ANDing operation between two PC-trees. The PM-tree specifies the location of the pure1 quadrants of the operands, so that the pure1 result quadrants can be easily identified by the coincidence of pure-1 quadrants in both operands and pure0 result quadrants occur wherever a pure-0 quadrant occurs on at least one of the operands.

For even more efficient implementation, other variations of basic PC-trees are constructed, called Peano Truth trees or PT-trees. PT-trees have 2-value logic at tree node, instead of a count as in PC-trees or 3-value logic as in PM-trees. In a PT-tree, the node value is 1 if the condition is true of that quadrant and 0 if it is false. For example, the Pure1 Peano Truth tree has a 1 bit at a tree node if the quadrant corresponding to that node is all 1's (pure1). There are Peano Truth trees for conditions; Pure1 (called the P1-tree), Pure0 (called the PZ-tree), "Not all Zeros" (PNZ-tree), and "Not all 1's" (called the PN1-tree). These are all lossless formats for the original data with minimum size. There are also "vector" forms of each Peano tree. The idea behind these vector forms is that each node of the tree contains a node-id or quadrant-id, e.g., Node$_{ij}$ and a 4-bit vector containing the truth values of its children nodes. Using this format, the subtree pointers can be eliminated in favor of a tabular representation. Also, since AND operation on bit vectors is the absolute fastest operation on in any computer's instruction set, the Ptree AND can be executed very rapidly on vector PT-trees. Finally, vector PT-trees can be distributed among the nodes of a parallel cluster of computers by simply sending to computer-ij, only those rows of the table with node-id ending in ij. Then each computer can compute only those quadrant counts for quadrants whose quadrant-id ends in ij and report that count to a control computer for summing. Any number of computers can be used. The more computers that are used in the AND computation, the faster it is accomplished. The scale-up is linear, since all computers are performing a similar computation in parallel.

To explain further, a detailed example of the ANDing operation is provided below.

ANDing Example

Figures 9, 10:
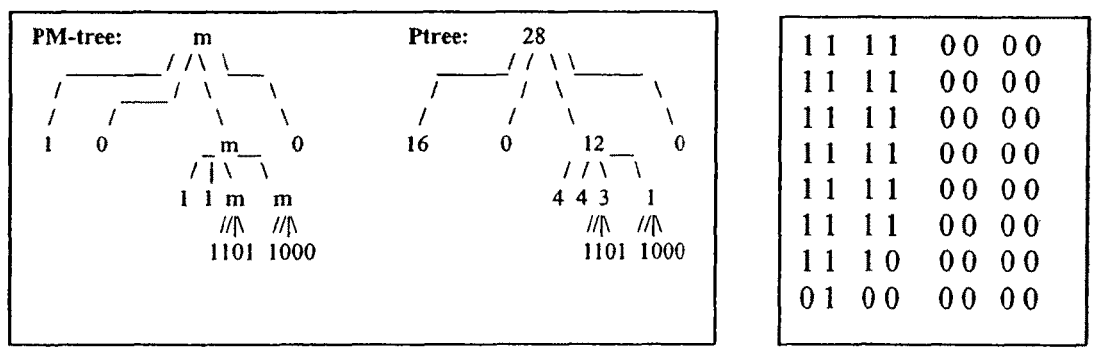
FIG. 9 is the output matching pure-1 sequence of the ANDing operation.
FIG. 10 is the result of ANDing the operands of FIG. 7 and FIG. 8.

The ANDing operation is used to calculate the root counts of value PC-trees and tuple PC-trees. Preferably, only the basic PC-trees are stored and the value and tuple PC-trees are generated on an as-needed basis. In this operation, it is presumed that the basic PC-trees are coded in a compact, depth-first ordering of the path to each pure-1 quadrant. A hierarchical quadrant id (qid) scheme is then used. At each level a subquadrant id number (0 means upper left, 1 means upper right, 2 means lower left, 3 means lower right) is appended, see FIG. 6 for quadrant id. Using the PC-tree of FIG. 7 as the first operand of the AND, it can be seen that the sequence of pure-1 qids (left-to-right depth-first order) is 0, 100, 101, 102, 12, 132, 20, 21, 220, 221, 223, 23, 3. Using the PC-tree of FIG. 8 as the second operand of the AND, it can be seen that the sequence of pure-1 qids is 0, 20, 21, 22, 231. Since a quadrant will be pure 1's in the result only if it is pure-1's in both operands (or all operands, in the case there are more than 2), the AND is done by the following: scan the operands; output matching pure-1 sequence, see FIG. 9. The result of the AND operation is shown in FIG. 10. The pseudo-code for the ANDing operation is provided in FIG. 11.

It should be noted that other algebraic operations, i.e., pixel-by-pixel logical operations, may easily be performed on PC-trees as needed including OR, NOT, and XOR. The NOT operation is a straightforward translation of each count to its quadrant-complement (e.g., a 5 count for a quadrant of 16 pixels has a complement of 11). The OR operation is identical to the AND operation except that the role of the 1-bits and the 0-bits are reversed.

III. Tuple Count Data Cube (TC-Cube)

For most spatial data mining procedures the root counts of the tuple PC-trees, as described above and determined by Equation (3) below, are precisely the needed input numbers, since they are the occurrence frequencies of the tuples over the space in question.

$$PC_{(v1,v2...,vn)} = PC_{1,v1} \text{ AND } PC_{2,v2} \text{ AND } \ldots \text{ AND } PC_{n,vn},$$ Eq. (3)

These root counts can be organized into a data cube that is preferably called a Tuple Count cube, or TC-cube of the spatial dataset. The TC-cube cell located at $(v_1, v_2, \ldots, v_n)$, contains the root count of $P_{(v1,v2,\ldots,vn)}$. For example, assuming just 3 bands, the $(v_1, v_2, v_3)^{th}$ cell of the TC-cube contains the root count of $P_{(v1,v2,v3)} = P_{1,v1}$ AND $P_{2,v2}$ AND $P_{3,v3}$. The cube can be contracted or expanded by going up one level or down one level in the value concept hierarchy to half or double in each dimension. With bSQ format, the value concept hierarchy of spatial data can be easily represented. For example, refer to FIG. 12 where, for band n, 1 bit up to 8 bits can be used to represent reflectances. FIG. 13 provides an example of a TC-cube using 1-bit values. Note that the total count in the TC-cube is the total number of pixels (e.g., 64 in FIG. 13).

IV. PC-Tree Implementation

The operations to format data into bSQ format and create PC-trees are preferably performed by a parallel cluster of high-speed computers. An example of how PC-trees may be implemented using a such a parallel cluster of computers, e.g., 16 or any other appropriate number, to obtain a root count of a PC-tree assuming a dataset R(K1, . . , Km, A1, . . . , An) where Ki's are structure attributes (e.g., K1=X coord, K2=Y-coord. in a 2-D image) and Ai's are feature attribute which quantifies a feature of a structure point (e.g., pixel), is provided below.

First, it is assumed that all feature attribute values are one byte (8 bits), although any other number of bits may be used without departing from the spirit or scope of the invention. Next, for clarity of exposition it is assumed that R(X, Y, A1, . . . , An) and x=x1x2 . . xp, y=y1y2 . . yp as bit strings. Then the quadrant identifier (qid) of the pixel (x,y) is x1y1.x2y2 . . . . xpyp (e.g., if (x,y)=(100111, 001010), qid=10.00.01.10.11.10). Two vector PC-trees are preferably used, the Peano Not-Zero, PNZV, form which shows a 1-bit at a pixel quadrant iff the quadrant is not pure zeros, and the Peano Pure-1, P1V, form which shows a 1-bit iff the quadrant is pure ones.

Striping (distributing to nodes) data tuples as they arrive to the system is preferably performed as follows: 1. Broadcast tuple to all nodes (eg, on Ethernet, broadcast cost=unicast cost); and 2. Node-jk compares each qid segment, except the leaf level, to jk. For every match, xiyi=jk, Node-jk ORs each bit of (a1, . . . , an) as a bit string into PNZV[ . . . xiyi] and ANDs each bit of (a1, . . . , an) into P1V[ . . . xiyi] at position, x(i+1)y(i+1).

Then, to obtain a root count of a PC-tree, a root count request is broadcast to all nodes. For example, a request in the format of (Ptree, RootNode, Masktree) is broadcast where:

A. "Ptree" identifies the dataset (R(X, Y, A1, . . . , An) and the Ptree:
BasicPtree Pbp
RectanglePtree P(,,[v1,vu], . . . ,[w1,wu],[xu,x1]) which includes IntervalPtree P(,,[v1,vu]) which includes ValuePtree P(,,v)=P(,,[v,v])) MultiValuePtree P(,,vi, . . . ,vj)=P(,,[vi,vi], . . . ,[vj,vj]) which includes TuplePtree P(v1, . . . ,vn).

B. RootNode is the root of a subtree (subquad) given as a qid [ab . . . cd].

C. MaskTree has ones only at selected positions (to mask out particular pixels for special purposes. It will be ignored below).

For ease of exposition, it is assumed that the Ptree requested is a tuple Ptree with a feature attribute bit-precision of q-bits. The Ptree can be fully specified by a request: (q, (101 . . 0, 001 . . 0, . . . , 110 . . 1)) with a bit string of length q for each band, A1, . . . , An). Each 1-bit request the basic Ptree and each 0-bit requests the complement of the basic Ptree. E.g., for q=2 and P(10, 11, . . . , 01)=P(2, 3, . . . , 1) send (q, (10, 11, . . . , 01)).

Then, each Nodeij (a computer may be acting as several nodes, starting an independent execution thread for each node that it represents) performs as follows:

For each qid in its directory ending in ij, [ . . ij]=[ab . . cd . . hk . ij], compute P1V=P1V(11)&PNZV(12) & P1V (21)& P1V(22) & . . . & PNZV(n1)&P1Vn2) PNZV=PNZV (11)& P1V(12) & PNZV(21)&PNZV(22) & . . . & P1V(n1)& PNZVn2)

Next, compose a "ChildVector" (CV[ . . ij]): initially 11 . . 1, AND in PNZV (zeros out positions corresponding to pure0 quads), XOR in P1V (flips Pure1's from 1 to 0, leaving only Mixed quads at 1).

Next, calculate COUNT[ . . ij]=(4^level)*OneCount(P1V). Add [ . . . ij . . . qr]-Children counts to COUNT[ . . ij] as they arrive. When all children have replied (there are OneCount (CV[ . . . ij]) of them) Unicast COUNT[ab . . cd . . hk . ij] to ParentNode, Node(hk) by setting up a unicast socket to parent. This continues until node(cd) gets its answer. Node(cd) then forwards to NodeC.

The method by which requests are sent to the nodes of the cluster and replies are accumulated into the final count will vary depending on the type and size of the datasets and the type and number of computers available as nodes in the cluster. The options include 1) broadcast request, 2) serial multicast request, 3) parallel unicast reply, 4) serial unicast reply.

V. Data Mining Techniques Utilizing bSQ and PC-tree Technology

Various data mining techniques wherein the bSQ and PC-tree technology of the present invention are utilized are described below. However, it should be noted that numerous other types of data mining techniques may employ the bSQ and PC-tree technology without departing from the spirit or scope of the invention. Any data mining technique based on counts of occurrences of feature values, benefits from this technique.

The three categories of data mining techniques are Association Rule Mining (ARM), Classification and Clustering.

V. A. Association Rule Mining

The task of association rule mining (ARM) is to find interesting relationships from the data in the form of rules. The initial application of association rule mining was on market basket data. An association rule is a relationship of the form X=>Y, where X and Y are sets of items. X is called antecedent and Y is called the consequence. There are two primary measures, support and confidence, used in assessing the quality of the rules. The goal of association rule mining is to find all the rules with support and confidence exceeding user specified thresholds. The first step in a basic ARM technique (e.g., Apriori and DHP) is to find all frequent itemsets whose supports are above the minimal threshold. The second step is to derive high confidence rules supported by those frequent itemsets. The first step is the key issue in terms of efficiency.

The formal definition of association rules is introduced in "Mining Association Rules in Large Database" by R. Agrawal, T. Imielinski, A. Swami (SIGMOD 1993), which is hereby incorporated by reference. Let I=$\{i_1, i_2, \ldots, i_m\}$ be a set of literals, called items. Let D be a set of transactions, where each transaction T is a set of items (called "itemset") such that T⊆I. A transaction T contains X, a set of some items in I, if X⊆T. An association rule is an implication of the form X=>Y, where X⊂I, Y⊂I, and X∩Y=∅. The rule X=>Y holds in the transaction set D with confidence c if c % of transactions in D that contain X also contain Y. The rule X=>Y has support s in the transaction set D if s % of transactions in D contain X∪Y.

Given a set of transactions D, the problem of mining association rules is to generate all association rules that have certain user-specified minimum support (called minsup) and confidence (called minconf).

The discovery of association rules is usually performed in two steps. The first step is to find all itemsets whose support is greater than the user-specified minimum support. Itemsets with minimum support are called frequent itemsets. The second step is to generate the desired rules using the frequent itemsets generated in the first step. The overall performance is mainly determined by the first step. Once the frequent itemsets have been generated, it is straightforward to derive the rules.

Basic association rule mining techniques are proposed for dealing with Boolean attributes, such as Market Basket data. To perform association rule mining on spatial, remotely sensed image, or RSI data, data partition is required since RSI data are quantitative data. There are various kinds of partition approaches, including Equi-length partition, Equi-depth partition and user customized partition.

As mentioned above, frequent itemset generation is the key step in association rule mining. Usually a step-wise procedure is used to generate frequent itemsets. To determine if a candidate itemset is frequent, the support is calculated then compared to the threshold. In Apriori, a well known data mining technique, and most other ARM techniques, the entire transaction database needs to be scanned to calculate the support for each candidate itemset. When the transaction set is large, (e.g., a large image with 40,000,000 pixels), this cost will be extremely high.

Utilizing the bSQ and PC-tree technology of the present invention, a new data mining technique, preferably called P-ARM, can be used to solve this problem. The main idea is that support of each candidate itemset can be obtained directly from ANDing Ptrees (as the root count of the result). There is no need to scan the transaction database, which is the main cost for standard ARM methods.

The P-ARM technique is provided in FIG. 14. The p-gen function in P-ARM differs from the Apriori-gen function in Apriori in the way pruning is done. Since any itemsets consisting of two or more intervals from the same band will have zero support (no value can be in both intervals simultaneously), the kind of joining done in A prior is unnecessary. The AND_rootcount function is used to calculate itemset counts directly by ANDing the appropriate basic-Ptrees. For example, in the itemset {B1[0,64), B2[64,127)}, where B1 and B2 are two bands, the support count is the root count of $P_{1,00}$ AND $P_{2,01}$.

The P-ARM technique is applicable equally to any kind of data partition. Since whether partitioning is equi-length, equi-depth or user-defined, it can be characterized as follows. For each band, choose partition-points, $v_0=0, v_1, \ldots, v_{n+1}=256$, then the partitions are, $\{[v_i, v_{i+1}): i=0..n\}$ and are identified as values, $\{v: i=0..n\}$. The items to be used in the data mining techniques are then pairs, $(b_i, v_j)$.

To show the usefulness of the P-ARM technique, which utilizes the bSQ and PC-tree technology of the present invention, the P-ARM technique is compared to the classical frequent itemsets generation technique, Apriori, and a recently proposed efficient technique, FP-growth, in which no candidate generation step is needed. The FP-Growth technique is described in "Mining Frequent Patterns without Candidate Generation" by J. Han, J. Pei, and Y. Yin (SIGMOD 2000), which is hereby incorporated by reference. The comparisons are made based on experiments performed on a 900-MHz PC with 256 megabytes main memory, running Windows 2000.

The P-ARM technique was generalized to find all the frequent itemsets, not limited to those of-interest (e.g., containing Yield), for the fairness. The images used were actual aerial TIFF images with a synchronized yield band. Thus, each dataset has 4 bands {Blue, Green, Red, Yield}. Different image sizes are used up to 1320×1320 pixels (the total number of transactions will be ~1,700,000). Only the basic PC-trees are stored for each dataset.

The Apriori technique for the TIFF-Yield datasets was implemented using equi-length partitioning. P-ARM is more scalable than Apriori in two ways. First, P-ARM is more scalable for lower support thresholds. The reason is, for low support thresholds, the number of candidate itemsets will be extremely large. Thus, candidate itemset generation performance degrades markedly. FIG. 15 gives the results of the comparison of the P-ARM technique using PC-tree and Apriori for different support thresholds.

Secondly, the P-ARM technique is more scalable to large image datasets. The reason is, in the Apriori technique the entire database must be scanned each time a support is to be calculated. This is a very high cost for large databases. However, in P-ARM, since the count is calculated directly from the root count of a basic-PC-tree AND program, when the dataset size is doubled, only one more level is added to each basic-PC-tree. The cost is relatively small compared to the Apriori technique as shown in FIG. 16.

FP-growth is a very efficient technique for association rule mining, which uses a data structure called frequent pattern tree (FP-tree) to store compressed information about frequent patterns. The FP-growth object code was used and converted the image to the required file format. For a dataset of 100 K bytes, FP-growth runs very fast. But the FP-growth technique is run on the TIFF image of size 1320×1320 pixels, the performance falls off. For large sized datasets and low support thresholds, it takes longer for FP-growth to run than P-ARM. FIG. 17 shows the experimental result of running the P-ARM and the FP-growth techniques on a 1320×1320 pixel TIFF dataset. In these experiments, 2-bit precision has been used.

Both P-ARM and FP-growth run faster than Apriori. For large image datasets, the P-ARM technique runs faster than the FP-tree technique when the support threshold is low. Also, the relative performance of P-ARM (relative to FP-growth) increases as the size of the data set increases, see FIG. 18.

Partitioning and Pruning with P-ARM

Pruning techniques, such as bit-based pruning and band-based pruning, are important to the efficiency of association rule mining. Partitioning techniques, such as equi-length partitioning, equi-depth partitioning, and customized partitioning can be used in addition or as an alternative to pruning, to reduce the complexity of spatial data. Specifically, when dealing with quantitative data, such as reflectance values (which are typically 8-bit data values), it is common to partition the data before performing association rule mining. As mentioned earlier, there are several ways to partition the data, including equi-length partitioning, equi-depth partitioning and customized partitioning. Equi-length partition is a simple but very useful method. By truncating some of the right-most bits of the values (low order or least significant bits) the size of the itemset can be dramatically reduced without losing too much information (the low order bits show only subtle differences). For example, the right-most 6-bits can be truncated, resulting in the set of values {00, 01, 10, 11} (in decimal, {0, 1, 2, 3}). Each of these values represents a partition of the original 8-bit value space (i.e., 00 represents the values in [0,64), 01 represents the values in [64,128), etc.).

Further pruning can be done by understanding the kinds of rules that are of interest to the user and focusing on those only. For instance, for an agricultural producer using precision techniques, there is little interest in rules of the type, Red>48→Green<134. A scientist might be interested in color relationships (both antecedent and consequent from color bands), but the producer is interested only in relationships in color antecedent and consequents from, for example, a yield band (i.e., when do observed color combinations predict high yield or foretell low yield). Therefore, for precision agriculture applications and other similar type applications, it makes sense to restrict to those rules that have consequent from the yield band. The restrictions in the type of itemsets allowed for antecedent and consequent based on interest will be referred to as of interest, as distinct from the notion of rules that are "interesting". Of-interest rules can be interesting or not interesting, depending on such measures as support and confidence, etc. In some cases, it would be better to allow users to partition the value space into uneven partitions. User knowledge can be applied in partitioning. E.g., band $B_i$ can be partitioned into {[0,32), [32,64) [64,96), [96,256)}, if it is known that there will be only a few values between 96 to 255. Applying user's domain knowledge increases accuracy and data mining efficiency. This type of partitioning will be referred to as user-defined partitioning. Equi-depth partitioning (each partition has approximately the same number of pixels) can be done by setting the endpoints so that there are approximately the same number of values in each partition.

Whether partitioning is equi-length, equi-depth or user-defined, it can be characterized as follows. For each band, choose partition-points, $v_0=0, v_1, \ldots, v_{n+1}=256$, then the partitions are, $\{[v_i, v_{i+1}): i=0 \ldots n\}$ and are identified as values, $\{v_i: i=0 \ldots n\}$. The items to be used in the data mining techniques are then pairs, $(b_i, v_j)$. The details of association rule mining for remotely sensed images (RSI) with the P-ARM technique wherein partitioning and pruning is used is provided below.

P-ARM Details for RSI Data Utilizing Partitioning and Pruning

Let I be the set of all items and T be the set of all transactions. I={(b,v)|b=band, v=value (1-bit or 2-bit or ... 8-bit)}, T={pixels}.

Admissible Itemsets (Asets) are itemsets of the form, $Int_1 \times Int_2 \times \ldots \times Int_n = \pi_{i=1 \ldots n} Int_i$, where $Int_i$ is an interval of values in $Band_i$ (some of which may be the full value range). Modeled on the Apriori technique [2], all itemsets which are frequent and of-interest (e.g., if $B_1$=Yield), the user may wish to restrict attention to those Asets for which $Int_1$ is not all of $B_1$—so either high-yield or low-yield are found first. For 1-bit data values, this means either yield<128 or Yield≧128 (other threshold values can be selected using the user-defined partitioning concept described above). Then, the user may want to restrict interest to those rules for which the rule consequent is $Int_1$.

For a frequent Aset, $B=\pi_{i=1 \ldots n} Int_i$, rules are created by partitioning {1 .. n} into two disjoint sets, $\hat{A}=\{i_1 \ldots i_m\}$ and $\hat{C}=\{j_1 \ldots j_q\}$, q+m=n, and then forming the rule, A→C where $A=\pi_{k \in \hat{A}} Int_k$ and $C=\pi_{k \in \hat{C}} Int_k$. As noted above, users may be interested only in rules where q=1 and, therefore, the consequents come from a specified band (e.g., $B_1$=Yield). Then, there is just one rule of interest for each frequent set found and it need only be checked as to whether it is high-confidence or not.

For the restricted interest case described above, in which q=1 and C=$Int_1$ (e.g., the Yield band), support{A→C}=support{p|p is a pixel such that p(i) is in all $Int_i$, i=1 .. n}. The confidence of a rule, A→C is its support divided by the support of A. In the restricted interest case, with $B_1$=Yield, $B_2$=blue, $B_3$=green, $B_4$=red, it is necessary to calculate support (ARC)=support($Int_1 \times Int_2 \times Int_3 \times Int_4$) and support(A)=support($Int_2 \times Int_3 \times Int_4$). If support(B)≧minsup (the specified minimum support threshold) and supp(B)/supp (A)≧minconf (the specified minimum confidence threshold), then A→B is a strong rule. A k-band Aset (kAset) is an Aset in which k of the $Int_i$ intervals are non-full (i.e., in k of the bands the intervals are not the fully unrestricted intervals of all values).

Finding all frequent 1Asets is performed first. Then, the candidate 2Asets are those whose every 1Aset subset is frequent, etc. The candidate kAsets are those whose every (k−1) Aset subset is frequent. Next, a pruning technique based on the value concept hierarchy is looked for. Once all 1-bit frequent kAsets are found, the fact that a 2-bit kAset cannot be frequent if its enclosing 1-bit kAset is infrequent can be used. A 1-bit Aset encloses a 2-bit Aset if when the endpoints of the 2-bit Aset are shifted right 1-bit position, it is a subset of the 1-bit Aset, (e.g., [1,1] encloses [10,11], [10,10] and [11,11]).

The P-ARM technique assumes a fixed value precision, for example, 3-bit precision in all bands. The p-gen function differs from the Apriori-gen function in the way pruning is done. In this example, band-based pruning is used. Since any itemsets consisting of two or more intervals from the same band will have zero support (no value can be in both intervals simultaneously), the kind of joining done in [1] is not necessary. The AND_rootcount function is used to calculate Aset counts directly by ANDing the appropriate basic P-trees instead of scanning the transaction databases. For example, in the Asets, {B1[0,64), B2[64,127)}, the count is the root count of $P_{1,00}$ AND $P_{2,01}$.

To obtain the rules at other precision levels, the P-ARM technique can be applied again. There is a special bit-based pruning technique which can be applied in this case. This bit-based pruning is essentially a matter of noting, e.g., if Aset $[1,1]_2$ (the interval [1,1] in band 2) is not frequent, then the Asets $[10,10]_2$ and $[11,11]_2$ which are covered by $[1,1]_2$ cannot possibly be frequent either.

P-ARM Example Utilizing Partitioning and Pruning

The following data in relational format will be used to illustrate the method. The data contains four bands with 4-bit precision in the data values.

| FIELD COORDS | CLASS LABEL | REMOTELY SENSED REFLECTANCES | | |
|---|---|---|---|---|
| X, Y | YIELD | Blue | Green | Red |
| 0, 0 | 3 | 7 | 8 | 11 |
| 0, 1 | 3 | 3 | 8 | 15 |
| 0, 2 | 7 | 3 | 4 | 11 |
| 0, 3 | 7 | 2 | 5 | 11 |
| 1, 0 | 3 | 7 | 8 | 11 |
| 1, 1 | 3 | 3 | 8 | 11 |
| 1, 2 | 7 | 3 | 4 | 11 |
| 1, 3 | 7 | 2 | 5 | 11 |
| 2, 0 | 2 | 11 | 8 | 15 |
| 2, 1 | 2 | 11 | 8 | 15 |
| 2, 2 | 10 | 10 | 4 | 11 |
| 2, 3 | 15 | 10 | 4 | 11 |
| 3, 0 | 2 | 11 | 8 | 15 |
| 3, 1 | 10 | 11 | 8 | 15 |
| 3, 2 | 15 | 10 | 4 | 11 |
| 3, 3 | 15 | 10 | 4 | 11 |

| FIELD COORDS | CLASS LABEL | REMOTELY SENSED REFLECTANCES | | |
|---|---|---|---|---|
| X, Y | YIELD | Blue | Green | Red |
| 0, 0 | 0011 | 0111 | 1000 | 1011 |
| 0, 1 | 0011 | 0011 | 1000 | 1111 |
| 0, 2 | 0111 | 0011 | 0100 | 1011 |
| 0, 3 | 0111 | 0010 | 0101 | 1011 |
| 1, 0 | 0011 | 0111 | 1000 | 1011 |
| 1, 1 | 0011 | 0011 | 1000 | 1011 |
| 1, 2 | 0111 | 0011 | 0100 | 1011 |
| 1, 3 | 0111 | 0010 | 0101 | 1011 |
| 2, 0 | 0010 | 1011 | 1000 | 1111 |
| 2, 1 | 0010 | 1011 | 1000 | 1111 |
| 2, 2 | 1010 | 1010 | 0100 | 1011 |
| 2, 3 | 1111 | 1010 | 0100 | 1011 |
| 3, 0 | 0010 | 1011 | 1000 | 1111 |
| 3, 1 | 1010 | 1011 | 1000 | 1111 |
| 3, 2 | 1111 | 1010 | 0100 | 1011 |
| 3, 3 | 1111 | 1010 | 0101 | 1011 |

The data is first converted to bSQ format. We display the bSQ bit-band values in their spatial positions, rather than in columnar files. The $Band_1$ bit-bands are:

| $B_{11}$ | $B_{12}$ | $B_{13}$ | $B_{14}$ |
|---|---|---|---|
| 0000 | 0011 | 1111 | 1111 |
| 0000 | 0011 | 1111 | 1111 |
| 0011 | 0001 | 1111 | 0001 |
| 0111 | 0011 | 1111 | 0011 |

The Band-1 basic Ptrees are as follows (tree pointers are omitted). The Band 2, 3 and 4 Ptrees are similar.

| $P_{1,1}$ | $P_{1,2}$ | $P_{1,3}$ | $P_{1,4}$ |
|---|---|---|---|
| 5 | 7 | 16 | 11 |
| 0 0 1 4 | 0 4 0 3 | | 4 4 0 3 |
| 0001 | 0111 | | 0111 |

The value Ptrees are created as needed. The creation process for $P_{1,0011}$ is shown as an example.

| $P_{1,0011}$ = | $P_{1,1}'$ AND | $P_{1,2}'$ AND | $P_{1,3}$ AND | $P_{1,4}$ |
|---|---|---|---|---|
| 4 | 11 | 9 | 16 | 11 |
| 4 0 0 0 | 4 4 3 0 | 4 0 4 1 | | 4 4 0 3 |
| | 1110 | 1000 | | 0111 | since,
0 1 20 21 22     (pure-1 paths of $P_{1,1}'$)
0   2    31     (pure-1 paths of $P_{1,2}'$)
0 1     31 32 33     (pure-1 paths of $P_{1,4}$ note that $P_{1,3}$ is entirely pure-1)
0     (pure-1 paths of $P_{1,0011}$ 0 is the only pure-1 path in all operands)

The other value Ptrees are calculated in this same way.

| $P_{1,0000}$ | $P_{1,0100}$ | $P_{1,1000}$ | $P_{1,1100}$ | $P_{1,0010}$ | $P_{1,0110}$ | $P_{1,1010}$ | $P_{1,1110}$ |
|---|---|---|---|---|---|---|---|
| 0 | 0 | 0 | 0 | 3<br>0 0 3 0<br>1110 | 0 | 2<br>0 0 1 1<br>0001 1000 | 0 |
| $P_{1,0001}$ | $P_{1,0101}$ | $P_{1,1001}$ | $P_{1,1101}$ | $P_{1,0011}$ | $P_{1,0111}$ | $P_{1,1011}$ | $P_{1,1111}$ |
| 0 | 0 | 0 | 0 | 4<br>4 0 0 0 | 4<br>0 4 0 0 | 0 | 3<br>0 0 0 3<br>0111 |

| $P_{2,0000}$ | $P_{2,0100}$ | $P_{2,1000}$ | $P_{2,1100}$ | $P_{2,0010}$ | $P_{2,0110}$ | $P_{2,1010}$ | $P_{2,1110}$ |
|---|---|---|---|---|---|---|---|
| 0 | 0 | 0 | 0 | 2<br>0 2 0 0<br>0101 | 0 | 4<br>0 0 0 4 | 0 |
| $P_{2,0001}$ | $P_{2,0101}$ | $P_{2,1001}$ | $P_{2,1101}$ | $P_{2,0011}$ | $P_{2,0111}$ | $P_{2,1011}$ | $P_{2,1111}$ |
| 0 | 0 | 0 | 0 | 4<br>2 2 0 0<br>0101 1010 | 2<br>2 0 0 0<br>1010 | 4<br>0 0 4 0 | 0 |

| $P_{3,0000}$ | $P_{3,0100}$ | $P_{3,1000}$ | $P_{3,1100}$ | $P_{3,0010}$ | $P_{3,0110}$ | $P_{3,1010}$ | $P_{3,1110}$ |
|---|---|---|---|---|---|---|---|
| 0 | 6<br>0 2 0 4<br>1010 | 8<br>4 0 4 0 | 0 | 0 | 0 | 0 | 0 |
| $P_{3,0001}$ | $P_{3,0101}$ | $P_{3,1001}$ | $P_{3,1101}$ | $P_{3,0011}$ | $P_{3,0111}$ | $P_{3,1011}$ | $P_{3,1111}$ |
| 0 | 2<br>0 2 0 0<br>0101 | 0 | 0 | 0 | 0 | 0 | 0 |

| $P_{4,0000}$ | $P_{4,0100}$ | $P_{4,1000}$ | $P_{4,1100}$ | $P_{4,0010}$ | $P_{4,0110}$ | $P_{4,1010}$ | $P_{4,1110}$ |
|---|---|---|---|---|---|---|---|
| 0 | 0 | 0 | 0 | 0 | 0 | 0 | 0 |
| $P_{4,0001}$ | $P_{4,0101}$ | $P_{4,1001}$ | $P_{4,1101}$ | $P_{4,0011}$ | $P_{4,0111}$ | $P_{4,1011}$ | $P_{4,1111}$ |
| 0 | 0 | 0 | 0 | 0 | 0 | 11<br>3 4 0 4<br>1011 | 5<br>1 0 4 0<br>0100 |

Assume the minimum support is 60% (requiring a count of 10) and the minimum confidence is 60%. First, we find all 1Asets for 1-bit values from $B_1$. There are two possibilities for $Int_1$, [1,1] and [0,0].

Since, $P_{1,1}$ support$([1,1]_1)$=5 (infrequent) and support$([0,0]_1)$=11 (frequent).

5
0014
0001

Similarly, there are two possibilities for $Int_2$ with support $([1,1]_2)$=8 (infrequent) and support$([0,0]_2)$=8 (infrequent), two possibilities for $Int_3$ with support$([1,1]_3)$=8 (infrequent) and support$([0,0]_3)$=8 (infrequent), and two possibilities for $Int_3$ with support$([1,1]_4)$=16 (frequent) and support$([0,0]_4)$=0 (infrequent).

The set of 1-bit frequent 1Asets, 1L1, is $\{[0,0]_1, [1,1]_4\}$

The set of 1-bit candidate 2Asets, 1C2, is $\{[0,0]_1 \times [1,1]_4\}$ (support=root-count $P_{1,0}$ & $P_{4,1}$=11) and therefore, 1L2=$\{[0,0]_1 \times [1,1]_4\}$ The set of 1-bit candidate 3Asets, 1C3 is empty.

Only those frequent sets which involve Yield ($B_1$) as candidates for forming rules are considered and we use $B_1$ as the consequent of those rules (assuming this is the user's choice). The rule which can be formed with $B_1$ as the consequent is: $[1,1]_4 \rightarrow [0,0]_1$ (rule support=11). The supports of the antecedent is, support$([1,1]_4)$=16, giving confidence$([1,1]_4 \rightarrow [0,0]_1)$=$11/16$. Thus, this is a strong rule.

The frequent 1-bit 1Asets were $[0,0]_1$ and $[1,1]_4$ and the other 1-bit 1Asets are infrequent. This means all their enclosed 2-bit subintervals are infrequent. The interval $[00,01]_1$ is identical to $[0,0]_1$ in terms of the full 8-bit values that are included, and $[00,10]_1$ is a superset of $[0,0]_1$, so both are frequent.

Others in band-1 to consider are: [00,00], [01,01], [01,10] and [01,11]. [00,00] is infrequent (using $P_{1,00}$, count=7). [01,01] is infrequent (using $P_{1,01}$, count=4). For [01,10] we use $P_{1,01}$ OR $P_{1,10}$. If it is frequent, then [01,11] is frequent, otherwise, for [01,11] we use $P_{1,01}$ OR $P_{1,10}$ OR $P_{1,11}$. The OR operation is very similar to the AND operation except that the role of 0 and 1 interchange. A result quadrant is pure-0 if both operand quadrants are pure-0. If either operand quadrant is pure-1, the result is pure-1. The root count of $P_{1,01}$ OR $P_{1,10}$ is 6 and therefore [01,11] is infrequent. The root count of $P_{1,01}$ OR $P_{1,10}$ OR $P_{1,11}$ is 9 and therefore [01,11] is infrequent.

The only new frequent 2-bit band$_1$ 1Aset is $[00,10]_1$, which does not form the support set of a rule. Thus, the P-ARM technique terminates.

Deriving High Confidence Rules for Spatial Data Using Tuple Count Cube

The traditional task of association rule mining is to find all rules with high support and high confidence. In some applications, such as mining spatial datasets for natural resources, the task is to find high confidence rules even though their supports may be low. In still other applications, such as the identification of agricultural pest infestations, the task is to find high confidence rules preferably while the support is still very low. The basic Apriori technique cannot be used to solve this problem efficiently, i.e., setting the minimal support to a very low value, so that high confidence rules with almost no support limit can be derived is impractical as it leads to a huge number of frequent itemsets. However, the PC-tree and TC-cube described earlier can be used to derive high confidence rules without such a problem.

Described hereinbelow is a TC-cube based method for mining non-redundant, low-support, high-confidence rules. Such rules will be called confident rules. The main interest is in rules with low support, which are important for many application areas such as natural resource searches, agriculture pest infestations identification, etc. However, a small positive support threshold is set in order to eliminate rules that result from noise and outliers. A high threshold for confidence is set in order to find only the most confident rules.

To eliminate redundant rules resulting from over-fitting, an technique similar to the one introduced in "Growing Decision Trees on Support-less Association Rules" by Ke Wang, Senquiang Zhou, and Yu He (KDD 2000, Boston, Mass.), which is hereby incorporated by reference, is used. In the "Growing Decision Trees . . . " article, rules are ranked based on confidence, support, rule-size, and data-value ordering, respectively. Rules are compared with their generalizations for redundancy before they are included in the set of confident rules. Herein, a similar rank definition is used, except that support level and data-value ordering is not used. Since support level is expected to be very low in many spatial applications, and since a minimum support is set only to eliminate rules resulting from noise, it is not used in rule ranking. Rules are declared redundant only if they are outranked by a generalization. It is chosen not to eliminate a rule which is outranked only by virtue the specific data values involved.

A rule r, ranks higher than rule r', if confidence[r]>confidence[r'], or if confidence[r]=confidence[r'] and the number of attributes in the antecedent of r is less than the number in the antecedent of r'.

A rule r, generalizes a rule r', if they have the same consequent and the antecedent of r is properly contained in the antecedent of r'. The technique for mining confident rules from spatial data is as follows.

---

Build the set of confident rules, C (initially empty) as follows.
Start with 1-bit values, 2 bands;
then 1-bit values and 3 bands; . . .
then 2-bit values and 2 bands;
then 2-bit values and 3 bands; . . .
. . .
At each stage defined above, do the following:
Find all confident rules (support at least minimum_support and confidence at least minimum_confidence), by rolling-up the TC-cube along each potential consequent set using summation. Comparing these sums with the support threshold to isolate rule support sets with the minimum support. Compare the normalized TC-cube values (divide by the rolled-up sum) with the minimum confidence level to isolate the confident rules. Place any new confident rule in C, but only if the rank is higher than any of its generalizations already in C

---

The following example contains 3 bands of 3-bit spatial data in bSQ format.
Band-1:

| B11 | B12 | B13 |
|---|---|---|
| 11 11 00 01 | 00 00 11 00 | 11 11 00 00 |
| 11 01 00 01 | 00 00 11 00 | 11 11 00 00 |
| 11 00 00 11 | 00 00 11 01 | 11 11 00 00 |
| 11 00 01 11 | 00 00 11 10 | 11 11 00 00 |
| 11 11 00 00 | 11 11 00 00 | 00 11 00 00 |
| 11 11 00 00 | 11 11 00 00 | 10 11 00 00 |
| 11 11 00 00 | 10 01 00 11 | 00 00 00 00 |
| 11 11 00 00 | 10 11 00 11 | 00 01 00 00 |

Therefore, the mask trees (PM-trees) for these band-1 bSQ files are:

| PM11 | PM12 | PM13 |
|---|---|---|
| mm10 | 0mmm | 10m0 |
| 1m10 0mm1 | 101m 11mm 0001 | m10m |
| 1101 0101 0001 | 0110 1010 0111 | 0010 0001 |

Band-2: (with the Mask Trees for Band-2 bSQ Files)

| B21 | B22 | B23 |
|---|---|---|
| 00 00 00 11 | 00 11 00 00 | 11 11 11 11 |
| 00 00 00 11 | 00 11 00 00 | 11 11 11 11 |
| 00 00 11 00 | 11 00 00 00 | 11 11 11 11 |
| 00 00 11 00 | 11 00 00 00 | 11 11 11 11 |
| 11 11 00 00 | 11 11 11 11 | 11 11 00 11 |
| 11 11 00 00 | 11 11 11 11 | 11 11 00 10 |
| 11 11 00 00 | 10 01 11 11 | 11 11 00 11 |
| 11 11 00 00 | 10 11 11 11 | 11 11 00 11 |

| PM21 | PM22 | PM23 |
|---|---|---|
| 0m10 | m011 | 111m |
| 0110 | 0110 | 0m01 |

Band-3: (with the Mask Trees for Band-3 bSQ Files)

| B31 | B32 | B33 |
|---|---|---|
| 11 11 00 00 | 00 00 00 00 | 00 00 11 11 |
| 11 11 00 00 | 00 00 00 00 | 00 00 11 11 |
| 11 11 00 00 | 00 00 11 00 | 10 11 11 11 |
| 11 11 00 00 | 00 00 11 00 | 10 11 11 11 |
| 00 00 11 01 | 00 00 00 00 | 11 11 11 11 |
| 00 00 11 11 | 00 00 00 00 | 11 11 11 11 |
| 00 00 00 11 | 11 00 00 00 | 11 11 11 11 |
| 00 00 00 11 | 11 00 00 00 | 11 11 11 11 |

| PM31 | PM32 | PM33 |
|---|---|---|
| 100m | 00m0 | m111 |
| 1m01 | 0010 | 00ml |
| 0111 | | 1010 |

Assume minimum confidence threshold of 80% and minimum support threshold of 10%. Start with 1-bit values and 2 bands, B1 and B2. The required PM-trees and their corresponding PC-trees are:

| PM11^21 | PC11^22 | PM11^21' | PC11^21' |
|---|---|---|---|
| 0m10 | 19 | mm01 | 25 |
| 0mm0 | 0 3 16 0 | 0m01 1000 | 5 4 0 16 |
| 0101 0001 | 0210 | 0010 | 0104 4000 |
| | 0101 0001 | | 0010 |

| PM11^21' | PC11^21' | PM11^21 | PC11^21 |
|---|---|---|---|
| mm00 | 15 | 0m00 | 5 |
| 1m10 0001 | 11 4 0 0 | 0mm0 | 0 5 0 0 |

| PM11^21' | PC11^21' | PM11^21 | PC11^21 |
|---|---|---|---|
| 1101 | 4340 0004 | 1010 1110 | 0230 |
| | 1101 | | 1010 1110 |

The TC-cube values (root counts from the PC-trees):

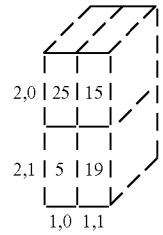

The rolled-up sums and confidence thresholds are:

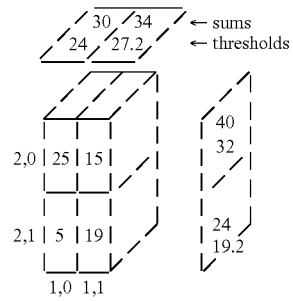

All sums are at least 10% support (6.4). There is one confident rule:

C:

B1 = {0} => B2 = {0} with confidence = 83.3%

Continue with 1-bit values and the 2 bands, B1 and B3, we can get the following TC-cube with rolled-up sums and confidence thresholds:

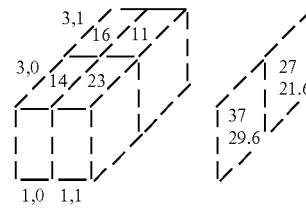

There are no new confident rules. Similarly, the 1-bit TC-cube for band B2 and B3 can be constructed below.

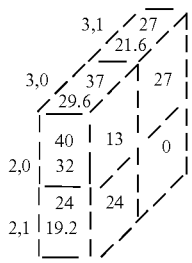

All sums are at least 10% of 64 (6.4), thus, all rules will have enough support. There are two confident rule, B2={1}=>B3={0} with confidence=100% and B3={1}=>B2={0} with confidence=100%. Thus,

C:

$B1 = \{0\} \Rightarrow B2 = \{0\}$ $c = 83.3\%$ $B2 = \{1\} \Rightarrow B3 = \{0\}$ $c = 100\%$ $B3 = \{1\} \Rightarrow B2 = \{0\}$ $c = 100\%$ Next, consider 1-bit values and bands, B1, B2, and B3. The counts, sums and confidence thresholds are:

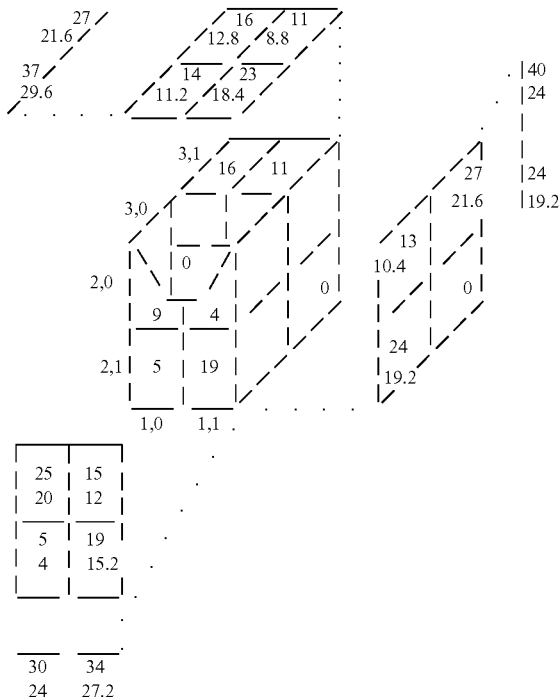

Support sets, B1={0}^B2={1} and B2={1}^B3={1} lack support. The new confident rules are:

$B1 = \{1\} \wedge B2 = \{1\} \Rightarrow B3 = \{0\}$, confidence = 100%

$B1 = \{1\} \wedge B3 = \{0\} \Rightarrow B2 = \{1\}$, confidence = 82.6%

-continued $B1 = \{1\} \wedge B3 = \{1\} \Rightarrow B2 = \{0\}$, confidence = 100%

$B1 = \{0\} \wedge B3 = \{1\} \Rightarrow B2 = \{0\}$, confidence = 100%

B1={1}^B2={1}=>B3={0} is not included because it is generalized by B2={1}=>B3={0}, which is already in C and has higher rank. Also, B1={1}^B3={1}=>B2={0} is not included because it is generalized by B3={1}=>B2={0}, which is already in C and has higher rank. B1={0}^B3={1}=>B2={0} is not included because it is generalized by B3={1}=>B2={0}, which has higher rank also. Thus,

C:

$B1 = \{0\} \Rightarrow B2 = \{0\}$ $c = 83.3\%$ $B2 = \{1\} \Rightarrow B3 = \{0\}$ $c = 100\%$ $B3 = \{1\} \Rightarrow B2 = \{0\}$ $c = 100\%$ $B1 = \{1\} \wedge B3 = \{0\} \Rightarrow B2 = \{1\}$ $c = 82.6\%$ Next, 2-bit data values are considered and one proceeds in the same way. Depending upon the goal of the data mining task (e.g., mine for classes of rules, individual rules, . . . ) the rules already in C can be used to obviate the need to consider 2-bit refinements of the rules in C. This simplifies the 2-bit stage markedly.

In utilizing TC-cubes, the TC-cube values are preferably built from basic PC-trees on-the-fly as needed. Once the TC-cube is built, the mining task can be performed with different parameters (i.e., different support and confidence thresholds) without rebuilding the cube. Using the roll-up cube operation, one can obtain the TC-cube for n bit from the TC-cube for n+1 bit. This is a good feature of bit value concept hierarchy.

The functionalities of deriving high confidence rules utilizing TC-cubes has been enhanced in two ways over other manners of deriving rules. Firstly, the antecedent attribute is not specified. Compared to other approaches for deriving high confidence rules, the TC-cube is more general. Secondly, redundant rules based on the rule rank are removed.

An important feature of the utilization of TC-cubes is the scalability. This has two meanings. First, the TC-cube technique is scalable with respect to the data set size. The reason is that the size of TC-cube is independent of the data set size, but only based on the number of bands and number of bits. In addition, the mining cost only depends on the TC-cube size. For example, for an image with size 8192×8192 with three bands, the TC-cube using 2 bits is as simple as that of the example provided above. By comparison, in the Apriori technique, the larger the data set, the higher the cost of the mining process. Therefore, the larger the data set, the more benefit in using the present invention.

The other aspect of scalability is that the TC-cube technique is scalable with respect to the support threshold. The example above focuses on mining high confidence rules with very small support. As the support threshold is decreased to very low value, the cost of using the Aprioi technique will be increased dramatically, resulting in a huge number of frequent itemsets (combination exploration). However, in the TC-cube technique, the process is not based on the frequent itemsets generation, so it works well for low support threshold.

As mentioned earlier, there is an additional cost to build the TC-cube. The key issue of this cost is the PC-tree ANDing. Parallel ANDing of PC-trees is preferably implemented, which is efficient on a cluster of computers.

For the example above, an array of 16 dual 266 MHz processor systems with a 400 MHz dual processor as the control node was used. The 2048*2048 image was partitioned among all the nodes. Each node contains data for 512×512 pixels. These data are stored at different nodes as another variation of PC-tree, called Peano Vector Tree (PV-Tree). Here is how PV-tree is constructed. First, a Peano Count Tree is built using fan-out 64 for each level. Then the tree is saved as bit vectors. For each internal node (except the root), two 64 bit bit-vectors are used, one is for pure1 and other is for pure0. At the leaf level, only one vector (for pure1) is used. The pseudo-code of FIG. 19 describes this implementation in detail.

From a single TM scene, there will be 56 (7×8) Peano Vector Trees—all saved in a single node. Using 16 nodes a scene of size 2048×2048 can be covered.

When it is necessary to perform the ANDing operation on the entire scene, the local ANDing result of two Peano Vector Trees is calculated and the result sent to the control node, giving the final result. The pseudo-code of FIG. 20 describes the local ANDing operation.

Figure 21:
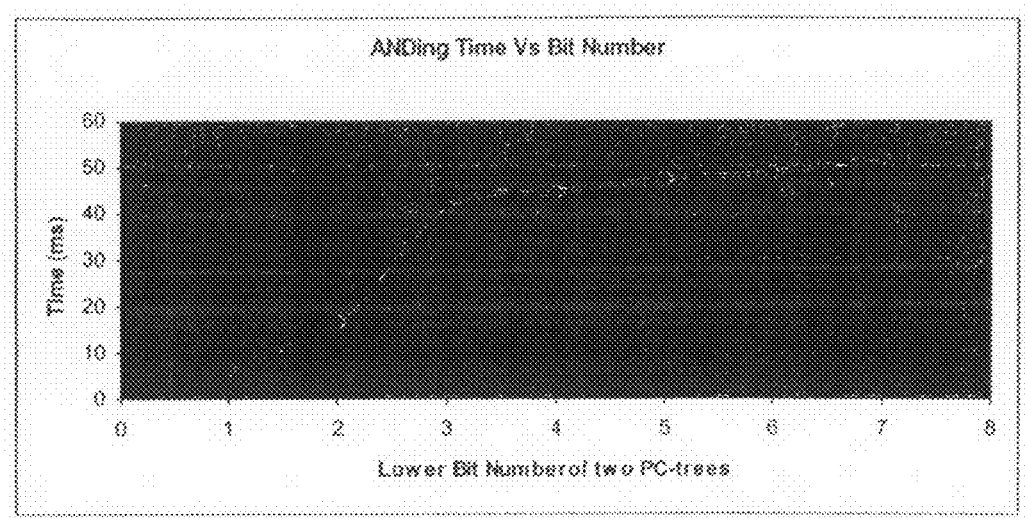
FIG. 21 is a graph depicting PC-tree ANDing time.

Message Passing Interface (MPI) is used on the cluster to implement the logical operations on Peano Vector Trees. This program uses the Single Program Multiple Data (SPMD) paradigm. The graph of FIG. 21 shows the result of ANDing time experiments that have been observed (to perform AND operation on two Peano Vector Trees) for a TM scene. The AND time varies from 6.72 ms to 52.12 ms. With this high speed ANDing, the TC-cube can be built very quickly. For example, for a 2-bit 3-band TC-cube, the total AND time is about 1 second.

IV. B. Classification

Classification is another useful approach to mining information from spatial data. In classification, a training (learning) set is identified for the construction of a classifier. Each record in the training set has several attributes. There is one attribute, called the goal or class label attribute, which indicates the class to which each record belongs. A test set is used to test the accuracy of the classifier once it has been developed from the learning dataset. The classifier, once certified, is used to predict the class label of a new, unknown class tuple. Different models have been proposed for classification, such as decision tree induction, neural network, Bayesian, fuzzy set, nearest neighbor, and so on. Among these models, decision tree induction is widely used for classification, such as ID3 (and its variants such as C4.5, CART, Interval Classifier, SPRINT and BOAT.)

A classification task typically involves three phases, a learning phase, a testing phase, and an application phase. In the learning phase, training data are analyzed by a classification technique. Each tuple in a training dataset is a training sample randomly selected from the sample population. A class label attribute is identified whose values are used to label the classes. The learning model or classifier resulting from this learning phase may be in the form of classification rules, or a decision tree, or a mathematical formulae. Since the class label of each training sample is provided, this approach is known as supervised learning. In unsupervised learning (clustering), the class labels are not known in advance.

In the testing phase test data are used to assess the accuracy of classifier. Each tuple of the test dataset is randomly selected from the sample population, usually with the additional condition that no sample should be in both the learning set and the test set. If the classifier passes the test phase, it is used for the classification of new data tuples. This is the application phase. The new tuples do not have a class attribute label. The classifier predicts the class label for these new data samples. An example of simple spatial data classification by decision tree induction is provided below.

In this example the data is a remotely sensed image (e.g., satellite image or aerial photo) of an agricultural field taken during the previous growing season and the crop yield levels for that field, measured at the end of that same growing season. These data are sampled to make up the learning and test datasets. The new data samples are remotely sensed image values taken during a "current" growing season prior to harvest. The goal is to classify the previous year's data using yield as the class label attribute and then to use the resulting classifier to predict yield levels for the current year (e.g., to determine where additional nitrogen should be applied to raise yield levels). The decision tree is expressed as a conjunctive rule. NIR stands for "Near Infrared". The training dataset is as follows:

Training set:

| FIELD COORD | | REMOTELY SENSED REFLECTANCE LEVELS | | | | YIELD LEVELS |
|---|---|---|---|---|---|---|
| X | Y | Blue | Green | Red | NIR | |
| 0 | 0 | 0000 1001 | 1010 1111 | 0000 0110 | 1111 0101 | medium |
| 3 | 1 | 0000 1011 | 1011 0100 | 0000 0101 | 1111 0111 | medium |
| 2 | 2 | 0000 1011 | 1011 0101 | 0000 0100 | 1111 0111 | high |
| 1 | 1 | 0000 0111 | 1011 0111 | 0000 0011 | 1111 1000 | high |
| 0 | 4 | 0000 0111 | 1011 1011 | 0000 0001 | 1111 1001 | high |
| 7 | 6 | 0000 1000 | 1011 1111 | 0000 0000 | 1111 1011 | high |

Classification Technique (classify by yield level)

Classification (classify with respect to YIELD level
IF NIR > 1111 0111 and Red < 0000 0110 THEN YIELD = high Test Data:

| FIELD COORD | | REMOTELY SENSED REFLECTANCE LEVELS | | | | YIELD LEVELS |
|---|---|---|---|---|---|---|
| X | Y | Blue | Green | Red | NIR | |
| 1 | 0 | 0001 1101 | 1010 1110 | 0000 0111 | 1111 0100 | medium |
| 0 | 1 | 0000 1111 | 1011 0101 | 0000 0110 | 1111 0110 | medium |
| 0 | 2 | 0001 1111 | 1011 0111 | 0000 0101 | 1111 0110 | medium |
| 7 | 3 | 0001 1111 | 1011 0110 | 0000 0010 | 1111 1000 | high |
| 4 | 4 | 0001 1111 | 1111 1010 | 0000 0010 | 1111 1000 | high |
| 6 | 6 | 0001 1111 | 1011 1110 | 0000 0001 | 1111 1010 | high |

↓

Classifier
IF NIR > 1111 0111 and Red < 0000 0110 THEN YIELD = high

↓ prediction accuracy percentage = 100%

New Data:

| FIELD COORD | | REMOTELY SENSED REFLECTANCE LEVELS | | | | YIELD LEVELS |
|---|---|---|---|---|---|---|
| X | Y | Blue | Green | Red | NIR | |
| 8 | 6 | 0001 1100 | 1011 1110 | 0000 0001 | 1111 1110 | ? |

↓

Classifier
IF NIR > 1111 0111 and Red < 0000 0110 THEN YIELD = high

↓

YIELD = high

In the overall classification effort, as in most data mining approaches, there is a data preparation stage in which the data is prepared for classification. Data preparation can involve cleaning (noise reduction by applying smoothing techniques and missing value management techniques). The PC-tree data structure facilitates a proximity-based data smoothing method which can reduce the data classification time considerably. The smoothing method is called bottom-up purity shifting. By replacing 3 counts with 4 and 1 counts with 0 at level-1 (and making resultant changes on up the tree), the data is smoothed and the PC-tree is compactified.

A more drastic smoothing can be effected by deciding at any level, which set of counts to replace with pure1 and which set of counts to replace with pure0.

Another important pre-classification step is relevance analysis (selecting only a subset of the feature attributes, so as to improve technique efficiency). This step can involve removal of irrelevant attributes, removal of redundant attributes, etc. A very effective way to determine relevance is to rollup the TC-cube to the class label attribute and each other potential decision attribute in turn. If any of these rollups produce counts that are roughly uniformly distributed, then that attribute is not going to be effective in classifying the class label attribute. The rollup can be computed from the basic PC-trees without necessitating the creation of the TC-cube. This can be done by ANDing the class label attribute PC-trees with the PC-trees of the potential decision attribute.

Since a rough estimate of uniformity in the root counts is all that is needed, ever better estimates can be discovered ANDing only down to a fixed depth of the PC-trees (which can be done very quickly). For instance, ANDing only depth=1 counts provides the roughest of distribution information, ANDing at depth=2 provides better distribution information, and so forth.

A Decision Tree is a flowchart-like structure in which each inode denotes a test on an attribute, each branch represents an outcome of the test and the leaf nodes represent classes or class distributions. Unknown samples can be classified by testing attributes against the tree. Paths traced from root to leaf holds the class prediction for that sample. The basic technique for inducing a decision tree from the learning or training sample set is as follows:

Initially the decision tree is a single node representing the entire training set.

If all samples are in the same class, this node becomes a leaf and is labeled with that class label.

Otherwise, an entropy-based measure, "information gain", is used as a heuristic for selecting the attribute which best separates the samples into individual classes (the "decision" attribute).

A branch is created for each value of the test attribute and samples are partitioned accordingly.

The technique advances recursively to form the decision tree for the sub-sample set at each partition. Once an attribute has been used, it is not considered in descendent nodes.

The technique stops when all samples for a given node belong to the same class or when there are no remaining attributes.

The attribute selected at each decision tree level is the one with the highest information gain. The information gain of an attribute is computed as follows. Let S be the set of data samples in the learning dataset and let s be its cardinality. Let the class label attribute have m values or classes, $C_i$, i=1 .. m. Let $s_i$ be number of samples from S in class, Ci. The expected information needed to classify a given sample is computed as follows.

$$I(s_1 .. s_m) = -\Sigma_{i=1..m} p_i * \log_2 p_i \quad p_i = s_i/s \text{ (the probability that a sample belongs to } C_i\text{)}.$$

Let attribute A, have v distinct values, $\{a_1 .. a_v\}$. A could be used to classify S into $\{S_1 .. S_v\}$, where $S_j$ is the set of samples having value, $a_j$. Let $s_{ij}$ be the number of samples of class $C_i$, in a subset, $S_j$. The entropy or expected information based on the partition into subsets by A is $$E(A) = \Sigma_{j=1..v} \Sigma_{i=1..m} (s_{ij}/s) * I(s_{1j} .. s_{mj})$$

The information gained by using A as a decision attribute is: gain(A)=I($s_1$ .. $s_m$)–E(A) Branches are created for each value of the selected attribute and samples are partitioned accordingly. The following learning relation contains 4 bands of 4-bit data values (expressed in decimal and binary) (BSQ format would consist of the 4 projections of this relation, R[YIELD], R[Blue], R[Green], R[Red]).

| FIELD | CLASS | REMOTELY SENSED REFLECTANCES | | |
|---|---|---|---|---|
| COORDS X, Y | LABEL YIELD | Blue | Green | Red |
| 0, 0 | 3 | 7 | 8 | 11 |
| 0, 1 | 3 | 3 | 8 | 15 |
| 0, 2 | 7 | 3 | 4 | 11 |
| 0, 3 | 7 | 2 | 5 | 11 |
| 1, 0 | 3 | 7 | 8 | 11 |
| 1, 1 | 3 | 3 | 8 | 11 |
| 1, 2 | 7 | 3 | 4 | 11 |
| 1, 3 | 7 | 2 | 5 | 11 |
| 2, 0 | 2 | 11 | 8 | 15 |
| 2, 1 | 2 | 11 | 8 | 15 |
| 2, 2 | 10 | 10 | 4 | 11 |
| 2, 3 | 15 | 10 | 4 | 11 |
| 3, 0 | 2 | 11 | 8 | 15 |
| 3, 1 | 10 | 11 | 8 | 15 |
| 3, 2 | 15 | 10 | 4 | 11 |
| 3, 3 | 15 | 10 | 4 | 11 |

| FIELD | CLASS | REMOTELY SENSED REFLECTANCES | | |
|---|---|---|---|---|
| COORDS X, Y | LABEL YIELD | Blue | Green | Red |
| 0, 0 | 0011 | 0111 | 1000 | 1011 |
| 0, 1 | 0011 | 0011 | 1000 | 1111 |
| 0, 2 | 0111 | 0011 | 0100 | 1011 |
| 0, 3 | 0111 | 0010 | 0101 | 1011 |
| 1, 0 | 0011 | 0111 | 1000 | 1011 |
| 1, 1 | 0011 | 0011 | 1000 | 1011 |
| 1, 2 | 0111 | 0011 | 0100 | 1011 |
| 1, 3 | 0111 | 0010 | 0101 | 1011 |
| 2, 0 | 0010 | 1011 | 1000 | 1111 |
| 2, 1 | 0010 | 1011 | 1000 | 1111 |
| 2, 2 | 1010 | 1010 | 0100 | 1011 |
| 2, 3 | 1111 | 1010 | 0100 | 1011 |
| 3, 0 | 0010 | 1011 | 1000 | 1111 |
| 3, 1 | 1010 | 1011 | 1000 | 1111 |
| 3, 2 | 1111 | 1010 | 0100 | 1011 |
| 3, 3 | 1111 | 1010 | 0100 | 1011 |

This learning dataset is converted to bSQ format. We display the bSQ bit-bands values in their spatial positions, rather than displaying them in 1-column files. The Band-1 bit-bands are:

| $B_{11}$ | $B_{12}$ | $B_{13}$ | $B_{14}$ |
|---|---|---|---|
| 0000 | 0011 | 1111 | 1111 |
| 0000 | 0011 | 1111 | 1111 |
| 0011 | 0001 | 1111 | 0001 |
| 0111 | 0011 | 1111 | 0011 |

Thus, the Band-1 basic PC-trees are as follows (tree pointers are omitted).

| $PC_{1,1}$ | $PC_{1,2}$ | $PC_{1,3}$ | $PC_{1,4}$ |
|---|---|---|---|
| 5 | 7 | 16 | 11 |
| 0 0 1 4 | 0 4 0 3 | | 4 4 0 3 |
| 0001 | 0111 | | 0111 |

The PC-trees for 4-bit values are given. The creation process for only, $PC_{1,0011}$, is shown as an example.

| $PC_{1,0011}$ = | $PC_{1,1}'$ AND | $PC_{1,2}'$ AND | $PC_{1,3}$ AND | $PC_{1,4}$ since, |
|---|---|---|---|---|
| 4 | 11 | 9 | 16 | 11 |
| 4 0 0 0 | 4 4 3 0 | 4 0 4 1 | | 4 4 0 3 |
| | 1110 | 1000 | | 0111 |
| 0 1 20 21 22 | (pure1 paths of $PC_{1,1}'$) | | | |
| 0   2 | 31 | (pure1 paths of $PC_{1,2}'$) | | |
| 0 1 | 31 32 33 | (pure1 paths of $PC_{1,4}$, $PC_{1,3}$ has no pure1 paths)) | | |
| 0 | (pure1 paths of $PC_{1,0011}$). | | | |

| $PC_{1,0000}$ | $PC_{1,0100}$ | $PC_{1,1000}$ | $PC_{1,1100}$ | $PC_{1,0010}$ | $PC_{1,0110}$ | $PC_{1,1010}$ | $PC_{1,1110}$ |
|---|---|---|---|---|---|---|---|
| 0 | 0 | 0 | 0 | 3<br>0 0 3 0<br>1 1 1 0 | 0 | 2<br>0 0 1 1<br>0 0 0 1 1 0 0 0 | 0 |

| $PC_{1,0001}$ | $PC_{1,0101}$ | $PC_{1,1001}$ | $PC_{1,1101}$ | $PC_{1,0011}$ | $PC_{1,0111}$ | $PC_{1,1011}$ | $PC_{1,1111}$ |
|---|---|---|---|---|---|---|---|
| 0 | 0 | 0 | 0 | 4<br>4 0 0 0 | 4<br>0 4 0 0 | 0 | 3<br>0 0 0 3<br>0 1 1 1 |

| $B_{21}$ | $B_{22}$ | $B_{23}$ | $B_{24}$ |
|---|---|---|---|
| 0000 | 1000 | 1111 | 1110 |
| 0000 | 1000 | 1111 | 1110 |
| 1111 | 0000 | 1111 | 1100 |
| 1111 | 0000 | 1111 | 1100 |

| $PC_{2,0000}$ | $PC_{2,0100}$ | $PC_{2,1000}$ | $PC_{2,1100}$ | $PC_{2,0010}$ | $PC_{2,0110}$ | $PC_{2,1010}$ | $PC_{2,1110}$ |
|---|---|---|---|---|---|---|---|
| 0 | 0 | 0 | 0 | 2<br>0 2 0 0<br>0 1 0 1 | 0 | 4<br>0 0 0 4 | 0 |

| $PC_{2,0001}$ | $PC_{2,0101}$ | $PC_{2,1001}$ | $PC_{2,1101}$ | $PC_{2,0011}$ | $PC_{2,0111}$ | $PC_{2,1011}$ | $PC_{2,1111}$ |
|---|---|---|---|---|---|---|---|
| 0 | 0 | 0 | 0 | 4<br>2 2 0 0<br>0 1 0 1 1 0 1 0 | 2<br>2 0 0 0<br>1 0 1 0 | 4<br>0 0 4 0 | 0 |

| $B_{31}$ | $B_{32}$ | $B_{33}$ | $B_{34}$ |
|---|---|---|---|
| 1100 | 0011 | 0000 | 0001 |
| 1100 | 0011 | 0000 | 0001 |
| 1100 | 0011 | 0000 | 0000 |
| 1100 | 0011 | 0000 | 0000 |

| $PC_{3,0000}$ | $PC_{3,0100}$ | $PC_{3,1000}$ | $PC_{3,1100}$ | $PC_{3,0010}$ | $PC_{3,0110}$ | $PC_{3,1010}$ | $PC_{3,1110}$ |
|---|---|---|---|---|---|---|---|
| 0 | 6<br><br>0 2 0 4<br><br>1 0 1 0 | 8<br><br>4 0 4 0 | 0 | 0 | 0 | 0 | 0 |

| $PC_{3,0001}$ | $PC_{3,0101}$ | $PC_{3,1001}$ | $PC_{3,1101}$ | $PC_{3,0011}$ | $PC_{3,0111}$ | $PC_{3,1011}$ | $P_{3,1111}$ |
|---|---|---|---|---|---|---|---|
| 0 | 2<br><br>0 2 0 0<br><br>0 1 0 1 | 0 | 0 | 0 | 0 | 0 | 0 |

| $B_{41}$ | $B_{42}$ | $B_{43}$ | $B_{44}$ |
|---|---|---|---|
| 1111 | 0100 | 1111 | 1111 |
| 1111 | 0000 | 1111 | 1111 |
| 1111 | 1100 | 1111 | 1111 |
| 1111 | 1100 | 1111 | 1111 |

| $PC_{4,0000}$ | $PC_{4,0100}$ | $PC_{4,1000}$ | $PC_{4,1100}$ | $PC_{4,0010}$ | $PC_{4,0110}$ | $PC_{4,1010}$ | $PC_{4,1110}$ |
|---|---|---|---|---|---|---|---|
| 0 | 0 | 0 | 0 | 0 | 0 | 0 | 0 |

| $PC_{4,0001}$ | $PC_{4,0101}$ | $PC_{4,1001}$ | $PC_{4,1101}$ | $PC_{4,0011}$ | $PC_{4,0111}$ | $PC_{4,1011}$ | $PC_{4,1111}$ |
|---|---|---|---|---|---|---|---|
| 0 | 0 | 0 | 0 | 0 | 0 | 11<br>3 4 0 4<br>1011 | 5<br>1 0 4 0<br>0100 |

The basic technique for inducing a decision tree from this learning set is as follows.

1. The tree starts as a single node representing the set of training samples, S:

2. If all samples are in same class (same B1-value), S becomes a leaf with that class label. No.

3. Otherwise, use entropy-based measure, information gain, as the heuristic for selecting the attribute which best separates the samples into individual classes (the test or decision attribute).

Start with A=B2 to classify S into $\{A_1 .. A_v\}$, where $A_j=\{t|t(B2)=a_j\}$ and $a_j$ ranges over those B2-values, v', such that the root count of $PC_{2,v'}$ is non-zero. The symbol, $s_{ij}$, counts the number of samples of class, $C_i$, in subset, $A_j$, that is, the root count of $PC_{1,v}$ AND $PC_{2,v'}$, where v ranges over those B1-values such that the root count of $PC_{1,v}$ is non-zero. Thus, the $s_{ij}$ are as follows (i=row and j=column).

```
0  0  0  0  3
0  2  2  0  0
2  2  0  0  0
0  0  0  1  1
0  0  0  3  0
```

(the probability that a sample belongs to $C_i$).

Let attribute A, have v distinct values, $\{a_1 .. a_v\}$. A could be used to classify S into $\{S_1..S_v\}$, where $S_j$ is the set of samples having value, $a_j$. Let $s_{ij}$ be the number of samples of class, $C_i$, in a subset, $S_j$.

The expected information needed to classify the sample is
$I(s_1 .. s_m)=-\Sigma_{i..m} p_i * \log_2 p_i$ $p_i=s_i/s$
(m=5 $s_i$=3,4,4,2,3 $p_i=s_i/s$=3/16, 1/4, 1/4, 1/8, 3/16, respectively).
Thus, $$I = -(3/16*\log_2(3/16) + 4/16*\log_2(4/16) + 4/16*\log_2(4/16) + 2/16*\log_2(2/16) + 3/16*\log_2(3/16))$$
$$= -(-.453 \quad -.5 \quad -.5 \quad -.375 \quad -.453)$$
$$= 2.281$$

The entropy based on the partition into subsets by B2 is
$E(A)=\Sigma_{j=1..v}\Sigma_{i=1..m}(s_{ij}/s)*I(s_{ij} .. s_{mj})$, where $I(s_{1j} .. s_{mj})=-\Sigma_{i=1..m} p_{ij}*\log_2 p_{ij}$ $p_{ij}=s_{ij}/|A_j|$.

The computations leading to the gain for B2 are finished in detail.

| 2 | 4 | 2 | 4 | 4 | ← | $|A_j|$ (divisors) |
|---|---|---|---|---|---|---|
| 0 | 0 | 0 | 0 | .75 | ← | $p_{1j}$ |
| 0 | .5 | 1 | 0 | 0 | ← | $p_{2j}$ |
| 1 | .5 | 0 | 0 | 0 | ← | $p_{3j}$ |
| 0 | 0 | 0 | .25 | .25 | ← | $p_{4j}$ |
| 0 | 0 | 0 | .75 | 0 | ← | $p_{5j}$ |
| 0 | 0 | 0 | 0 | -.311 | ← | $p_{1j}*\log_2(p_{1j})$ |
| 0 | -.5 | 0 | 0 | 0 | ← | $p_{2j}*\log_2(p_{2j})$ |
| 0 | -.5 | 0 | 0 | 0 | ← | $p_{3j}*\log_2(p_{3j})$ |
| 0 | 0 | 0 | .5 | -.5 | ← | $p_{4j}*\log_2(p_{4j})$ |
| 0 | 0 | 0 | .311 | 0 | ← | $p_{5j}*\log_2(p_{5j})$ |
| 0 | 1 | 0 | .811 | .811 | ← | $I(s_{1j}+..+s_{5j})$ |
| 2 | 4 | 2 | 4 | 4 | ← | $s_{1j}+..+s_{5j}$ |
| 0 | .25 | 0 | .203 | .203 | ← | $(s_{1j}+..+s_{5j})*I(s_{1j}+..+s_{5j})/16$ |
| | | | | .656 | ← | E(B2) |
| | | | | 2.281 | ← | $I(s_1..s_m)$ |
| | | | | 1.625 | ← | $I(s_1..s_m)$-E(B2) = Gain(B2) |
| Likewise, the Gains of B3 | | | | 1.084 | | = Gain(B3) |
| and B4 are computed. | | | | 0.568 | | = Gain(B4) |

Thus, B2 is selected as the first level decision attribute.

4. Branches are created for each value of B2 and samples are partitioned accordingly (if a partition is empty, generate a leaf and label it with the most common class, C2, labeled with 0011).

| | B2 = 0010 → Sample_Set_1 | | |
| | B2 = 0011 → Sample_Set_2 | | |
| | B2 = 0111 → Sample_Set_3 | | |
| | B2 = 1010 → Sample_Set_4 | | |
| | B2 = 1011 → Sample_Set_5 | | |
| X-Y | B1 | B3 | B4 |
|---|---|---|---|
| | Sample_Set_1 | | |
| 0, 3 | 0111 | 0101 | 1011 |
| 1, 3 | 0111 | 0101 | 1011 |
| | Sample_Set_2 | | |
| 0, 1 | 0011 | 1000 | 1111 |
| 0, 2 | 0111 | 0100 | 1011 |
| 1, 1 | 0011 | 1000 | 1011 |
| 1, 2 | 0111 | 0100 | 1011 |
| | Sample_Set_3 | | |
| 0, 0 | 0011 | 1000 | 1011 |
| 1, 0 | 0011 | 1000 | 1011 |
| | Sample_Set_4 | | |
| 2, 2 | 1010 | 0100 | 1011 |
| 2, 3 | 1111 | 0100 | 1011 |
| 3, 2 | 1111 | 0100 | 1011 |
| 3, 3 | 1111 | 0100 | 1011 |
| | Sample_Set_5 | | |
| 2, 0 | 0010 | 1000 | 1111 |
| 2, 1 | 0010 | 1000 | 1111 |
| 3, 0 | 0010 | 1000 | 1111 |
| 3, 1 | 1010 | 1000 | 1111 |

5. The technique advances recursively to form a decision tree for the samples at each partition. Once an attribute is the decision attribute at a node, it is not considered further.

6. The technique stops when:
   a. all samples for a given node belong to the same class or
   b. no remaining attributes (label leaf with majority class among the samples).

All samples belong to the same class for Sample_Set_1 and Sample_Set_3. Thus, the decision tree is:

$B2 = 0010 \rightarrow B1 = 0111$ $B2 = 0011 \rightarrow Sample\_Set\_2$ $B2 = 0111 \rightarrow B1 = 0011$ $B2 = 1010 \rightarrow Sample\_Set\_4$ $B2 = 1011 \rightarrow Sample\_Set\_5$ Advancing the technique recursively, it is unnecessary to rescan the learning set to form these Sub-sample sets, since the PC-trees for those samples have been computed.

For Sample_set_2, we compute all $PC_{2,001} \hat{} P_{1,v} \hat{} P_{3,w}$ to calculate Gain(B3); and we compute $PC_{2,001} \hat{} P_{1,v} \hat{} P_{4,w}$ to calculate Gain(B4). The results are:

| | | |
|---|---|---|
| Gain(B4) | → | 0.179 |
| Gain(B3) | → | 1.000 |

Thus, B3 is the decision attribute at this level in the decision tree.

For Sample_Set_4 (label-B2=1010), the PC-trees

| $PC_{1010,1010,,}$ | $PC_{1111,1010,,}$ | $PC_{,1010,0100,}$ | $PC_{,1010,,1011}$ |
|---|---|---|---|
| 1 | 3 | 4 | 4 |
| 0 0 0 1 | 0 0 0 3 | 0 0 0 4 | 0 0 0 4 |
| 1000 | 0111 | | | tell that there is only one B3 and one B4 value in the Sample_Set. Therefore, it can be determined that there will be no gain by using either B3 or B4 at this level in the tree. That conclusion can be reached without producing and scanning the Sample_Set_4.

The same conclusion can be reached regarding Sample_Set_5 (label-B2=1011) simply by examining

| $PC_{0010,1011,,}$ | $PC_{1010,1011,,}$ | $PC_{,1011,1000,}$ | $PC_{,1011,,1111}$ |
|---|---|---|---|
| 3 | 1 | 4 | 4 |
| 0 0 3 0 | 0 0 1 0 | 0 0 4 0 | 0 0 4 0 |
| 1110 | 0001 | | |

Here, an additional stopping condition at is used at step 3, namely,

Any attribute, which has one single value in each candidate decision attribute over the entire sample, need not be considered, since the information gain will be zero. If all candidate decision attributes are of this type, the technique stops for this subsample.

Thus, the majority class label is used for Sample_Sets 4 and 5:

B2=0010→B1=0111

B2=0011→Sample_Set_2

B2=0111→B1=0011

B2=1010→B1=1111

B2=1011→B1=0010

The best test attribute for Sample_Set_2 (of B3 or B4), is found in the same way. The result is that B3 maximizes the information gain. Therefore, the decision tree becomes, $B2 = 0010 \rightarrow B1 = 0111$ $B2 = 0010 \rightarrow \begin{cases} B3 = 0100 \rightarrow Sample\_Set\_2.1 \\ B3 = 1000 \rightarrow Sample\_Set\_2.2 \end{cases}$ $B2 = 0111 \rightarrow B1 = 0011$ $B2 = 1010 \rightarrow B1 = 1111$ $B2 = 1011 \rightarrow B1 = 0010$

| Sample_Set_2.1 | | | | Sample_Set_2.2 | | | |
|---|---|---|---|---|---|---|---|
| X-Y | B1 | B3 | B4 | X-Y | B1 | B3 | B4 |
| 0, 2 | 0111 | 0100 | 1011 | 0, 1 | 0011 | 1000 | 1111 |
| 1, 2 | 0111 | 0100 | 1011 | 1, 1 | 0011 | 1000 | 1011 |

In both cases, there is one class label in the set. Therefore, the technique terminates with the decision tree:

$$B2 = 0010 \to B1 = 0111$$
$$B2 = 0011 \to \begin{cases} B3 = 0100 \to B1 = 0111 \\ B3 = 1000 \to B1 = 0011 \end{cases}$$
$$B2 = 0111 \to B1 = 0011$$
$$B2 = 1010 \to B1 = 1111$$
$$B2 = 1011 \to B1 = 0010$$

Often prediction accuracy is used as a basis of comparison for the different classification methods. However, with regard to this example, ID3 is used with new data structures which are intended to improve the speed of the technique and not the predictive accuracy. Therefore, the important performance issue herein is computation speed relative to ID3.

In the example above, an entire spatial relation (a remotely sensed image (RSI) and the associated yield attribute) constitutes the training set. The spatial relation representing the same location but for a different year, is used as the test set. The learning set and test set are chosen in this way because it is important to test whether the classifier resulting from the leaning data of one year, actually tests out well using data from another year, since the predictions will be made on RSI data taken during yet a third year, the current growing year. (i.e., to predict low yield areas where additional inputs can be applied, such as water and nitrogen, with high likelihood of increasing the yield).

Let:
A=class or goal attribute (e.g., Yield).
T=the cost of testing if all the samples are in the same class initially (step-1 of the technique).
S=the cost to scan the sample set.
P=the cost to perform ANDing of two tuple PC-trees.
G=the cost to do the gain calculation.
C=the cost to create the sample subset.

First, reviewing the initial test, the following can be observed. In ID3, to test if all the samples are in the same class, one scan on the entire sample set is needed. While using PC-trees, only the root counts of the k PC-trees of attribute A need to be checked to determine if they are pure1 quadrants. Here, k is the number of bits used to represent the number of values of attribute A. These AND operations can be performed in parallel, thus, $T_{ID3}=S$, $T_{PCT}=P$.

Figure 22:
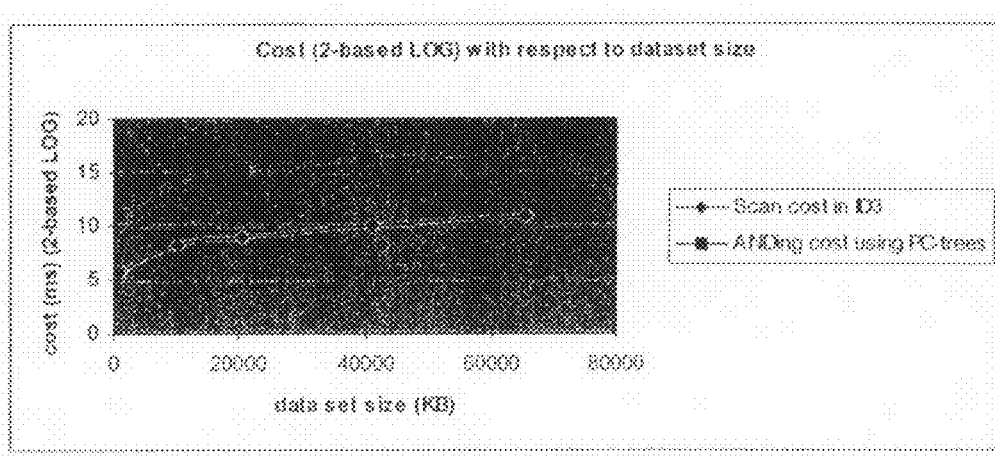
FIG. 22 is a cost comparison for the initial and iteration steps with respect to dataset size for ID3 and the PC-tree technique.

It is assumed that it takes 10-30 ms to read a block from a disk. For a TM scene of 8192*8192, the time to read the scene is 1.28-3.84 second, while for a Digital Photography (DP) image of 1024*1024, the time is 20-60 ms. If PC-trees are used, the time to perform the AND for a TM scene is about 100 ms and for a DP is about 10 ms. Thus, it can be said that P<S, so $T_{PCT}<T_{ID3}$, as shown in FIG. 22.

The next sequential step is the iteration step. To get the average cost of one iteration, C, it must be determined if all the samples are in the same class. If they are not, the selection calculation is done to choose a decision attribute. Then the sample set is partitioned.

In ID3, one scan is needed to test whether there is a single class label and to generate $S_{ij}$. Suppose there are k candidate attributes for the current selection. Then, $C_{ID3}=C+k*(S+G)$.

Using PC-trees, the creation of sub-sample sets is not necessary. If B is a candidate for the current decision attribute either $k_B$ basic PC-trees, the PC-tree of the class label defining the sub-sample set need only be ANDed with each of the $k_B$ basic PC-trees. If the PC-tree of the current sample set is $P_{2,\,0100} \char`\^ P_{3,\,0001}$, for example, and the current attribute is B1 (with, for example, 2 bit values), then $P_{2,\,0100} \char`\^ P_{3,\,0001} \char`\^ P_{1,\,00}$, $P_{2,\,0100} \char`\^ P_{3,\,0001} \char`\^ P_{1,\,01}$, $P_{2,\,0100} \char`\^ P_{3,\,0001} \char`\^ P_{1,\,10}$ and $P_{2,\,0100} \char`\^ P_{3,\,0001} \char`\^ P_{1,\,11}$ identifies the partition of the current sample set. To generate Sij, only PC-tree ANDings are required. As for the gain calculation, the cost is the same as in ID3 technique. Thus, $C_{PCT}=k*(P+G)$.

Figure 23:
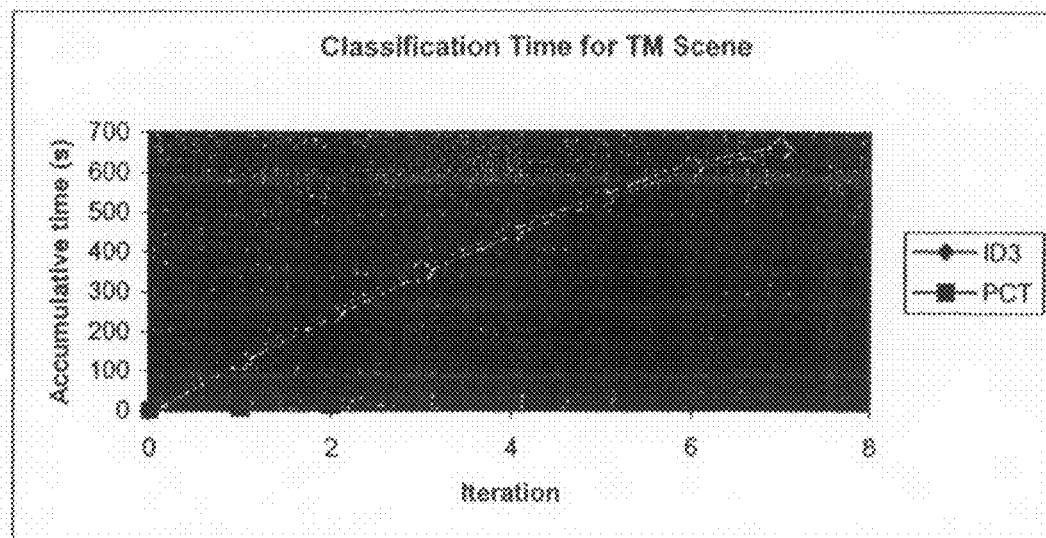
FIG. 23 depicts accumulative time with respect to iteration for the ID3 and PC-tree techniques.
Figure 24:
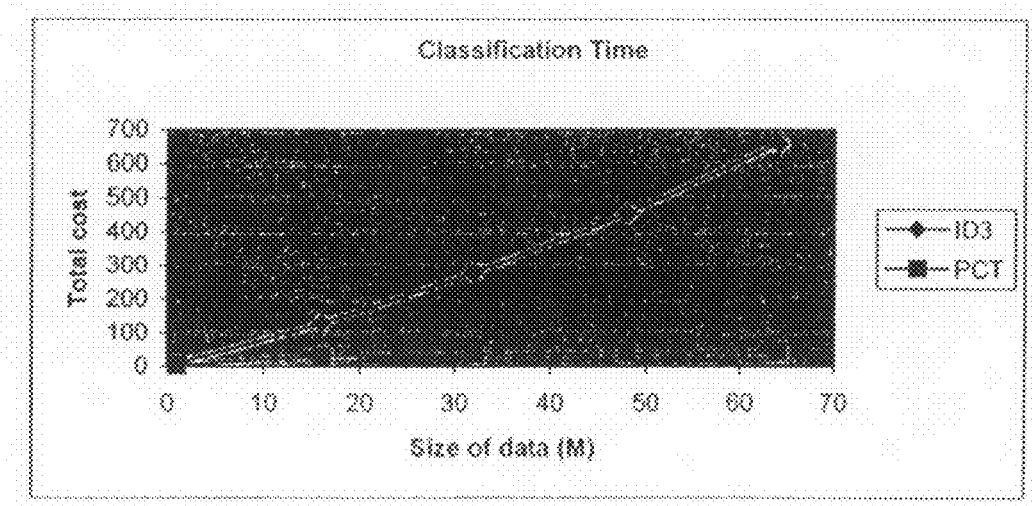
FIG. 24 depicts the classification cost with respect to dataset size for the ID3 and PC-tree techniques.

In FIG. 22, P and S are compared. Now it is necessary to compare $C_{PCT}$ and $C_{ID3}$. Since $T_{PCT}<T_{ID3}$ and $C_{PCT}<C_{ID3}$, it is concluded that the entire cost $COST_{PCT}<COST_{ID3}$. FIGS. 23 and 24 give the numbers for comparing learning time with respect to the number of iterations and dataset size using ID3 and PC-tree techniques. FIG. 23 gives the accumulative time with respect to iteration, while FIG. 24 gives classification cost with respect to the dataset size.

Described above is a new approach to decision tree induction which is especially useful for the classification on spatial data. The data organization, bit Sequential organization (bSQ) and a lossless, data-mining ready data structure, and the Peano Count tree (PC-tree) of the present invention are utilized to represent the information needed for classification in an efficient and ready-to-use form. The rich and efficient PC-tree storage structure and fast PC-tree algebra, facilitate the development of a very fast decision tree induction classifier. The PC-tree decision tree induction classifier is shown to improve classifier development time significantly. For the very large datasets available today, this is a very important issue. The particular advantages of the PC-tree approach include:

1. PC-trees contain 1-count for every quadrant of every dimension (they are data-mining ready).
2. The PC-tree for any sub-quadrant at any level is simple to extract (it need not be rebuilt).
3. The PC-tree is a run-length compression of the bit-band with significant compression ratios for most images.
4. Basic PC-trees can be combined to produce any needed data structure, including the original data (lossless).
5. Incremental ANDing of PC-trees produces immediate and incrementally improving upper/lower bounds for counts.

PC-trees can be used to smooth the data using bottom-up quadrant purification (bottom-up replacement of mixed counts with their closest pure counts).

Other PC-tree-based classification techniques already developed are a K-Nearest Neighbor (KNN) method and a Bayesian Method (BAY). The Bayesian Method involves applying Baye's law to the prior probabilities in exactly the same was as the classical Bayes method. However, all probabilities are computed directly from the counts provided immediately by the PC-tree or its variants and no naïve assumption need be made regarding the conditional probabilities. Therefore, BAY is both faster and more accurate than the classical Naïve Bayesian classification.

In a K-nearest neighbor (KNN) classification method, the k-nearest neighbors (under some distance metric), of the sample to be classified, are found by scanning the entire data set. Then the predominant class in that neighbor-set is assigned to the sample. KNN methods are desirable methods since no residual "classifier" needs to be built ahead of time (during the training phase). Therefore KNN methods work well for data streams or in other settings where new training data is continually arriving. The problem with classical KNN methods is that they are slower. Since there is not pre-computed "classifier" ready for use, at least one complete data set scan is required. PC-tree KNN requires no data set scan. From the basic PC-trees, ever larger rectangle-PC-trees are constructed centered on the sample to be classified (one OR operation applied to all tuple-PC-trees each of whose attribute values is a distance of 1, then 2, then 3, etc, from the sample). PC-tree KNN is therefore very fast. It has also been shown to be more accurate than existing KNN methods. The reason is very simple. Existing methods build the K-neighborhood by using ever increasing diameters under a Minkowski metric $(d(x,y)=(\Sigma(w_i^*|x_i-y_i|^q)^{1/q}$, where $w_i$'s are weights—usually all 1's). Minkowski metrics include almost all possible metrics depending on the choice of q (including the walking metric (q=1), the Euclidean metric (q=2) and any weighted variations of these metrics). PC-tree-KNN is equivalent, with respect to the resulting neighbor set, to a metric method also. However this metric, which would properly be called a "rotated walking metric" is not one of the Minkowski metrics, in fact, the distance it generates is the limit of the distances generated by the Minkowski metrics as q advances toward infinity. In practice one must choose a particular value for q, and the larger the value of q, the closer the neighbor-set is to the PC-tree KNN neighbor-set. However, no matter how large q is chosen to be, there will always be some difference. Our studies have shown that the accuracy of Minkowski-q KNN methods increases as q increases and the limiting accuracy is achieved by our PC-tree KNN method. Intuitively, the reason for the superiority of the (q→infinity)-Minkowski (or rotated walking metric) its neighborhoods have better clustering for discrete values than the others.

PC-Tree KNN Classification

The PC-tree KNN classification method is described in detail herein below. As mentioned earlier, classification of spatial data has become important due to the fact that there are huge volumes of spatial data now available holding a wealth of valuable information, the situation wherein the training dataset changes often is considered herein. New training data arrive continuously and are added to the training set. For these types of data streams, building a new classifier each time can be very costly with most techniques. In this situation, k-nearest neighbor (KNN) classification is a very good choice, since no residual classifier needs to be built ahead of time. For that reason KNN is called a lazy classifier. KNN is extremely simple to implement and lends itself to a wide variety of variations. The traditional k-nearest neighbor classifier finds the k nearest neighbors based on some distance metric by finding the distance of the target data point from the training dataset, then finding the class from those nearest neighbors by some voting mechanism. There is a problem associated with KNN classifiers. They increase the classification time significantly relative to other non-lazy methods.

To overcome this problem, the present invention includes a new method of KNN classification for spatial data streams using a new, rich, data-mining-ready structure, the Peano-count-tree or PC-tree. In the new method, logical AND/OR operations are performed on PC-trees to find the nearest neighbor set of a new sample and to assign the class label. The method includes fast and efficient methods for AND/OR operations on PC-trees, which reduce the classification time significantly, compared with traditional KNN classifiers. Instead of taking exactly k nearest neighbors the present methods finds the smallest distance-closed set (based on new Hobbit or Hawaiian metrics) with k neighbors (include all neighbors of equal distance to that of any of the k neighbors). Test results of the PC-tree KNN method show that it yields higher classification accuracy as well as significantly higher speed than classical KNN.

Classification is the process of finding a set of models or functions that describes and distinguishes data classes or concepts for the purpose of predicting the class of objects whose class labels are unknown. The derived model is based on the analysis of a set of training data whose class labels are known. Consider each training sample has n attributes: A1, A2, A3, . . . , An−1, C, where C is the class attribute which defines the class or category of the sample. The model associates the class attribute, C, with the other attributes. Now consider a new tuple or data sample whose values for the attributes A1, A2, A3, . . . , An−1 are known, while for the class attribute is unknown. The model predicts the class label of the new tuple using the values of the attributes A1, A2, A3, . . . , An−1.

There are various techniques for classification such as Decision Tree Induction, Bayesian Classification, and Neural Networks Unlike other common classification methods, a k-nearest neighbor classification (KNN classification) does not build a classifier in advance. That is what makes it suitable for data streams. When a new sample arrives, KNN finds the k neighbors nearest to the new sample from the training space based on some suitable similarity or closeness metric. A common similarity function is based on the Euclidian distance between two data tuples. For two tuples, $X=(x, x_2, x_3, \ldots x_{n-1})$ and $Y=(y_1, y_2, y_3, \ldots y_{n-1})$ (excluding the class labels), the Euclidian similarity function is $$d_2(X, Y) = \sqrt{\sum_{i=1}^{n-1} (x_i - y_i)^2}.$$

A generalization of the Euclidean function is the Minkowski similarity function $$d_q(X, Y) = \sqrt[q]{\sum_{i=1}^{n-1} w_i |x_i - y_i|^q}$$

The Euclidean function results by setting q to 2 and each weight, $w_i$, to 1. The Manhattan distance, result by setting q to ∞. Setting q to infinity results in the max function (the max function is the limit of the q functions and is $$d_\infty(X, Y) = \max_{i=1}^{n-1} |x_i - y_i|.$$

After finding the k nearest tuples based on the selected distance metric, the plurality class label of those k tuples can be assigned to the new sample as its class. If there is more than one class label in plurality, one of them can be chosen arbitrarily.

In the PC-tree KNN classification method a new metric is introduced called called Higher Order Bit Similarity (HOBS) metric HOBS provides an efficient way of computing neighborhoods while keeping the classification accuracy very high.

Nearly every other classification model trains and tests a residual "classifier" first and then uses it on new samples. KNN does not build a residual classifier, but instead, searches again for the k-nearest neighbor set for each new sample. This approach is simple and can be very accurate. It can also be slow (the search may take a long time). KNN is a good choice when simplicity and accuracy are the predominant issues. KNN can be superior when a residual, trained and tested classifier has a short useful lifespan, such as in the case with data streams, where new data arrives rapidly and the training set is ever changing. For example, in spatial data, AVHRR images are generated in every one hour and can be viewed as spatial data streams. The PC-tree KNN classification method of the present invention can be used on these data streams because it is not only simple and accurate but is also fast enough to handle spatial data stream classification.

In describing the PC-tree KNN classification, the following are preferably kept in mind. The PC-tree KNN classification method, as applied to spatial data, uses PC-trees. PC-trees, as described earlier in the application, are new, compact, data-mining-ready data structures, which provide a lossless representation of the original spatial data. A space to be represented by a 2-dimensional array of locations (though the dimension could just as well be 1 or 3 or higher). Associated with each location are various attributes, called bands, such as visible reflectance intensities (blue, green and red), infrared reflectance intensities (e.g., NIR, MIR1, MIR2 and TIR) and possibly other value bands (e.g., crop yield quantities, crop quality measures, soil attributes and radar reflectance intensities). One band such as yield band can be the class attribute. The location coordinates in raster order constitute the key attribute of the spatial dataset and the other bands are the non-key attributes. A location is referred to as a pixel Using PC-trees, two methods are presented, one based on the max distance metric and the other based on the new HOBS distance metric. HOBS is the similarity of the most significant bit positions in each band. It differs from pure Euclidean similarity in that it can be an asymmetric function depending upon the bit arrangement of the values involved. However, it is very fast, very simple and quite accurate. Instead of using exactly k nearest neighbor (a KNN set), the method builds a closed-KNN set and performs voting on this closed-KNN set to find the predicting class. Closed-KNN, a superset of KNN, is formed by including the pixels, which have the same distance from the target pixel as some of the pixels in KNN set. Based on this similarity measure, finding nearest neighbors of new samples (pixel to be classified) can be done easily and very efficiently using PC-trees and higher classification accuracy than traditional methods on considered datasets was found.

In the original k-nearest neighbor (KNN) classification method, no classifier model is built in advance. KNN refers back to the raw training data in the classification of each new sample. Therefore, one can say that the entire training set is the classifier. The basic idea is that the similar tuples most likely belongs to the same class (a continuity assumption). Based on some pre-selected distance metric (some commonly used distance metrics are discussed in introduction), it finds the k most similar or nearest training samples of the sample to be classified and assign the plurality class of those k samples to the new sample. The value for k is pre-selected. Using relatively larger k may include some pixels not so similar pixels and on the other hand, using very smaller k may exclude some potential candidate pixels. In both cases the classification accuracy will decrease. The optimal value of k depends on the size and nature of the data. The typical value for k is 3, 5 or 7. The steps of the classification process are: 1) Determine a suitable distance metric. 2) Find the k nearest neighbors using the selected distance metric. 3) Find the plurality class of the k-nearest neighbors (voting on the class labels of the NNs). 4) Assign that class to the sample to be classified.

Two different methods using PC-trees, based two different distance metrics max (Minkowski distance with q=infinity) and our newly defined Hobbit are provided. Instead of examining individual pixels to find the nearest neighbors, here, the initial neighborhood (neighborhood is a set of neighbors of the target pixel within a specified distance based on some distance metric, not the spatial neighbors, neighbors with respect to values) with the target sample and then successively expand the neighborhood area until there are k pixels in the neighborhood set. The expansion is done in such a way that the neighborhood always contains the closest or most similar pixels of the target sample. The different expansion mechanisms implement different distance functions. Distance metrics and expansion mechanisms are described in detail below.

Of course, there may be more boundary neighbors equidistant from the sample than are necessary to complete the k nearest neighbor set, in which case, one can either use the larger set or arbitrarily ignore some of them. To find the exact k nearest neighbors one has to arbitrarily ignore some of them.

Figure 25:
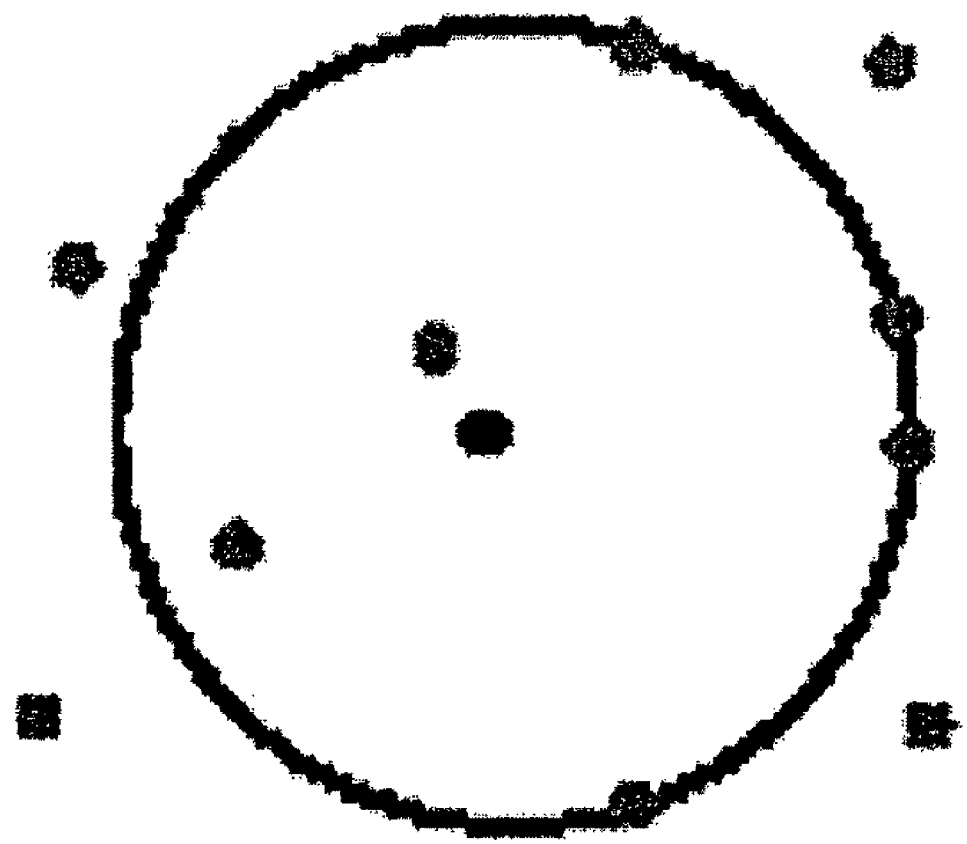
FIG. 25 depicts an example KNN set.

Instead a new approach is proposed of building nearest neighbor (NN) set, where the closure of the k-NN set is taken, that is, all of the boundary neighbors are included and it is called the closed-KNN set. Obviously closed-KNN is a superset of KNN set. In the example of FIG. 25, with k=3, KNN includes the two points inside the circle and any one point on the boundary. The closed-KNN includes the two points in side the circle and all of the four boundary points. The inductive definition of the closed-KNN set is given below.

Definition: a) if x in KNN, then x in closed-KNN
  b) if x in closed-KNN and d(T,y) LessOrEqual d(T,x), then y in closed-KNN. Where, d(T,x) is the distance of x from target T.
  c) closed-KNN doesn't contain any pixel which can not be produced by step a and b.

Test results show closed-KNN yields higher classification accuracy than KNN does. The reason is if for some target there are many pixels on the boundary, they have more influence on the target pixel. While all of them are in the nearest neighborhood area, inclusion of one or two of them does not provide the necessary weight in the voting mechanism. One may argue that then why isn't a higher k used? For example using k=5 instead of k=3. The answer is if there are too few points (for example only one or two points) on the boundary to make k neighbors in the neighborhood, the neighborhood has to be expanded and include some not so similar points which will decrease the classification accuracy. Closed-KNN is constructed only by including those pixels, which are in as same distance as some other pixels in the neighborhood without further expanding the neighborhood. To perform our tests, the optimal k is found (by trial and error method) for that particular dataset and then using the optimal k, both KNN and closed-KNN were performed and higher accuracy was found for PC-tree-based closed-KNN method. The test results are given below. In the PC-tree implementation, no extra computation is required to find the closed-KNN. The expansion mechanism of nearest neighborhood automatically includes the points on the boundary of the neighborhood.

Also, there may be more than one class in plurality (if there is a tie in voting), in which case one can arbitrarily chose one of the plurality classes. Unlike the traditional k-nearest neighbor classifier the present classification method doesn't store and use raw training data. Instead, the data-mining-ready PC-tree structure is used, which can be built very quickly from the training data. Without storing the raw data the basic PC-trees are created and stored for future classification purpose. Avoiding the examination of individual data points and being ready for data mining these PC-trees not only save classification time but also save storage space, since data is stored in compressed form. This compression technique also increases the speed of ANDing and other operations on PC-trees tremendously, since operations can be performed on the pure0 and pure1 quadrants without reference to individual bits, since all of the bits in thosequadrant are the same.

Expansion of Neighborhood and Distance or Similarity Metrics: Similarity and distance can be measured by each other—more distance less similar and less distance more similar. The present similarity metric is the closeness in numerical values for corresponding bands. We begin searching for nearest neighbors by finding the exact matches i.e. the pixels having as same band-values as that of the target pixel. If the number of exact matches is less than k, we expand the neighborhood. For example, for a particular band, if the target pixel has the value a, we expand the neighborhood to the range [a-b, a+c], where b and c are positive integers and find the pixels having the band value in the range [a-b, a+c]. We expand the neighbor in each band (or dimension) simultaneously. We continue expanding the neighborhood until the number pixels in the neighborhood is greater than or equal to k. We develop the following two different mechanisms, corresponding to max distance (Minqowski distance with $q=\infty$ or $L_\infty$) and our newly defined Hobbit distance, for expanding the neighborhood. The two given mechanisms have trade off between execution time and classification accuracy.

Higher Order Bit Similarity (HOBS): A new similarity metric is presented where similarity in the most significant bit positions between two band values is used. The metric considers only the most significant consecutive bit positions starting from the left most bit, which is the highest order bit. Consider the following two values, x1 and y1, represented in binary. The 1st bit is the most significant bit and 8th bit is the least significant bit.

| | Bit Position: | | |
|---|---|---|---|
| | 1 2 3 4 5 6 7 8 | | 1 2 3 4 5 6 7 8 |
| $x_1$: | 0 1 1 0 1 0 0 1 | $x_1$: | 0 1 1 0 1 0 0 1 |
| $y_1$: | 0 1 1 1 1 1 0 1 | $y_x$: | 0 1 1 0 0 1 0 0 |

These two values are similar in the three most significant bit positions, 1st, 2nd and 3rd bits (011). After they differ (4th bit), we don't consider anymore lower order bit positions though x1 and y1 have identical bits in the 5th, 7th and 8th positions. Since we are looking for closeness in values, after differing in some higher order bit positions, similarity in some lower order bit is meaningless with respect to our purpose. Similarly, x1 and y2 are identical in the 4 most significant bits (0110). Therefore, according to our definition, x1 is closer or similar to y2 than to y1.

Definition: The similarity between two values A and B is defined by $$HOBS(A,B) = \max\{s | i \leq s \Rightarrow a_i = b_i\}$$

Or in another way, HOBS(A,B)=s, where for all $i \leq s$, $a_i = b_i$ and $a_{s+1} \neq b_{s+1}$. $a_i$ and $b_i$ are the ith bits of A and B respectively.

Definition: The Hobbit (High order bifurcation bit) or POI (Position Of Inequality) or Hawaiian distance between the values A and B is defined by $$d_v(A,B) = m - HOBS(A,B)$$

m is the number of bits in binary representations of the values. All values must be represented using the same number of bits.

Definition: The distance between two pixels X and Y is defined by $$d_p(X, Y) = \max_{i=1}^{n-1}\{d_v(x_i, y_i)\} = \max_{i=1}^{n-1}\{n - HOBS(x_i, y_i)\}$$

n is the total number of bands where one of them (the last band) is class attribute that we don't use for measuring similarity.

To find the closed-KNN set, first we look for the pixels, which are identical to the target pixel in all 8 bits of all bands i.e. the pixels, X, having distance from the target T, $d_p(X,T)=0$. If, for instance, $x_1=105$ ($01101001_b=105_d$) is the target pixel, the initial neighborhood is [105, 105] ([01101001, 01101001]). If the number of matches is less than k, we look for the pixels, which are identical in the 7 most significant bits, not caring about the 8th bit, i.e. pixels having $d_p(X,T) \leq 1$. Therefore our expanded neighborhood is [104,105] ([01101000, 01101001] or [0110100-, 0110100-]—don't care about the 8th bit). Removing one more bit from the right, the neighborhood is [104, 107] ([011010-, 011010-]—don't care about the 7th or the 8th bit). Continuing to remove bits from the right we get intervals, [104, 111], then [96, 111] and so on. Computationally this method is very cheap (since the counts are just the root counts of individual PC-trees, all of which can be constructed in one operation). However, the expansion does not occur evenly on both sides of the target value (note: the center of the neighborhood [104, 111] is (104+111)/2=107.5 but the target value is 105). Another observation is that the size of the neighborhood is expanded by powers of 2. These uneven and jump expansions include some not so similar pixels in the neighborhood keeping the classification accuracy lower. But P-tree-based closed-KNN method using this HOBS metric still outperforms KNN methods using any distance metric where as this method is the fastest.

To improve accuracy further another method is provided called perfect centering avoiding uneven and jump expansion. Although, in terms of accuracy, perfect centering outperforms HOBS, in terms of computational speed it is slower than HOBS.

Perfect Centering: In this method the neighborhood is expanded by 1 on both the left and right side of the range keeping the target value always precisely in the center of the neighborhood range. We begin with finding the exact matches as we did in HOBS method. The initial neighborhood is [a, a], where a is the target band value. If the number of matches is less than k we expand it to [a−1, a+1], next expansion to [a−2, a+2], then to [a−3, a+3] and so on.

Perfect centering expands neighborhood based on max distance metric or $L_\infty$ metric, Minkowski distance (discussed in introduction) metric setting q=infinity.

$$d_\infty(X, Y) = \max_{i=1}^{n-1}|x_i - y_i|$$

In the initial neighborhood $d_\infty(X,T)$ is 0, the distance of any pixel X in the neighborhood from the target T. In the first expanded neighborhood [a−1, a+1], $d_\infty(X,T) \leq 1$. In each expansion $d_\infty(X,T)$ increases by 1. As distance is the direct difference of the values, increasing distance by one also increases the difference of values by 1 evenly in both side of the range without any jumping. This method is computationally a little more costly because we need to find matches for each value in the neighborhood range and then accumulate those matches but it results better nearest neighbor sets and yields better classification accuracy. These two techniques are compared later, below Computing the Nearest Neighbors: We have the basic PC-trees of all bits of all bands constructed from the training dataset and the new sample to be classified. Suppose, including the class band, there are n bands or attributes in the training dataset and each attribute is m bits long. In the target sample we have n−1 bands, but the class band value is unknown. Our goal is to predict the class band value for the target sample. Pi,j is the P-tree for bit j of band i. This P-tree stores all the jth bit of the ith band of all the training pixels. The root count of a P-tree is the total counts of one bits stored in it. Therefore, the root count of Pi,j is the number of pixels in the training dataset having 1 value in the jth bit of the ith band. P'i,j is the complement P-tree of Pi,j. P'i,j stores I for the pixels having a 0 value in the jth bit of the ith band and stores 0 for the pixels having a 1 value in the jth bit of the ith band. Therefore, the root count of P'i,j is the number of pixels in the training dataset having 0 value in the jth bit of the ith band. Now let, bij=jth bit of the ith band of the target pixel.

$$\text{Define} \quad Pt_{i,j} = P_{i,j}, \quad \text{if } b_{i,j} = 1$$
$$= P'_{i,j}, \quad \text{otherwise}$$

We can say that the root count of Pti,j is the number of pixels in the training dataset having as same value as the jth bit of the ith band of the target pixel.

Let, Pvi,1−j=Pti,1 & Pti,2 & Pti,3 & . . & Pti,j, here & is the PC-tree AND operator.

Pvi,1−j counts the pixels having as same bit values as the target pixel in the higher order j bits of ith band.

Using higher order bit similarity, first we find the PC-tree Pnn=Pv1,1-8 & Pv2,1-8 & Pv3,1-8 & . . & Pvn−1,1-8, where n−1 is the number of bands excluding the class band. Pnn represents the pixels that exactly match the target pixel. If the root count of Pnn is less than k we look for higher order 7 bits matching, i.e., we calculate Pnn=Pv1,1-7 & Pv2,1-7 & Pv3, 1-7 & . . & Pvn−1,1-7. Then we look for higher order 6 bits matching and so on. We continue as long as root count of Pnn is less than k. Pnn represents closed-KNN set, i.e., the training pixels having the same bits in corresponding higher order bits as those in target pixel, and the root count of Pnn is the number of such pixels, the nearest pixels. A 1 bit in Pnn for a pixel means that pixel is in closed-KNN set and a 0 bit means the pixel is not in the closed-KNN set. The method for finding nearest neighbors is given immediately below.

Method to Find the P-tree representing Closed-KNN set based on HOBS Metric

Input Pij for all i and j, basic Ptrees of all the bits of all bands of the training dataset and bij for all i and j, the bits for the target pixels.

Output: Pnn, the Ptree representing the nearest neighbors
of the target pixel.
// n is the number of bands where nth band is the class
band
// m is the number of bits in each band (assumed uniform)

```
FOR i = 1 TO n − 1 DO
    FOR j = 1 TO m DO
        IF bij = 1 Ptij ←− Pij
        ELSE Ptij ←− P'ij
FOR i = 1 TO n − 1 DO
    Pvij ←− Ptij
    FOR j = 2 TO m DO
        Pvij ← Pvij−1 & Ptij
s ← m // first check matching in all m bits
REPEAT
    Pnn ← Pvis
    FOR r = 2 TO n − 1 DO
        Pnn ← Pnn & Pvrs
    s ← s − 1
UNTIL RootCount (Pnn) ≥ k
```

For Perfect Centering: Let vi is the value of the target pixels for band i. Pi(vi) is the value P-tree for the value vi in band i. Pi(vi) represents the pixels having value vi in band i. For finding the initial nearest neighbors (the exact matches) using perfect centering we find Pi(vi) for all i.

The ANDed result of these value P-trees i.e. Pnn=P1(v1) & P2(v2) & P3(v3) & .. & Pn−1(vn−1) represents the pixels having the same values in each band as that of the target pixel. A value P-tree, Pi(vi), can be computed by finding the P-tree representing the pixels having the same bits in band i as the bits in value vi. That is, if Pti,j=Pi,j, when bi,j=1 and Pti,j=P'i,j, when bi,j=0 (bi,j is the jth bit of value vi), then Pi(vi)= Pti,1 & Pti,2 & Pti,3 & ... & Pti,m, m is the number of bits in a band. The method for computing value PC-trees is given immediately below.

Finding P-tree reprenting closed-KNN set using the max distance metric (perfect centering)

Input Pij for all i and j, basic Ptrees of all the bits of all bands of the training dataset and vi for all i, the band values for the target pixel.

Output: Pnn, the Ptree representing the closed-KNN set.
// n is the number of bands where nth band is the class band
// m is the number of bits in each band (assumed uniform)

```
FOR i = 1 TO n − 1 DO
    Pvi ← Pivi
    Pnn ← Pv1
FOR i = 2 TO n − 1 DO
    Pnn ← Pnn & Pvi // initial neighborhood
```

-continued
```
for exact match d ← 1 // distance for the first expansion
WHILE RootCount (Pnn) < k DO
    FOR i = 1 TO n − 1 DO
        Pvi ← Pvi|Pi(vi − d)|Pi(vi + d) // neighborhood expansion
    Pnn ← Pv1 // '|' is the P-tree OR operator
    FOR i = 2 TO n − 1 DO
        Pnn ← Pnn & Pvi // updating closed-KNN set
    d ← d + 1
```

Method for Finding Value PC-tree

Input Pij for all j, basic Ptrees of all bits of band i and value vi for band i.

Output Pivi the value-P-tree for value vi

// m=number of bits in each band; bij is jth bit of value vi.

```
FOR j = 1 TO m DO
    IF bij = 1 Ptij ← Pij
    ELSE Ptij ← P'ij
Pi(v) ← Pti1
FOR j = 2 TO m DO
    Pi(v) ← Pi(v) & Ptij
```

If the number of exact matching i.e. root count of Pnn is less than k, we expand neighborhood along each dimension. For each band i, we calculate range P-tree Pri=Pi(vi−1)|Pi(vi)|Pi (vi+1). '|' is the P-tree OR operator. Pri represents the pixels having a value either vi−1 or vi or vi+1 i.e. any value in the range [vi−1, vi+1] of band i. The ANDed result of these range P-trees, Pri for all i, produce the expanded neighborhood, the pixels having band values in the ranges of the corresponding bands. We continue this expansion process until root count of Pnn is greater than or equal to k. See method immediately above for finding value P-tree.

Finding the plurality class among the nearest neighbors: For the classification purpose, we don't need to consider all bits in the class band. If the class band is 8 bits long, there are 256 possible classes. Instead of considering 256 classes we partition the class band values into fewer groups by considering fewer significant bits. For example if we want to partition into 8 groups we can do it by truncating the 5 least significant bits and keeping the most significant 3 bits. The 8 classes are 0, 1, 2, 3, 4, 5, 6 and 7. Using these 3 bits we construct the value P-trees Pn(0), Pn(1), Pn(2), Pn(3), Pn(4), Pn(5), Pn(6), and Pn(7).

A 1 value in the nearest neighbor P-tree, Pnn, indicates that the corresponding pixel is in the nearest neighbor set. An 1 value in the value P-tree, Pn(i), indicates that the corresponding pixel has the class value i. Therefore Pnn & Pn(i) represents the pixels having a class value i and are in the nearest neighbor set. An i which yields the maximum root count of Pnn & Pn(i) is the plurality class. The method is provided immediately below.

Method for Finding the Plurality Class
Input: Pn(i), the value P-tree for all class i and the closed-KNN P-tree, Pnn
Output: Pnn, the P-tree representing the nearest neighbors of the target pixel
//c is the number of different classes class ← 0

← Pnn & Pn(0)

rc ← RootCount(P)

FOR i = 1 TO c − 1 DO

P ← Pnn & Pn(i)

IF rc < RootCount(P)

rc ← RootCount(P)

class ← i

Performance Analysis Tests were performed on two sets of Arial photographs of Best Management Plot (BMP) of Oaks Irrigation Test Area (OITA) in Oaks city of North Dakota The latitude and longitude of the place are 45 deg 49'15"N and 97 deg 42'18"W respectively. The two images "29NW083097.tiff" and "29NW082598.tiff" were taken in 1997 and 1998 respectively. Each image contains 3 bands, red, green and blue reflectance values. In other three separate files synchronized soil moisture, nitrate and yield values are available. Soil moisture and nitrate are measured using shallow and deep well lysemeter and yield values are collected by using GPS yield monitor and harvesting equipments.

Among those 6 bands we consider the yield as class attribute. For test purpose we used datasets with four attributes or bands—red, green, blue reflectance value and soil moitureyield (the class attribute). Each band is 8 bits long. So we have 8 basic P-trees for each band and 40 in total. For the class band yield we considered only most significant 3 bits. Therefore we have 8 different class labels for the pixels. We build 8 value P-trees from the yield values—one for each class label. The original image is 1320×1320.

Figure 26:
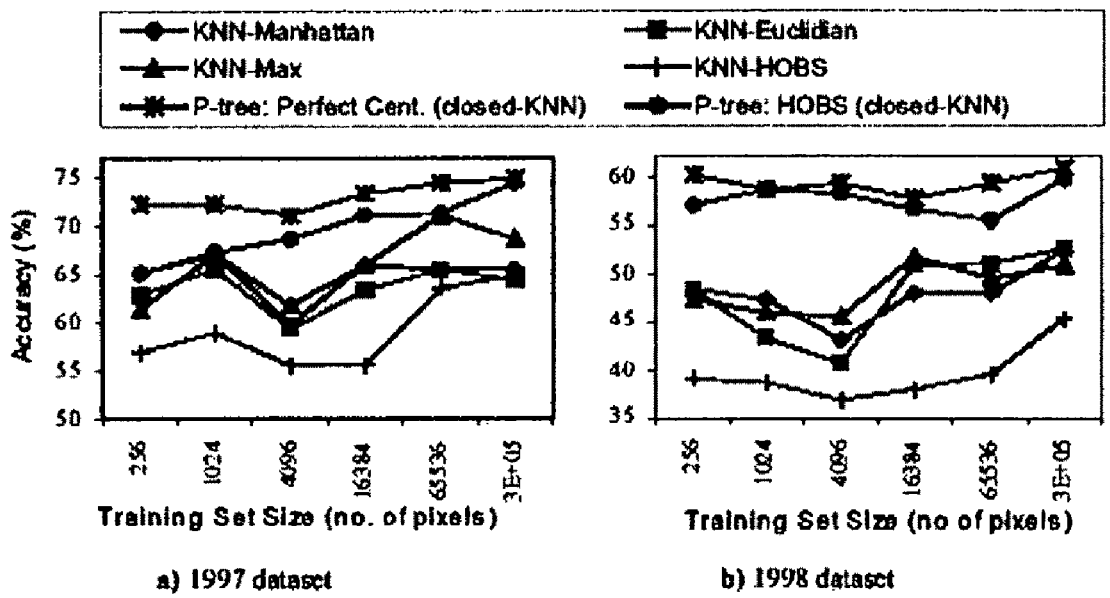
FIG. 26 is a graph depicting classification accuracy for different dataset size.

We implemented the classical KNN classifier with Euclidian distance metric and two different KKN classifier using PC-trees—one with higher order bit similarity and another with perfect centering. Both classifiers outperform the classical KNN classifier in terms of both classification time and accuracy. We tested the methods using different datasets with different sizes. FIG. 26 depicts the classification accuracy for different dataset sizes for traditional KNN, PC-tree with HOBS, and PC-tree with Perfect Centering.

The simultaneous search for closeness in all attributes instead of using one mathematical closeness function (such as Euclidian distance metric used by traditional KNN) yields better nearest neighbors hence better classification accuracy. One observation is that for all of the three methods classification accuracy goes down slightly when training dataset size increases. As discussed earlier the perfect centering method finds better nearest neighbors than that of higher order bit similarity method and a little bit higher accuracy was found in perfect centering.

The disadvantage of perfect centering is that the computational cost for this method is higher than that of higher order bit similarity method. But both of the methods are faster than traditional KNN for any size of datasets For the presented methods, time increases with dataset size in a lower rate than that of the traditional KNN. The reason is that as dataset size increases, there are more and larger pure-0 and pure-1 quadrant in the P-trees, which increases the efficiency of the ANDing operations. So the presented methods are more scalable than traditional KNN Podium Incremental Neighbor Evaluator (PINE) for Classifying Spatial Data Nearest neighbor classification is a lazy classifier. Given a set of training data, a k-nearest neighbor classifier predicts the class value for an unknown tuple X by searching the training set for the k nearest neighbors to X and then assigning to X the most common class among its k nearest neighbors.

In classical k-nearest neighbor (KNN) methods, each of the k nearest neighbors casts an equal vote for the class of X. However, by virtue of the present invention it has been found that the accuracy can be increased by weighting the vote of different neighbors. Based on this, the following describes a method of the present invention, called Podium Incremental Neighbor Evaluator (PINE), to achieve high accuracy by applying a podium function on the neighbors.

The idea of distance weighting is not new. For example, the concept of a "radial basis function" is related to the idea of podium function. However, applying the podium function to the nearest neighbor classification is something that has not been achieved heretofore.

Unlike other nearest neighbor classifiers, in PINE, no sub-sampling is done and no limit is placed on the number of neighbors, as in classical k-nearest neighbor classification techniques. The podium or distance weighting function (which can be user parameterized) establishes a riser height for each step of the podium weighting function as the distance from the sample grows. This approach gives users maximum flexibility in choosing just the right level of influence for each training sample in the entire training set.

Different metrics can be defined for "closeness" of two data points. Hereinbelow, a metric, called HOBBit (High Order Basic Bit similarity), for spatial data is used. In addition, the Peano Count Tree (PC-tree), a data structure, is used for efficient discovery of nearest neighbors, without scanning the database. PC-trees are a data mining-ready representation of integer-valued data. Count information is maintained to quickly perform data mining operations. PC-trees represent bit information that is obtained from the data through a separation into bit planes. Their multi-level structure is chosen so as to achieve high compression. A consistent multi-level structure is maintained across all bit planes of all attributes. This is done so that a simple multi-way logical AND operation can be used to reconstruct count information for any attribute value or tuple.

DISTANCE-WEIGHTED (PODIUM) NEIGHBOR CLASSIFICATION USING P-TREES: In classical k-nearest neighbor classification techniques, there is a limit placed on the number of neighbors. In the present distance-weighted neighbor classification approach, the podium or distance weighting function (which can be user parameterized) establishes a riser height for each step of the podium weighting function as the distance from the sample grows. This approach gives users maximum flexibility in choosing just the right level of influence for each training sample in the entire training set. The real question is, can this level of flexibility be offered without imposing a severe penalty with respect to the speed of the classifier. Traditionally, sub-sampling, neighbor-limiting and other restrictions are introduced precisely to ensure that the algorithm will finish its classification in reasonable time. The use of the compressed, data-mining-ready data structure, the PC-tree, in fact, makes PINE even faster than traditional methods. This is critically important in classification since data are typically never discarded and therefore the training set will grow without bound. The classification technique must scale well or it will quickly become unusable in this setting. PINE scales well since its accuracy increases as the training set grows while its speed remains very reasonable (see the performance study below). Furthermore, since PINE is lazy (does not require a training phase in which a closed form classifier is pre-built), it does not incur the expensive delays required for rebuilding a classifier when new training data arrives. Thus, PINE gives us a faster and more accurate classifier.

Figure 27:
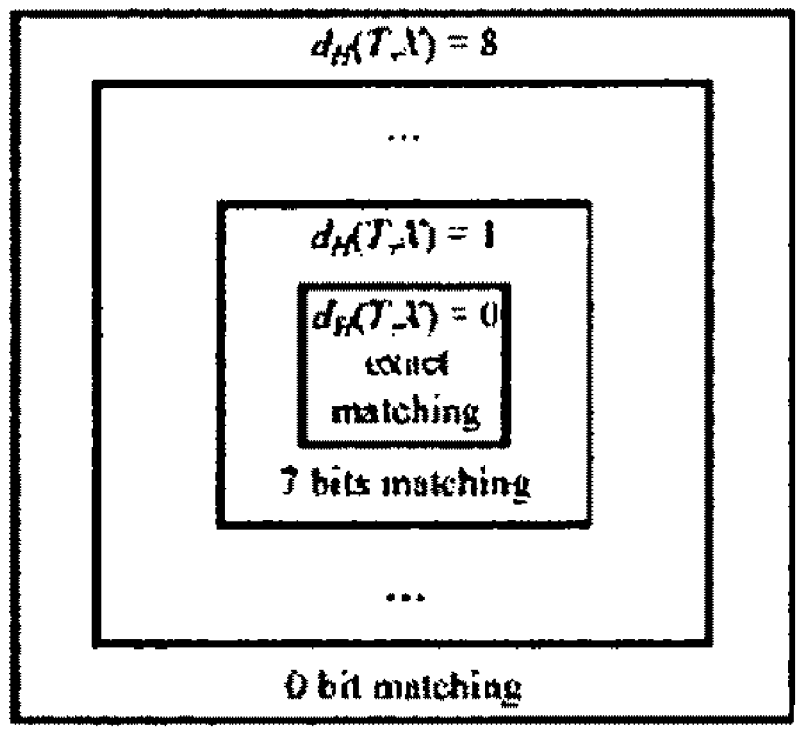
FIG. 27 depicts neighborhood rings using HOBBit.
Figure 28:
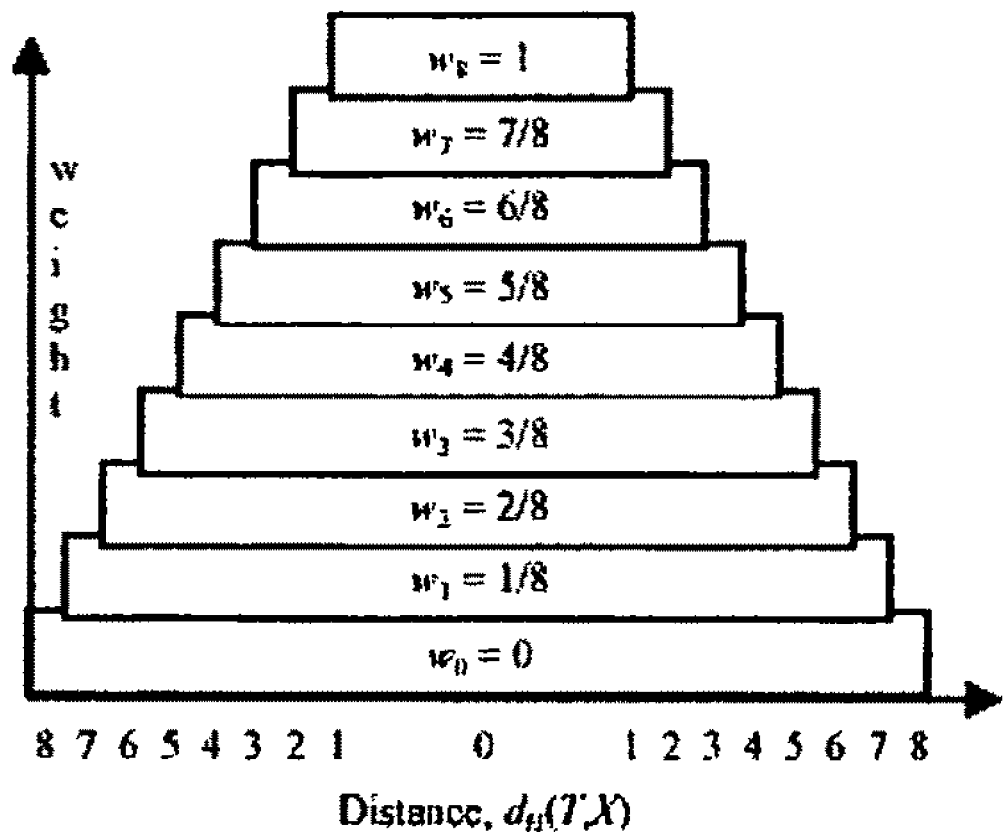
FIG. 28 depicts a linear podium function.

The continuity assumption of KNN (described earlier) tells us that tuples that are more similar to a given tuple have more influence on classification than tuples that are less similar. Therefore giving more voting weight to closer tuples than distant tuples increases the classification accuracy. Instead of considering the k nearest neighbors, we include all of the points, using the largest weight, 1, for those matching exactly, and the smallest weight, 0, for those furthest away. Many weighting functions which decreases with distance, can be used (e.g., Gaussian, Kriging, etc). Remaining consistent with the neighborhood rings, see FIG. 27, using the HOBBit distance, we can apply, for instance, a linear podium function, see FIG. 28, which decreases step-by-step with distance.

Note that the HOBBit distance metric is ideally suited to the definition of neighborhood rings, because the range of points that are considered equidistant grows exponentially with distance from the center. Adjusting weights is particularly important for small to intermediate distances where the podiums are small. At larger distances where fine-tuning is less important the HOBBit distance remains unchanged over a large range, i.e., podiums are wider. Ideally, the 0-weighted ring should include all training samples that are judged to be too far away (by a domain expert) to influence class.

We number the rings from 0 (outermost) to m (innermost). Let wj be the weight associated with the ring j. Let cij be the number of neighbor tuples in the ring j belonging to the class i. Then the total weight vote by the class i is given by:

$$V(i) = \sum_{j=0}^{m} w_j c_{ij}$$

This can easily be transformed to:

$$V(i) = w_0 \sum_{k=0}^{m} c_{il} + \sum_{j=1}^{m} \left\{ (w_j - w_{j-1}) \sum_{k=j}^{m} c_{ik} \right\}$$

Let circle j be the circle formed by the rings j, j+1, . . . , m, that is, the ring j including all of its inner rings. Referring to eq. 4, the P-tree, Pnn(j), represents all of the tuples in the circle j. Therefore, {Pnn(j) & Pn(i)} represents the tuples in the circle j and class i; Pn(i) is the P-tree for class i. Hence:

$$\sum_{k=j}^{m} c_{ik} = RC\{Pnn(j) \& Pn(i)\},$$

$$V(i) = w_0 RC\{Pnn(0) \& Pn(i)\} + \sum_{j=1}^{m} [(w_j - w_{j-1}) RC\{Pnn(j) \& Pn(i)\}]$$

An I which yields the maximum weighted vote, V(i), is the plurality class or the predicted class; that is:

$$\text{predicted class} = \arg \max_i \{V(i)\}.$$

PERFORMANCE ANALYSIS Tests have been performed to evaluate PINE on the real data sets including the aerial TIFF image (with Red, Green and Blue band reflectance values), moisture, nitrate, and yield map of the Oaks area in North Dakota. In these datasets yield is the class label attribute. Test sets and training sets were formed of equal size and KNN was tested with Manhattan, Euclidean, Max, and HOBBit distance metrics; and closed-KNN was tested with the HOBBit metric, and Podium Incremental Neighbor Evaluator (PINE). In PINE, HOBBit was used as the distance function and the Gaussian function was used as the podium function. We specify variance c as 2^4, and the function is exp(-2^(2*d))/(2*σ^2)), where d is the HOBBit distance. Therefore, the mapping is given in the Table below.

TABLE

Gaussian weighs as the function of HoBBit distance

| | HOBBit Distance | | | | | | | |
|---|---|---|---|---|---|---|---|---|
| | 0 | 1 | 2 | 3 | 4 | 5 | 6 | 7 |
| Gaussian weigh | 1.00 | 1.00 | 0.97 | 0.88 | 0.61 | 0.14 | 0.00 | 0.00 |

Figure 29:
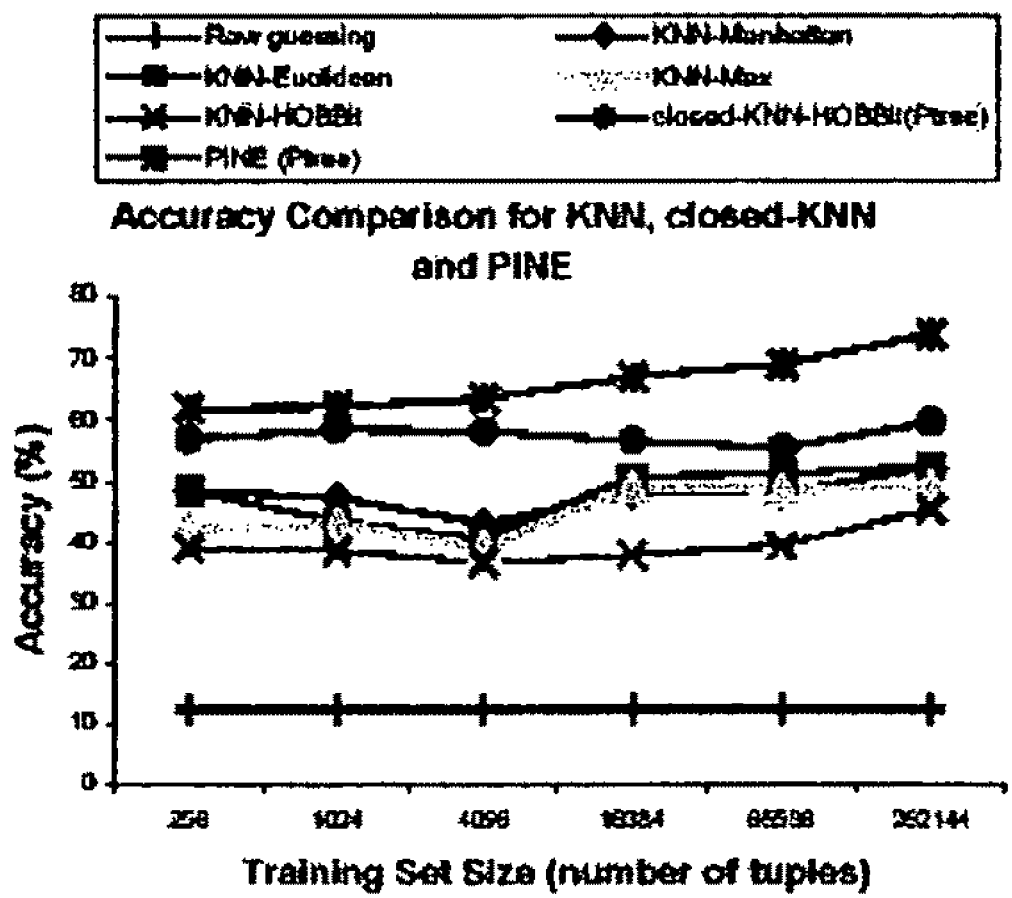
FIG. 29 is graph depicting accuracy comparison for KNN, closed-KNN and PINE using different metrics.

The accuracies of different implementations are given in FIG. 29 for one dataset. Similar results were obtained for other spatial datasets, which are consistent with our analysis about the properties of spatial data.

It can be seen that PINE performs better than closed-KNN as expected. Especially when the training set size increases, see FIG. 30, the improvement of PINE over closed-KNN is more apparent. All these classifiers work well compared to raw guessing, which is 12.5% in this data set with 8 class values.

Figure 30:
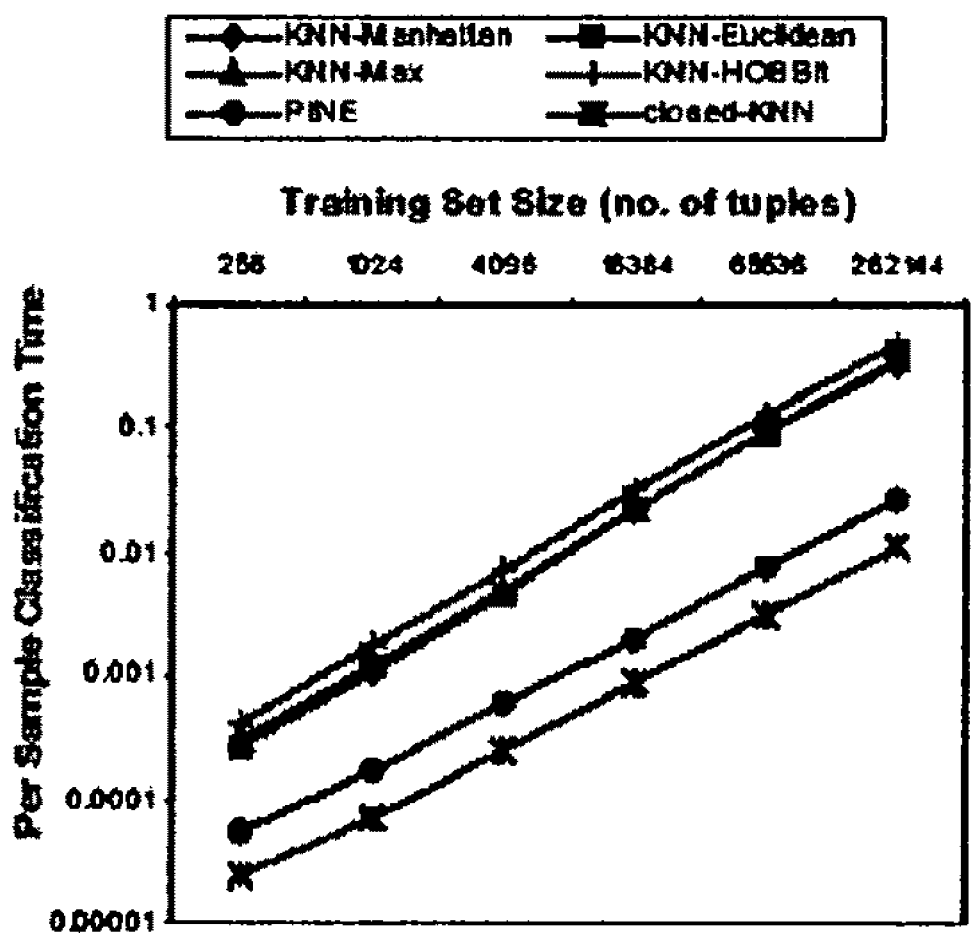
FIG. 30 is a graph depicting classification time per sample (size and classification time are plotted in logarithmic scale).

In terms of speed, from FIG. 30, we see that there is some additional time cost of using PINE, however, this additional cost is relatively small. Notice that both size and classification time are plotted in logarithmic scale. We observe that both closed—KNN and PINE are much faster than KNN using any metric. On the average, PINE is eight times faster than the KNN, and closed-KNN is 10 times faster. Both PINE and closed-KNN increase at a lower rate than KNN methods do when the training set size increases.

It should be noted that Fibonacci sequences of any seed may be used to transform the data into alternate binary representations for the purpose of improving prediction quality of class label assignments.

FIBONACCI HAWAIIAN METRICS AND HOBBIT RINGS. While Hawaiian Metrics or HoBBit metrics are used speed and accuracy in classification is usually achieved.

Fibonacci base sequence: ... 233 144 89 55 34 21 13 8 5 3 2 1 1 ($n_i = n_{(i+1)} + n_{(i+2)}$)
For byte data:

Index: 13 12 11 10 9 8 7 6 5 4 3 2 1 0
Pos: 11 10 9 8 7 6 5 4 3 2 1 0
Fib: 233 144 89 55 34 21 13 8 5 3 2 1 _1_0

| NUM | | | | | | | | | | | | | seed |
|---|---|---|---|---|---|---|---|---|---|---|---|---|---|
| 0 | 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 0 | 1 |
| 2 | 0 | 0 | 0 | 0 | 0 | 0 | 0 | 0 | 0 | 0 | 0 | 1 | 0 |
| 3 | 0 | 0 | 0 | 0 | 0 | 0 | 0 | 0 | 0 | 0 | 1 | 0 | 0 |
| 4 | 0 | 0 | 0 | 0 | 0 | 0 | 0 | 0 | 0 | 0 | 1 | 0 | 1 |
| 5 | 0 | 0 | 0 | 0 | 0 | 0 | 0 | 0 | 1 | 0 | 0 | 0 | 0 |
| 6 | 0 | 0 | 0 | 0 | 0 | 0 | 0 | 0 | 1 | 0 | 0 | 0 | 1 |
| 7 | 0 | 0 | 0 | 0 | 0 | 0 | 0 | 0 | 1 | 0 | 1 | 0 | |
| 8 | 0 | 0 | 0 | 0 | 0 | 0 | 0 | 1 | 0 | 0 | 0 | 0 | |
| 9 | 0 | 0 | 0 | 0 | 0 | 0 | 0 | 1 | 0 | 0 | 0 | 1 | |
| ... | ... | | | | | | | | | | | | |

The result is more Hobbit rings that are thinner and better centered, for better classification. The idea can be pushed even further if a Fibonacci starter value of 0.1 rather than 1 (which results in 16 bit representations and in more plateaus, which is thinner yet)

| | 159 | 98 | 61 | 37 | 23 | 14. | 8.9 | 5.5 | 3.4 | 2.1 | 1.3 | .8 | .5 | .3 | .2 | .1 |
|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 1 | 0 | 0 | 1 | 0 |
| 2 | 0 | 0 | 0 | 0 | 0 | 0 | 0 | 0 | 0 | 1 | 0 | 1 | 0 | 1 | 0 | |
| 3 | 0 | 0 | 0 | 0 | 0 | 0 | 0 | 0 | 1 | 0 | 1 | 0 | 0 | 0 | 1 | |
| 4 | 0 | 0 | 0 | 0 | 0 | 0 | 0 | 1 | 0 | 0 | 0 | 1 | 0 | 0 | 1 | |
| 5 | 0 | 0 | 0 | 0 | 0 | 0 | 0 | 1 | 0 | 1 | 0 | 0 | 1 | 0 | 0 | |
| 6 | 0 | 0 | 0 | 0 | 0 | 0 | 1 | 0 | 0 | 0 | 0 | 0 | 1 | 1 | 0 | |
| 7 | 0 | 0 | 0 | 0 | 0 | 0 | 1 | 0 | 0 | 1 | 0 | 0 | 0 | 1 | 0 | |
| 8 | 0 | 0 | 0 | 0 | 0 | 0 | 1 | 0 | 1 | 0 | 0 | 0 | 1 | 0 | 1 | |
| ... | | | | | | | | | | | | | | | | |

However, there are possible problems that can be presented with these metrics, e.g., eccentricity of Hobbit rings and/or thickness of Hobbit rings. Such problems can be addressed Taking the seed to be 1/B where B is any of Fibonacci (1, 2, 3, 5, ...) gives a representation base that will always include 1.

| | * | * | 75 | 46 | 28. | 17. | 11 | 6.8 | 4.2 | 2.6 | 1.6 | 1 | 0.6 | 0.4 | 0.2 | 0.2 |
|---|---|---|---|---|---|---|---|---|---|---|---|---|---|---|---|---|
| num_ | 15 | 14 | 13 | 12 | 11 | 10 | 9 | 8 | 7 | 6 | 5 | 4 | 3 | 2 | 1 | 0 |
| 0 | 0 | 0 | 0 | 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 0 | 1 | 0 | 1 | 1 |
| 2 | 0 | 0 | 0 | 0 | 0 | 0 | 0 | 0 | 0 | 1 | 0 | 0 | 0 | 1 | 1 | |
| 3 | 0 | 0 | 0 | 0 | 0 | 0 | 0 | 0 | 1 | 0 | 0 | 0 | 0 | 1 | 1 | |
| 4 | 0 | 0 | 0 | 0 | 0 | 0 | 0 | 0 | 1 | 0 | 1 | 0 | 0 | 1 | 1 | |
| 5 | 0 | 0 | 0 | 0 | 0 | 0 | 0 | 1 | 0 | 0 | 0 | 1 | 0 | 0 | 1 | |
| 6 | 0 | 0 | 0 | 0 | 0 | 0 | 0 | 1 | 0 | 1 | 0 | 0 | 0 | 0 | 1 | |
| 7 | 0 | 0 | 0 | 0 | 0 | 0 | 0 | 1 | 0 | 0 | 0 | 0 | 0 | 0 | 1 | |
| ... | | | | | | | | | | | | | | | | | through the use of a Fibonacci base sequence. Generally, we think of binary (and decimal) digital coding of a number:

Binary base sequence, $B = \{..., 2^n, ..., 2^1, 2^0\}$ (decimal base sequence, $D = \{..., 10^n, ..., 10^1, 10^0\}$. Remove the largest base<=number (digit=# of copies removed). Repeat with number:=remainder until remainder=0.

However, if we code using a Fibonacci sequence as base sequence (not B or D), we obtain the following:

Fibonacci base provides multiple representers for most numbers. For seed=s defines s-Canonical Fibonacci representation (sCF) while s-Packed Fibonacci (sPF) is the representation with 1-bits moved as far right as possible, for s=1. As such, the following Data Mining classification method based on Hawaiian Metrics can be used: 1. Form basic CFPtrees and basic PFPtrees (canonical and packed); 2. For a unclassified sample, x, form each hobbit ring mask as CFring-i OR PFring-i=Hring-I; 3. Apply Hring-i to both PFtrees and CFtrees (OR the results together) 4. Vote weighting ratios should be according to the fibonacci index of the ring (i.e., inner ring has index=1, next ring has index=2 . . . ).

IV. C. Cluster Analysis

Data mining in general is the search for hidden patterns that may exist in large databases. Spatial data mining in particular is the discovery of interesting relationships and characteristics that may exist implicitly in spatial databases. In the past 30 years, cluster analysis has been widely applied to many areas. Spatial data is a promising area for clustering. However, due to the large size of spatial data, such as satellite images, the existing methods are not very suitable. Below is described a new method to perform clustering on spatial data utilizing bSQ and PC-trees of the present invention, however, before presenting the new method, a discussion of prior art methods of clustering is provided.

Prior Art Clustering Methods

Given a database of n objects and k, the number of clusters to form, a partitioning technique organizes the objects into k partitions (k≦n), where each partition represents a cluster. The clusters are formed to optimize an objective partitioning criterion, often called a similarity function, such as distance, so that the objects within a cluster are "similar", whereas the objects of different clusters are "dissimilar" in terms of the database attributes.

K-means: The k-means technique proceeds as follows. First, it randomly selects k of the objects, which initially each represent a cluster mean or center. For each of the remaining objects, an object is assigned to the cluster to which it is the most similar, based on the distance between the object and the cluster mean. It then computes the new mean for each cluster. This process iterates until the criterion function converges.

The k-means method, however, can be applied only when the mean of a cluster is defined. And it is sensitive to noisy data and outliers since a small number of such data can substantially influence the mean value.

K-Medoids: The basic strategy of k-medoids clustering techniques is to find k cluster in n objects by first arbitrarily finding a representative object (the medoid) for each cluster. Each remaining object is clustered with the medoid to which it is the most similar. The strategy then iteratively replaces one of the medoids by one of the non-medoids as long as the quality of the resulting clustering is improved.

PAM (Partitioning Around Medoids): PAM attempts to determine k partitions for n objects. After an initial random selection of k-medoids, the technique repeatedly tries to make a better choice of medoids. All of the possible pairs of objects are analyzed, where one object in each pair is considered a medoid, and the other is not. Experimental results show that PAM works satisfactorily for small data sets. But it is not efficient in dealing with medium and large data sets.

CLARA and CLARANS: Instead of finding representative objects for the entire data set, CLARA draws a sample of the data set, applies PAM on the sample, and finds the medoids of the sample. However, a good clustering based on samples will not necessarily represent a good clustering of the whole data set if the sample is biased. As such, CLARANS was proposed which does not confine itself to any sample at any given time. It draws a sample with some randomness in each step of the search.

Clustering Using PC-Trees

From the above, it is clear that the PAM method cannot be used directly for spatial data. Rather, samples like CLARA and CLARANS must be drawn from the original data. As such, with respect to clustering using PC-trees, first is introduced the idea of dense units. Then, the PC-trees are used to generalize the dense units. Finally, the PAM method is adapted on the dense units.

Let $S=B_1 \times B_1 \times \ldots \times B_d$ be a d-dimensional numerical space and $B_1, B_2, \ldots, B_d$ are the dimensions of S. Each pixel of the spatial image data is considered as a d-dimensional points $v=\{v_1, v_2, \ldots, v_d\}$. If every dimension is partitioned into several intervals, then the data space S can be partitioned into non-overlapping rectangular units. Each unit u is the intersection of one interval from each attribute. It has the form $\{u_1, u_2, \ldots, u_d\}$ where $u_i=[l_i, h_i)$ is a right-open interval in the partitioning of $A_i$. It can be said that a point $v=\{v_1, v_2, \ldots, v_d\}$ is contained in a unit $u=\{u_1, u_2, \ldots, u_d\}$ if $l_i<v_i<h_i$ for all $u_i$. The selectivity of a unit is defined to be the fraction of total data points contained in the unit. A unit u is called dense if selectivity (u) is greater than the density threshold r. A cluster is a maximal set of connected dense units.

From original data, all the tuple PC-trees can be generated. Those tuple PC-trees whose root counts are larger than half of the $\max(RC(P_v))$ are defined as dense units. Finally, the PAM method is used to partition all the tuple PC-trees into k clusters. Here is the example:

The following relation contains 4 bands of 4-bit data values (expressed in decimal and binary) (BSQ format would consist of the 4 projections of this relation, R[YIELD], R[Blue], R[Green], R[Red]).

| FIELD COORDS | CLASS LABEL | REMOTELY SENSED REFLECTANCES | | |
|---|---|---|---|---|
| X, Y | YIELD | Blue | Green | Red |
| 0, 0 | 3 | 7 | 8 | 11 |
| 0, 1 | 3 | 3 | 8 | 15 |
| 0, 2 | 7 | 3 | 4 | 11 |
| 0, 3 | 7 | 2 | 5 | 11 |
| 1, 0 | 3 | 7 | 8 | 11 |
| 1, 1 | 3 | 3 | 8 | 11 |
| 1, 2 | 7 | 3 | 4 | 11 |
| 1, 3 | 7 | 2 | 5 | 11 |
| 2, 0 | 2 | 11 | 8 | 15 |
| 2, 1 | 2 | 11 | 8 | 15 |
| 2, 2 | 10 | 10 | 4 | 11 |
| 2, 3 | 15 | 10 | 4 | 11 |
| 3, 0 | 2 | 11 | 8 | 15 |
| 3, 1 | 10 | 11 | 8 | 15 |
| 3, 2 | 15 | 10 | 4 | 11 |
| 3, 3 | 15 | 10 | 4 | 11 |

| FIELD COORDS | CLASS LABEL | REMOTELY SENSED REFLECTANCES | | |
|---|---|---|---|---|
| X, Y | YIELD | Blue | Green | Red |
| 0, 0 | 0011 | 0111 | 1000 | 1011 |
| 0, 1 | 0011 | 0011 | 1000 | 1111 |
| 0, 2 | 0111 | 0011 | 0100 | 1011 |
| 0, 3 | 0111 | 0010 | 0101 | 1011 |
| 1, 0 | 0011 | 0111 | 1000 | 1011 |
| 1, 1 | 0011 | 0011 | 1000 | 1011 |
| 1, 2 | 0111 | 0011 | 0100 | 1011 |
| 1, 3 | 0111 | 0010 | 0101 | 1011 |
| 2, 0 | 0010 | 1011 | 1000 | 1111 |
| 2, 1 | 0010 | 1011 | 1000 | 1111 |
| 2, 2 | 1010 | 1010 | 0100 | 1011 |
| 2, 3 | 1111 | 1010 | 0100 | 1011 |
| 3, 0 | 0010 | 1011 | 1000 | 1111 |
| 3, 1 | 1010 | 1011 | 1000 | 1111 |
| 3, 2 | 1111 | 1010 | 0100 | 1011 |
| 3, 3 | 1111 | 1010 | 0100 | 101 |

This dataset is converted to bSQ format. We display the bSQ bit-bands values in their spatial positions, rather than displaying them in 1-column files. The Band-1 bit-bands are:

| $B_{11}$ | $B_{12}$ | $B_{13}$ | $B_{14}$ |
|---|---|---|---|
| 0000 | 0011 | 1111 | 1111 |
| 0000 | 0011 | 1111 | 1111 |
| 0011 | 0001 | 1111 | 0001 |
| 0111 | 0011 | 1111 | 0011 |

Thus, the Band-1 Basic PC-trees are as follows (tree pointers are omitted).

| $PC_{1,1}$ | $PC_{1,2}$ | $PC_{1,3}$ | $PC_{1,4}$ |
|---|---|---|---|
| 5 | 7 | 16 | 11 |
| 0 0 1 4 | 0 4 0 3 | | 4 4 0 3 |
| 0001 | 0111 | | 0111 |

The PC-trees for 4-bit values (Value PC-trees) are given. The creation process for only, $PC_{1,0011}$, is shown as an example.

$PC_{1,0011} = PC_{1,1}'$ AND $PC_{1,2}'$ AND $PC_{1,3}$ AND $PC_{1,4}$ since,

| 4 | 11 | 9 | 16 | 11 | |
|---|---|---|---|---|---|
| 4 0 0 0 | 4 4 3 0 | 4 0 4 1 | | 4 4 0 3 | |
| | 1110 | 1000 | | 0111 | |
| 0 1 | 20 21 22 | | | | (pure1 paths of $PC_{1,1}'$) |
| 0 | 2 | 31 | | | (pure1 paths of $PC_{1,2}'$) |
| 0 1 | | 31 32 33 | | | (pure1 paths of $PC_{1,4}$, ($PC_{1,3}$ has no pure1 paths)) |
| 0 | | | | | (pure1 paths of $PC_{1,0011}$). |

| $PC_{1,0000}$ | $PC_{1,0100}$ | $PC_{1,1000}$ | $PC_{1,1100}$ | $PC_{1,0010}$ | $PC_{1,0110}$ | $PC_{1,1010}$ | $PC_{1,1110}$ |
|---|---|---|---|---|---|---|---|
| 0 | 0 | 0 | 0 | 3 | 0 | 2 | 0 |
| | | | | 0 0 3 0 | | 0 0 1 1 | |
| | | | | 1110 | | 0001 1000 | |

| $PC_{1,0001}$ | $PC_{1,0101}$ | $PC_{1,1001}$ | $PC_{1,1101}$ | $PC_{1,0011}$ | $PC_{1,0111}$ | $PC_{1,1011}$ | $PC_{1,1111}$ |
|---|---|---|---|---|---|---|---|
| 0 | 0 | 0 | 0 | 4 | 4 | 0 | 3 |
| | | | | 4 0 0 0 | 0 4 0 0 | | 0 0 0 3 |
| | | | | | | | 0111 |

| $B_{21}$ | $B_{22}$ | $B_{23}$ | $B_{24}$ |
|---|---|---|---|
| 0000 | 1000 | 1111 | 1110 |
| 0000 | 1000 | 1111 | 1110 |
| 1111 | 0000 | 1111 | 1100 |
| 1111 | 0000 | 1111 | 1100 |

| $PC_{2,0000}$ | $PC_{2,0100}$ | $PC_{2,1000}$ | $PC_{2,1100}$ | $PC_{2,0010}$ | $PC_{2,0110}$ | $PC_{2,1010}$ | $PC_{2,1110}$ |
|---|---|---|---|---|---|---|---|
| 0 | 0 | 0 | 0 | 2<br>0 2 0 0<br>0101 | 0 | 4<br>0 0 0 4 | 0 |

| $PC_{2,0001}$ | $PC_{2,0101}$ | $PC_{2,1001}$ | $PC_{2,1101}$ | $PC_{2,0011}$ | $PC_{2,0111}$ | $PC_{2,1011}$ | $PC_{2,1111}$ |
|---|---|---|---|---|---|---|---|
| 0 | 0 | 0 | 0 | 4<br>2 2 0 0<br>0101 1010 | 2<br>2 0 0 0<br>1010 | 4<br>0 0 4 0 | 0 |

| $B_{31}$ | $B_{32}$ | $B_{33}$ | $B_{34}$ |
|---|---|---|---|
| 1100 | 0011 | 0000 | 0001 |
| 1100 | 0011 | 0000 | 0001 |
| 1100 | 0011 | 0000 | 0000 |
| 1100 | 0011 | 0000 | 0000 |

| $PC_{3,0000}$ | $PC_{3,0100}$ | $PC_{3,1000}$ | $PC_{3,1100}$ | $PC_{3,0010}$ | $PC_{3,0110}$ | $PC_{3,1010}$ | $PC_{3,1110}$ |
|---|---|---|---|---|---|---|---|
| 0 | 6<br>0 2 0 4<br>1010 | 8<br>4 0 4 0 | 0 | 0 | 0 | 0 | 0 |

| $PC_{3,0001}$ | $PC_{3,0101}$ | $PC_{3,1001}$ | $PC_{3,1101}$ | $PC_{3,0011}$ | $PC_{3,0111}$ | $PC_{3,1011}$ | $PC_{3,1111}$ |
|---|---|---|---|---|---|---|---|
| 0 | 2<br>0 2 0 0<br>0101 | 0 | 0 | 0 | 0 | 0 | 0 |

| $B_{41}$ | $B_{42}$ | $B_{43}$ | $B_{44}$ |
|---|---|---|---|
| 1111 | 0100 | 1111 | 1111 |
| 1111 | 0000 | 1111 | 1111 |
| 1111 | 1100 | 1111 | 1111 |
| 1111 | 1100 | 1111 | 1111 |

| $PC_{4,0000}$ | $PC_{4,0100}$ | $PC_{4,1000}$ | $PC_{4,1100}$ | $PC_{4,0010}$ | $PC_{4,0110}$ | $PC_{4,1010}$ | $PC_{4,1110}$ |
|---|---|---|---|---|---|---|---|
| 0 | 0 | 0 | 0 | 0 | 0 | 0 | 0 |

| $PC_{4,0001}$ | $PC_{4,0101}$ | $PC_{4,1001}$ | $PC_{4,1101}$ | $PC_{4,0011}$ | $PC_{4,0111}$ | $PC_{4,1011}$ | $PC_{4,1111}$ |
|---|---|---|---|---|---|---|---|
| 0 | 0 | 0 | 0 | 0 | 0 | 11<br>3 4 0 4<br>1011 | 5<br>1 0 4 0<br>0100 |

From the Value PC-trees, we can generate all the Tuple PC-trees. Here, we give all the non-zero trees:

| P-0010,1011,1000,1111 | 3 | 0 0 3 0 | 1110 |
| P-1010,1010,0100,1011 | 1 | 0 0 0 1 | 1000 |
| P-1010,1011,1000,1111 | 1 | 0 0 1 0 | 0001 |
| P-0011,0011,1000,1011 | 1 | 1 0 0 0 | 0001 |
| P-0011,0011,1000,1111 | 1 | 1 0 0 0 | 0100 |

-continued

| P-0011,0111,1000,1011 | 2 | 2 0 0 0 | 1010 |
| P-0111,0010,0101,1011 | 2 | 0 2 0 0 | 0101 |
| P-0111,0011,0100,1011 | 2 | 0 2 0 0 | 1010 |
| P-1111,1010,0100,1011 | 3 | 0 0 0 3 | 0111 |

Then the dense units:

| P-0010,1011,1000,1111 | 3 | 0 0 3 0 | 1110 |
| P-0011,0111,1000,1011 | 2 | 2 0 0 0 | 1010 |
| P-0111,0010,0101,1011 | 2 | 0 2 0 0 | 0101 |
| P-0111,0011,0100,1011 | 2 | 0 2 0 0 | 1010 |
| P-1111,1010,0100,1011 | 3 | 0 0 0 3 | 0111 |

Now, use PAM method to partition the tuple PC-trees into k clusters (k=4):

| cluster1: | P-0010,1011,1000,1111 | 3 | 0 0 3 0 | 1110 |
| cluster2: | P-0011,0111,1000,1011 | 2 | 2 0 0 0 | 1010 |
| cluster3: | P-0111,0010,0101,1011 | 2 | 0 2 0 0 | 0101 |
|  | P-0111,0011,0100,1011 | 2 | 0 2 0 0 | 1010 |
| cluster4: | P-1111,1010,0100,1011 | 3 | 0 0 0 3 | 0111 |

If this is compared to the result of decision tree partitioning, it can be said that the results show the same characteristics as the classification (cluster1 all in C1, cluster2 all in C2, cluster3 in C3 and C4, cluster 4 all in C5).

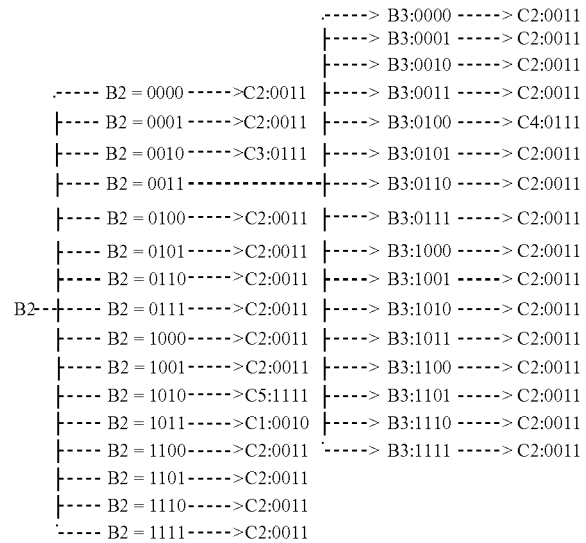

The result of the decision tree

Thus, while the PAM technique cannot be used directly it can be seen that when CLARA and CLARANS are used to first draw samples from the original data, the PAM technique can be adapted. The PAM technique that is used need only deal with the tuple PC-trees, and the number of PC-trees are much smaller than the dataset CLARA and CLARANS need to deal with. To show the advantage in performance, it should be noted that the ANDing of the PC-trees can be done in parallel.

A PC-tree-based K-means clustering method has been developed (very similar in approach to the PC-tree K-nearest neighbor classification method). This method does not require a data set scan after the PC-trees are created. Templates for K-means sets are created directly from the PC-trees for any set of K-means. The new clusters counts and means can be calculated from the basic PC-trees directly without need of a dataset scan by creating a template tree for each cluster. The algorithm ends when the templates do not change after reclustering. Thus, the entire clustering process can be done without the need for even one data set scan. This is a revolutionary advance over existing K-means methods.

VI. Applications of bSQ and PC-tree Technology

The above description has described various data mining techniques utilizing bSQ and PC-tree technology with specific reference to spatial datasets. However, as mentioned above, the bSQ and PC-tree technology is suited to placing virtually any type of data that is organized into n-arrays into a state of data mining readiness. Examples of other data collection areas to which the technology of the present invention may be applied are provided below.

VI.A. Data Mining of Microarray Data Using Association Rule Mining

Advances made in parallel, high-throughput technologies in the area of molecular biology has led to exponential growth in genomic data. The emphasis during the last many years was on sequencing the genome of organisms. The current emphasis lies in extracting meaningful information from the huge DNA sequence and expression data. The techniques currently employed to do analysis of microarray expression data is clustering and classification. These techniques present their own limitation as to the amount of useful information that can be derived. However, the bSQ and PC-tree technology of the present invention enables association rule mining to be performed on microarray data. With the technology of the present invention, the PC-tree is used to measure gene expression levels and does so by treating the microarray data as spatial data. Specifically, each spot on the microarray is presented as a pixel with corresponding red and green ratios. The microarray data is reorganized into an 8-bit bSQ file, wherein each attribute or band is stored as a separate file. Each bit is then converted in a quadrant base tree structure PC-tree from which a data cube is constructed and meaningful rules are readily obtained.

DNA microarrays are becoming an important tool for monitoring and analyzing gene expression profiles of thousands of genes simultaneously. Due to their small size, high densities and compatibility with fluorescent labeling, microarray technology provides an economic, robust, fully automated approach toward examining and measuring temporal and spatial global gene expression changes. Although fundamental differences exist between the two microarray technologies—cDNA microarrays and Oligonucleotiede arrays, their strength lies in the massive parallel analysis of thousands of genes simultaneously. The microarray data yields valuable information about gene functions, inter-gene dependencies and underlying biological processes. Such information may help discover gene regulation pathways, metabolic pathways, relation of genes with their environments, etc.

The microarray data format is very similar to the market basket format (association rule mining was originally proposed for market basket data to study consumer purchasing patterns in retail stores). The data mining model for market research dataset can be treated as a relation R(Tid, $i_1, \ldots, i_n$) where Tid is the transaction identifier and $i_1, \ldots, i_n$ denote the feature attributes—all the items available for purchase from the store. Transactions constitute the rows in the data-table whereas itemsets form the columns. The values for the itemsets for different transactions are in binary representation; 1 if the item is purchased, 0 if not purchased. The microarray data can be represented as a relation R(Gid, $T_1, \ldots, T_n$) where Gid is the gene identification for each gene and $T_1, \ldots, T_n$ are the various kinds of treatments to which the genes were exposed. The genes constitute the rows in the data table whereas treatments are the columns. The values are in the form of normalized Red/Green color ratios representing the abundance of transcript for each spot on the microarray. This table can be called a "gene table".

Currently, the data mining techniques of clustering and classification are being applied to the gene table. In clustering and classification techniques, the dataset is divided into clusters/classes by grouping on the rows (genes). However, utilizing the technology of the present invention the microarray dataset can be formatted in to a "treatment table", which is obtained by flipping the gene table. The relation R of a treatment table can be represented as $R(Tid, G_1, \ldots, G_n)$ where Tid represents the treatment ids and $G_1, \ldots, G_n$ are the gene identifiers. The treatment table provides a convenient means to treat genes as spatial data. The goal then is to mine for rules among the genes by associating the columns (genes) in the treatment table. The treatment table can be viewed as a 2-dimensional array of gene expression values and, as such, can be organized into the bSQ format of the present invention.

The Red/Green ratios for each gene, which represents the gene expression level, can be represented as a byte. The bSQ format breaks each of the Red/Green values into separate files by partitioning the eight bits of each byte used to store the gene expression value. Each bSQ file can then be organized into the PC-tree structure of the present invention. As described above, the PC-trees are basically quadrant-wise, Peano-order-run-length-compressed, representations of each bSQ file and a data-mining-ready structure for spatial data mining. The root of the PC-tree contains the 1 bit count of the entire bit presenting the microarray spot. The next level of the tree contains the 1-bit counts of the four quadrants in raster order. At the next level, each quadrant is partitioned into sub-quadrants and their 1-bit counts in raster order constitute the children of the quadrant node. This construction is continued recursively down each tree path until the sub-quadrant is pure (entirely 1-bits or entirely 0-bits), which may or may not be at the leaf level, i.e., the 1-by-1 sub-quadrant. It is a lossless and compressed data structure representation of a 1-bit file from which the bit can be completely reconstructed and which also contains the 1-bit count for each and every quadrant in the original microarray data. The concept here is to recursively divide the entire data into quadrants and record the count of 1-bits for each quadrant, thus, forming a quadrant count tree. As explained earlier, a variation of the PC-tree, the peano mask tree (PM-tree), can be used for efficient implementation of PC-tree operations.

As such, eight basic PC-trees are created and can be combined using simple logical operations (AND, NOT, OR, COMPLEMENT) to recover the original data or produce PC-trees at any level of precision for any value or combination of values. For example, a PC-tree (called a value PC-tree) can be constructed for all occurrences of the value 11010011 by ANDing the basic PC-trees (for each 1-bit) and their complements (for each 0-bit): PCb, 11010011=PCb1 AND PCb2 AND PCb3' AND PCb4 AND PCb5' AND PCb6' AND PCb7 AND PCb8 where ' indicates the bit-complement. The power of this representation is that by simple AND operations all combinations and permutations of the data can be constructed and further that the resulting representation has the hierarchical count information embedded to facilitate data mining.

Once the PC-trees are established they can be successfully used to derive rules of interest from the microarray data. These rules can provide valuable information to a biologist as to the gene regulatory pathways and identify important relationships between the different gene expression patterns hitherto unknown. The biologist may be interested in some specific kind of rules. These rules can be called as "rules of interest". In gene regulatory pathways, a biologist may be interested in identifying genes that govern the expression of other sets of genes. These relationships can be represented as follows: $\{G_1, \ldots, G_n\} \rightarrow G_m$ where $G_1, \ldots, G_n$ represents the antecedent and Gm represents the consequent of the rule. The intuitive meaning of this rule is that for a given confidence level the expression of $G_1, \ldots, G_n$ genes will result in the expression of Gm of the gene. The P-ARM technique and the p-gen technique described earlier can be used for mining association rules on microarray data.

VI.B. PC-tree Based Simulation and Verification of Digital Circuits

The PC-trees of the present invention can further be used as the core data structure to store design data and to simulate operation of digital circuits, e.g., VLSI. The complexity of integrated circuits is ever increasing with the P6 (Pentium III family) architecture having 5-10 million transistors, the Willamette (Pentium4) having up to 38 million transistors, and even full custom ASICs having over a million transistors. The requirements of most integrated circuits do not allow for error in their design or manufacture. As such, the operational validity of the circuit must be simulated and verified, often at great expense through current simulation systems such as Verilog.

In validating an integrated circuit, various challenges must be faced, e.g., does the circuit perform correctly when tested for functionality X, does a subset of the chip perform correctly when tested for functionality X, does a subset of the circuit "communicate" correctly with the rest of the circuit when tested for functionality X, does the circuit satisfy all the above criteria for all known functions, does the circuit perform correctly for erroneous, i.e., don't care, inputs, etc. The PC-trees of the present invention can be utilized to address these challenges through logic/RTL simulation of circuits and through equivalence checking.

In simulation of an integrated circuit, the circuit is stimulated, i.e., input vectors are applied to the circuit, the values are propagated through the circuit and the output values are observed. In equivalence checking, two circuits are stimulated, one of them being the known correct circuit and the other, the under test circuit. The output of the two circuits are then checked to see if their output matches when both are given the same input vector.

Utilizing the function tables of the various types of circuits, examples of the function tables for a half adder circuit and for a full adder circuit are provided in the tables below, PC-trees can be established. Upon encoding of the function table of a circuit into a PC-tree the structural attributes are the inputs while the feature attributes are the outputs and/or intermediate states. The advantage of simulation using PC-trees over other methods is that all outputs are taken into account instead of treating each output as a single Boolean function. With circuit simulation, stimulating an input corresponds to checking all of the basic PC-trees (each corresponds to an output bit) at the one location for the correct bit. With equivalence checking, a simple XOR of each pair of basic PC-trees, one from each circuit under comparison, is performed. If the root-count is zero, the circuits are equivalent. If the root-count is nonzero, the circuits are in-equivalent with the root-count providing a quantitative measure of that inequivalence.

| Function Table - Half Adder Circuit | | | |
|---|---|---|---|
| Bit1 | Bit2 | Sum | Carry |
| 0 | 0 | 0 | 0 |
| 0 | 1 | 1 | 0 |
| 1 | 0 | 1 | 0 |
| 1 | 1 | 0 | 1 |

| Function Table - Full Adder Circuit | | | | |
|---|---|---|---|---|
| input1 | input2 | Carry Forward | Sum | Carry |
| 0 | 0 | 0 | 0 | 0 |
| 0 | 0 | 1 | 1 | 0 |
| 0 | 1 | 0 | 1 | 0 |
| 0 | 1 | 1 | 0 | 1 |
| 1 | 0 | 0 | 1 | 0 |
| 1 | 0 | 1 | 0 | 1 |
| 1 | 1 | 0 | 0 | 1 |
| 1 | 1 | 1 | 1 | 1 |

Figure 31:
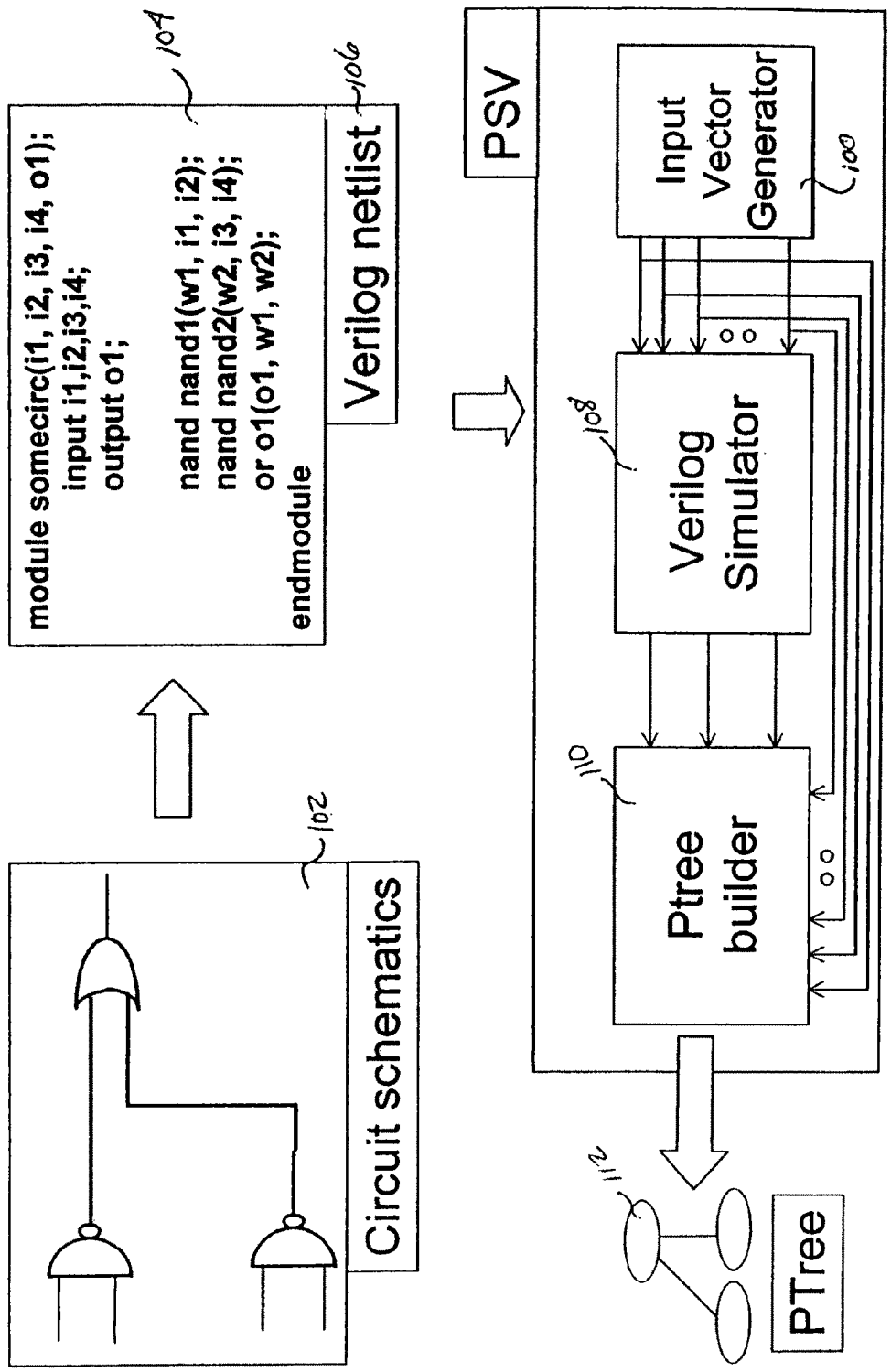
FIG. 31 provides a block diagram of a scheme to implement simulation and equivalence checking of integrated circuits through use of PC-trees.

Referring to FIG. 31, the implementation scheme for simulation and equivalence checking with PC-trees is shown and includes: 1. logic to generate the stimulus (input bit vectors) to a given digital circuit, i.e., input vector generator 100; 2. the digital circuit itself, an example of which is shown in block 102, the circuit is then preferably coded, see block 104, and netlisted in Verilog, see block 106; 3. a simulation system to simulate the bit vectors "through" the digital circuit and generate outputs, such as a Verilog simulator 108; and 4. a PC-tree generation system 110 that combines the input bit vector with the result of the simulation to produce the PC-tree 112.

Utilizing PC-trees in combination with Verilog simulation rather than Verilog simulation on its own provides logic/RTL simulation of digital circuits with an increase of at least two orders of magnitude improvement in performance. Further, formal verification for equivalence of any two circuits with the benefit of PC-trees shows an improvement of at least an order of magnitude in performance.

VI.C. PC-tree Based Nano-Technology Applications

The PC-trees of the present invention can further be used as the core data structure for the manufacture of a 3-D display devise based on Alien Technology's (Morgan Hill, Calif.) Fluidic Self Assembly technology for building single layer display devices on a flexible transparent substrate. By layering thousands of such sheets into a transparent cube with a nano-scale computer at each 3-D pixel position, a 3-dimensional array of parallel computing devices can serve as distribute PC-tree nodes on a massive scale. Each computer could be sent requests through a wireless communication system and could activate color LEDs based on the results of local PC-tree AND operations. Such a 3-D display device would be far superior to existing holographic 3-D displays in that it would be implemented on a 3-dimensional physical substrate. Viewers would be free to circulate around the display for viewing from any angle—something that is impossible with holographic displays. Also, the display should be much sharper and more dependable that the holographic technology can provide.

In a battlespace, nano-sensor (also being considered by Alien and others) could be dispersed throughout the battle field. Each nano-sensor would act as a detection platform for one bit position of one feature attribute band. The devise would turn on (set a specific memory location to 1) when a low-threshold is sensed and turn off when (and if) a high-threshold is exceeded. In this manner, each sensor would be acting as the processing and storage node for a small quadrant of the space. Sensor would only need to communicate in one direction with a control node to provide needed counts.

Many other nano-technology applications of PC-tree technology are possible. These are but a few examples.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

What is claimed is:

1. A system for performing data mining in a set of binary data arranged as a plurality of data items, wherein each data item has a plurality of bits, each bit in a corresponding one of a plurality of bit positions defined for each data item, the system comprising:
   a computer system having hardware including a processor and data storage, wherein the computer system is programmed to:
      arrange the set of binary data in the data storage such that the binary data is in bit position groups, wherein each bit position group corresponds to a different one of the plurality of bit positions and includes one bit from each of the plurality of data items which has that one bit position;
      compress the binary data of each bit position group such that each bit position group is represented by a compressed data structure, wherein the set of binary data is represented by a plurality of compressed data structures; and
      perform a data mining technique using the plurality of compressed data structures to effect a result of detecting at least one of a non-preselected pattern and a non-preselected relationship among the plurality of data items of the set of binary data.

2. The system of claim 1, wherein the data mining technique is at least one data mining technique selected from the group consisting of: association rule mining, classification, and clustering.

3. The system of claim 1, wherein the data mining technique is at least one data mining technique selected from the group consisting of: classification, and clustering.

4. The system of claim 1, wherein the set of binary data is arranged as an n-dimensional table of binary data.

5. The system of claim 1, wherein each group is maintained as a separate file.

6. The system of claim 1, wherein the data comprises data of at least one type selected from the group consisting of: spatial data, bioinformatics data, microarray data, data representing an integrated circuit.

7. The system of claim 1, wherein a plurality of partitions is defined for each bit position group, and wherein the compressed data structure corresponding to each bit position group includes a plurality of symbols, each symbol representing a value of a corresponding partition of the corresponding bit position group.

8. The system of claim 7, wherein the value of the corresponding partition is indicative of an existence or non-existence of a particular binary value of that partition.

9. The system of claim 7, wherein the plurality of partitions are arranged as quadrants.

10. The system of claim 7, wherein the plurality of partitions are arranged as nested partitions, with each bit position group partitioned at a first level into first-level partitions, and each of the first-level partitions partitioned into second-level partitions; and
wherein the compressed data structure includes a first set of at least one symbol representing values for each of the first-level partitions, and a second set of at least one symbol representing values for each of the second-level partitions.

11. A computer system for performing data mining in a set of binary data arranged as a plurality of data items, wherein each data item has a plurality of bits, each bit in a corresponding one of a plurality of bit positions defined for each data item, the computer system comprising:
means for arranging the set of binary data in a data storage device accessible by the computer system such that the binary data is in bit position groups wherein each bit position group corresponds to a different one of the plurality of bit positions and includes one bit from each of the plurality of data items which has that one bit position;
means for compressing the binary data of each bit position group such that each bit position group is represented by a compressed data structure, wherein the set of binary data is represented by a plurality of compressed data structures; and
means for performing a data mining technique using the plurality of compressed data structures to effect a result of detecting at least one of a non-preselected pattern and a non-preselected relationship among the data items of the set of binary data.

12. A computer-implemented method of performing data mining on data that is initially arranged as a plurality of data items, each data item having a plurality of bits in a plurality of bit positions, each bit being in one of the plurality of bit positions defined for each data item, the method comprising:
using a computer system, arranging the data into bit position-based groups in a data store of the computer system, wherein each bit position-based group corresponds to a different one of each of the bit positions and includes one bit from each of the plurality of data items which has that one bit position; and
using the computer system, compressing the data of each of the bit position-based groups into a compressed representation to produce a plurality of compressed representations of the data; and
using the computer system, performing data mining using the plurality of compressed representations to effect a result of detecting at least one of a non-preselected pattern and a non-preselected relationship among the data items of the set of binary data.

13. The method of claim 12, wherein the performing of the data mining includes performing at least one data mining technique selected from the group consisting of: association rule mining, classification, and clustering.

14. The method of claim 12, wherein the performing of the data mining includes performing a classification technique.

15. The method of claim 12, wherein the performing of the data mining on the plurality of compressed representations includes logically combining the compressed representations with one another.

16. The method of claim 12, wherein the performing of the data mining on the plurality of compressed representations includes a step for logically combining the compressed representations with one another.

17. The method of claim 12, wherein the compressing of the data of each of the bit position-based groups includes:
defining a plurality of partitions for each of the bit position-based groups; and
for each partition, indicating an existence or non-existence of a particular data value.

18. The method of claim 17, wherein the defining of the plurality of partitions includes dividing each partition as nested quadrants.

19. The method of claim 12, wherein the compressing of the data of each of the bit position-based groups includes:
defining a plurality of partitions for each of the bit position-based groups; and
producing a compressed data structure corresponding to each bit position-based group, wherein each compressed data structure includes a plurality of symbols, each symbol representing a value of a corresponding partition of that bit position-based group.

20. The method of claim 19, wherein the defining of the plurality of partitions includes:
creating partitions at a first level into first-level partitions;
partitioning each of the first-level partitions into second-level partitions; and wherein the producing the compressed data structure includes:
creating a first set of at least one symbol representing values for each of the first-level partitions; and
creating a second set of at least one symbol representing values for each of the second-level partitions.

21. The method of claim 12, wherein the arranging of the data into bit position-based groups includes storing each bit position-based group as a separate file.

* * * * *